United States Patent
Schuurman et al.

(10) Patent No.: US 9,322,035 B2
(45) Date of Patent: Apr. 26, 2016

(54) RECOMBINANT IGG4 MONOVALENT ANTIBODIES

(75) Inventors: Janine Schuurman, Diemen (NL); Tom Vink, Alphen aan den Rijn (NL); Jan Van De Winkel, Zeist (NL); Aran Frank Labrijn, Nigtevecht (NL); Paul Parren, Odijk (NL); Willem Karel Bleeker, Amsterdam (NL); Frank Beurskens, Culemborg (NL); Patrick Van Berkel, Utrecht (NL)

(73) Assignee: GENMAB A/S, Copenhagen (DK)

( * ) Notice: Subject to any disclaimer, the term of this patent is extended or adjusted under 35 U.S.C. 154(b) by 1357 days.

(21) Appl. No.: 12/602,419

(22) PCT Filed: May 30, 2008

(86) PCT No.: PCT/DK2008/050127
§ 371 (c)(1),
(2), (4) Date: Jun. 30, 2010

(87) PCT Pub. No.: WO2008/145140
PCT Pub. Date: Dec. 4, 2008

(65) Prior Publication Data
US 2010/0306867 A1    Dec. 2, 2010

(30) Foreign Application Priority Data

May 31, 2007 (DK) .................................. 2007 00795

(51) Int. Cl.
*C07K 16/00* (2006.01)
*C12N 15/85* (2006.01)
*C07K 16/28* (2006.01)

(52) U.S. Cl.
CPC ............ *C12N 15/8509* (2013.01); *C07K 16/00* (2013.01); *C07K 16/2887* (2013.01); *A01K 2227/105* (2013.01); *A01K 2267/01* (2013.01); *C07K 2317/21* (2013.01); *C07K 2317/55* (2013.01); *C07K 2317/732* (2013.01); *C07K 2317/77* (2013.01); *C12N 2740/16011* (2013.01)

(58) Field of Classification Search
None
See application file for complete search history.

(56) References Cited

U.S. PATENT DOCUMENTS

| | | | |
|---|---|---|---|
| 6,737,056 B1 * | 5/2004 | Presta | 424/133.1 |
| 9,085,625 B2 | 7/2015 | Labrijn et al. | |
| 2003/0118592 A1 * | 6/2003 | Ledbetter et al. | 424/178.1 |
| 2005/0048572 A1 * | 3/2005 | Reilly et al. | 435/7.1 |
| 2007/0105199 A1 | 5/2007 | Yan et al. | |
| 2008/0063635 A1 * | 3/2008 | Takahashi et al. | 424/130.1 |
| 2008/0181892 A1 | 7/2008 | Ledbetter et al. | |
| 2009/0226421 A1 * | 9/2009 | Parren et al. | 424/130.1 |
| 2009/0317382 A1 * | 12/2009 | Losen et al. | 424/131.1 |
| 2010/0267934 A1 * | 10/2010 | Van De Winkel et al. | 530/387.3 |
| 2010/0325744 A1 | 12/2010 | Schuurman et al. | |

FOREIGN PATENT DOCUMENTS

| WO | 02/12437 A2 | 2/2002 |
|---|---|---|
| WO | 03/000176 A2 | 1/2003 |
| WO | 2004/026427 A2 | 4/2004 |
| WO | WO 2004035752 A2 * | 4/2004 |
| WO | 2004/045512 A2 | 6/2004 |
| WO | 2004/056847 A2 | 7/2004 |
| WO | 2005/047336 A1 | 5/2005 |
| WO | 2005/063816 A2 | 7/2005 |
| WO | WO 2006033386 A1 * | 3/2006 |
| WO | 2007/024715 A9 | 3/2007 |
| WO | 2007/059782 A1 | 5/2007 |
| WO | 2007/068255 A1 | 6/2007 |

OTHER PUBLICATIONS

Tuaillon et al (PNAS 1993; 90: 3720-3724).*
Horgan et al (Studies on Antigen Binding by Intact and Hinge-Deleted Chimeric Antibodies, 1993, J of Immuno, vol. 150, p. 5400-5407).*
Aalberse et al (IgG4 Breaking the Rules, 2002, Immunol, vol. 105, p. 9-19).*
Dall'Acqua et al (Contribution of Domain Interface Residues to the Stability of Antibody CH3 Domain Homodimers, 1998, Biochem, vol. 37, p. 9266-9273).*
Genmab (powerpoint presentation, 2006).*
Aalberse, Rob C. et al., "IgG4 breaking the rules," Immunology, vol. 105:9-19 (2002).
Angal, S. et al., "A Single Amino Acid Substitution Abolishes the Heterogeneity of Chimeric Mouse/Human (IgG4) Antibody," Molecular Immunology, vol. 30(1):105-108 (1993).
Biewenga, Jeike et al., "IgA1 half molecules in human multiple myeloma and the in vitro production of similar fragments from intact IgA1 molecules," Clin. exp. Immunol., vol. 51:395-400 (1983).
Bloom, James W. et al., "Intrachain disulfide bond in the core hinge region of human IgG4," Protein Science, vol. 6:407-415 (1997).
Brekke, Ole Henrik et al., "Activation of complement by an IgG molecule without a genetic hinge," Nature, vol. 363:628-630 (1993).
Brekke, Ole Henrik et al., Correction "Activation of complement by an IgG molecule without a genetic hinge," Nature, vol. 383:103 (1996).
Dall'Acqua, William et al., "A Mutational Analysis of Binding Interactions in an Antigen—Antibody Protein—Protein Complex," Biochemistry, vol. 37:7981-7991 (1998).

(Continued)

*Primary Examiner* — Sean Aeder
*Assistant Examiner* — Julie Wu
(74) *Attorney, Agent, or Firm* — Nelson Mullins Riley & Scarborough LLP; Jane E. Remillard, Esq.; Christopher L. Frank

(57) ABSTRACT

The invention relates to novel non-human transgenic animals, which upon antigenic stimulation are capable of producing monovalent antibodies binding to a selected antigen, modified heavy chain transgenes, methods for producing the non-human transgenic animals, methods for immunizing the non-human transgenic animals for as well as monovalent antibodies obtainable by such immunization methods.

6 Claims, 30 Drawing Sheets

(56) References Cited

OTHER PUBLICATIONS

Dall'Acqua, William et al., "Contribution of Domain Interface Residues to the Stability of Antibody CH3 Domain Homodimers," Biochemistry, vol. 37:9266-9273 (1998).

Dall'Acqua, William F. et al., "Increasing the Affinity of a Human IgG1 for the Neonatal Fc Receptor: Biological Consequences," The Journal of Immunology, vol. 169:5171-5180 (2002).

Dall'Acqua, William F. et al., "Modulation of the Effector Functions of a Human IgG1 through Engineering of Its Hinge Region," The Journal of Immunology, vol. 177:1129-1138 (2006).

Dall'Acqua, William F. et al., "Properties of Human IgG1s Engineered for Enhanced Binding of the Neonatal Fc Receptor (FcRn)," The Journal of Biological Chemistry, vol. 281(33):23514-23524 (2006).

Deng, Liang et al., "Detection and qualification of the human IgG4 half-molecule, HL, from unpurified cell-culture supernatants," Biotechnol. Appl. Biochem., vol. 40:261-269 (2004).

Gallango, Maria L. et al., "An Unusual Case of Waldenstrom Macroglobulinemia with Half Molecules of IgG in Serum an dUrine," Blut, vol. 48:91-97 (1983).

Gregory, L. et al., "The Solution Conformations of the Subclasses of Human IgG Deduced from Sedimentation and Small Angle X-Ray Scattering Studies," Molecular Immunology, vol. 24(8):821-829 (1987).

Guddat, Luke W. et al., "Three-dimensional structure of a human immunoglobulin with a hinge deletion," Proc. Natl. Acad. Sci. USA, vol. 90:4271-4275 (1993).

Haringman, Jasper J. et al., "A Randomized Controlled Trial With an Anti-CCL2 (Anti-Monocyte Chemotactic Protein 1) Monoclonal Antibody in Patients With Rheumatoid Arthritis," Arthritis & Rheumatism, vol. 54(8):2387-2392 (2006).

Hinton, Paul R. et al., "An Engineered Human IgG1 Antibody wtih Longer Serum Half-Life," The Journal of Immunology, vol. 176:346-356 (2006).

Hobbs, J.R. et al., "A Half-molecule GK Plasmacytoma," Clin. exp. Immunol., vol. 5:199-207 (1969).

Hobbs, J.R., "Immunocytoma o' Mice an' Men," British Medical Journal, vol. 2:67-72 (1971).

Holliger< Philipp et al., "Engineered antibody fragments and the rise of single domains," Nature Biotechnology, vol. 23(9):1126-1136 (2005).

Horgan, Carol et al., "Studies on Antigen Binding by Intact and Hinge-Deleted Chimeric Antibodies," The Journal of Immunology, vol. 150(12):5400-5407 (1993).

Igarashi, Takako et al., "Structure of a Mouse Immunoglobulin G That Lacks the Entire CH1 Domain: Protein Sequencing and Small-Angle X-ray Scattering Studies," Biochemistry, vol. 29:5727-5733 (1990).

Jefferis, Roy et al., "IgG-Fc-mediated effector functions: molecular definition of interaction sites for effector ligands and the role of glycosylation," Immunological Reviews, vol. 163:59-76 (1998).

Kanamaru, Yutaka et al., "IgA Fc receptor I signals apoptosis through the FcRg ITAM and affects tumor growth," Blood, vol. 109(1):203-211 (2007).

Kawai, Tadashi et al., "Identification and Quantification of Half-Molecule Immunoglobulins," Annals Academy of Medicine Singapore, vol. 9(1):50-53 (1980).

Klein, Michel et al., "Expression of biological effector functions by immunoglobulin G molecules lacking the hinge region," Proc. Natl. Acad. Sci. USA, vol. 78(1):524-528 (1981).

Larson, Steven B. et al., "The Structure of an Antitumor CH2-domain-deleted Humanized Antibody," J. Mol. Biol., vol. 348:1177-1190 (2005).

Magnusson, Carl G.M. et al., "Human IgG is Substrate for the Thioredoxin System: Differential Cleavage Pattern of Interchain Disulfide Bridges in IgG Subclasses," Molecular Immunology, vol. 34(10):709-717 (1997).

Mushinski, J. Frederic, "gA Half Molecules: Defective Heavy Chain Mutants in Mouse Myeloma Proteins," The Journal of Immunology, vol. 106(1):41-50 (1971).

Mushinski, J. Frederic et al., "IgA Half Molecules. II. Genetic Variants of IgA Detected in Normal Mouse Intestinal Contents," The Journal of Immunology, vol. 177(5, Part 1):1668-1675 (1976).

Parham, Peter, "On the Fragmentation of Monoclonal IgG1, IgG2a, and IgG2b from BALB/c Mice," The Journal of Immunology, vol. 131(6):2895-2902 (1983).

Petkova, Stefka B. et al., "Enhanced half-life of genetically engineered human IgG1 antibodies in a humanized FcRn mouse model: potential application in humorally mediated autoimmune disease," International Immunology, vol. 18 (12):1759-1769 (2006).

Potter, M. et al., "Disorders in the Differentiation of Protein Secretion in Neoplastic Plasma Cells," J. Mol. Biol., vol. 9:537-544 (1964).

Rajan, S.S. et al., "Three-dimensional Structure of the Mcg IgG1 Immunoglobulin," Molecular Immunology, vol. 20 (7):787-799 (1983).

Robinson, Elizabeth A. et al., "Chemical Characterization of a Mouse Immunoglobulin A Heavy Chain with a 100-Residue Deletion," The Journal of Biological Chemistry, vol. 249(20):6605-6610 (1974).

Sakurabayashi, Ikunosuke et al., "Human IgA1 Half-Molecules: Clinical and Immunologic Features in a Patient With Multiple Myeloma," Blood, vol. 53:269-278 (1979).

Saphire, Erica Ollmann et al., "Contrasting IgG Structures Reveal Extreme Asymmetry and Flexibility," J. Mol. Biol., vol. 319:9-18 (2002).

Sarma, R. et al., "The Three-Dimensional Structure of a Human IgG1 Immunoglobulin at 4 A Resolution: A Computer Fit of Various Structural Domains on the Electron Density Map," J. Appl. Cryst., vol. 15:476-481 (1982).

Satoh, Mitsuo et al., "Non-fucosylated therapeutic antibodies as next-generation therapeutic antibodies," Expert Opin. Biol. Ther., vol. 6(11):1161-1173 (2006).

Schuster, Manfred et al., "Improved Effector Functions of a Therapeutic Monoclonal Lewis Y-Specific Antibody by Glycoform Engineering," Cancer Research, vol. 65(17):7934-7941 (2005).

Schuurman, Janine et al., "The inter-heavy chain disulfide bonds of IgG4 are in equilibrium with intra-chain disulfide bonds," Molecular Immunology, vol. 38:1-8 (2001).

Seligmann, M. et al., "Immunochemical Study of a Human Myeloma IgG1 Half Molecule," Ann. Immunol. (Inst. Pasteur), vol. 129:855-870 (1978).

Sheridan, Cormac, "Pharma consolidates its grip on post-antibody landscape," Nature Biotechnology, vol. 25 (4):365-366 (2007.

Shields, Robert L. et al., "High Resolution Mapping of the Binding Site on Human IgG1 for FcgRI, FcgRII, FcgRIII, and FcRn and Design of IgG1 Variants with Improved Binding to the FcgR," The Journal of Biological Chemistry, vol. 276(9):6591-6604 (2001).

Silverton, E.W. et al., "Three-dimensional structure of an intact human immunoglobulin," Proc. Natl. Acad. Sci. USA, vol. 74(11):5140-5144 (1977).

Spiegelberg, Hans L. et al., "Human Myeloma IgA Half-Molecules," The Journal of Clinical Investigation, vol. 58:1259-1265 (1976).

Spiegelberg, Hans L. et al., "Human Myeloma IgG Half-Molecules. Structural and Antigenic Analyses," Biochemistry, vol. 14(10):2157-2163 (1975).

Spiegelberg, Hans L., "Human Myeloma IgG Half-Molecules. Catabolism and Biological Properties," The Journal of Clinical Investigation, vol. 56:588-594 (1975).

Spiegelberg, Hans L. et al., "IgG Half-Molecules: Clinical and Immunologic Features in a Patient With Plasma Cell Leukemia," Blood, vol. 45(3):305-313 (1975).

Steiner, Lisa A. et al., "Amino Acid Sequence of the Heavy-Chain Variable Region of the Crystallizable Human Myeloma Protein Dob," Biochemistry, vol. 18(19):4068-4080 (1979).

Stevenson, George T. et al., "Conjugation of Human Fcg in Closed-Hinge or Open-Hinge Configuration to Fab'g and Analogous Ligands," The Journal of Immunology, vol. 158:2242-2250 (1997).

Watts, H.F. et al., "Activation of Complement Pathways by Univalent Antibody Derivatives with Intact Fc Zones," Molecular Immunology, vol. 22(7):803-810 (1985).

Zack, Donald J. et al., "Somatically Generated Mouse Myeloma Variants Synthesizing IgA Half-Molecules," J. Exp. Med., vol. 154:1554-1569 (1981).

(56) References Cited

OTHER PUBLICATIONS

International Preliminary Report on Patentability for Application No. PCT/DK2008/050127, dated Dec. 1, 2009.
Genmab, "Building for a Commercial Future. Reseasrch, Development and Business Update," PowerPoint Slideshow (2006).
U.S. Appl. No. 12/602,404, Janine Schuurman, filed Jul. 15, 2010, Mar. 16, 2015.
U.S. Appl. No. 13/132,423, Aran Frank Labrijn, filed Aug. 16, 2011, Mar. 16, 2015.
U.S. Appl. No. 13/132,423, Aran Frank Labrijn, filed Aug. 16, 2011, Oct. 29, 2014.
U.S. Appl. No. 12/602,404, filed Jul. 15, 2010, Janine Schuurman.
U.S. Appl. No. 12/095,023, filed Aug. 26, 2008, Paul Parren.
U.S. Appl. No. 13/132,423, filed Aug. 16, 2011, Aran Frank Labrijn.
U.S. Appl. No. 12/602,404, Jul. 15, 2014.
U.S. Appl. No. 12/602,404, Apr. 18, 2013.
U.S. Appl. No. 12/602,404, Sep. 13, 2012.
U.S. Appl. No. 12/602,404, Apr. 25, 2012.
U.S. Appl. No. 12/095,023, Jul. 15, 2014.
U.S. Appl. No. 12/095,023, Dec. 18, 2013.
U.S. Appl. No. 12/095,023, May 22, 2013.
U.S. Appl. No. 12/095,023, Jan. 26, 2012.
U.S. Appl. No. 12/095,023, Jul. 18, 2011.
U.S. Appl. No. 12/095,023, May 19, 2010.
U.S. Appl. No. 13/132,423, Mar. 1, 2013.
U.S. Appl. No. 13/132,423, Jul. 26, 2013.
U.S. Appl. No. 13/132,423, Apr. 2, 2014.

* cited by examiner hinge region

WT IgG4        KPSNTKVDKRVESKYGPPCPSCPAPEFLGGPS hingeless IgG4    KPSNTKVDKRVAPEFLGGPS CDC Daudi - evaluation heat inactivated serum

FIGURE 18

| Seq ID No | Name | | Oligo Sequence |
|---|---|---|---|
| 22 | VLexbetv1rev | P1 | AGCCACCGTACGTTTGATTTCCAGCTTGGTGCCTCC |
| 23 | VLex betv1for | P2 | GATGCAAGCTTGCCGCCACCATGGAGTCACAGATTCAGGCATTT |
| 24 | VHexbetv1rev | P3 | CGATGGGCCCTTGGTGCTGGCTGAGGAGACGGTGACTGAGGT |
| 25 | VHexbetv1for | P4 | GATGCAAGCTTGCCGCCACCATGAAATGCAGCTGGGTTATCTTC |
| 26 | LCseq3 | P5 | TGTACTTTGGCCTCTCTGGGATA |
| 27 | 7D8VLexrev | P6 | CTGGAGATTAAACGTACGGTGGCTGCACC |
| 28 | 7D8VLexfor | P7 | GCGACTAAGCTTGCCGCCACCATGGAAGCCCCAGCTCAGCTTCTC |
| 29 | 7D8VHexfor | P8 | GCTGAAAGCTTGCCGCCACCATGGAGTTGGGACTGAGCTGGATT |
| 30 | pConKseq1 | P9 | GTAGTCTGAGCAGTACTCGTTGC |
| 31 | pConG1seq1 | P10 | GAAGACTTAAGGCAGCGGCAGAA |
| 32 | HCseq5 | P11 | GGTCAGGGCGCCTGAGTTCCACG |
| 33 | HCseq11 | P12 | ATGCAGGCTACTCTAGGGCACCT |
| 34 | 2f8HCexrev | P13 | GAAGACCGATGGGCCCTTGGTGCTAGCTGAGGAGAC |
| 35 | IGG4gene2r | P14 | TGAGAATTCGGTGGGTGCTTTATTTCCATGCT |
| 36 | IGG4gene2f | P15 | GTAGAAGCTTACCATCGCGGATAGACAAGAACC |
| 37 | IGG4S228Pf | P16 | GGTCCCCCATGCCCACCATGCCCGGGTAAGCCA |
| 38 | IGG4S228Pr | P17 | TGGCTTACCCGGGCATGGTGGGCATGGGGGACC |
| 39 | RACEKmm1 | P18 | TGTTAACTGCTCACTGGATGGTGGGA |
| 40 | RACEG1mm1 | P19 | TCCCTGGGCACAATTTTCTTGTCCACC |
| 41 | ShortUPMH3 | P20 | TGAAAGCTTCTAATACGACTCACTATAGGGC |
| 42 | LongUPMH3 | P21 | TGAAAGCTTCTAATACGACTCACTATAGGGCAAGCAGTGGTATCAACGCAGAGT |

FIGURE 19

| Seq ID No | Name | Length | Oligo Sequence |
|---|---|---|---|
| 43 | A77VHfor1 | 62 | TCTTCTTCCTGATGGCAGTGGTTACAGGGGTCAATTCAGAGGTCCAGCTGCAGCAGACTGGA |
| 44 | A77VHfor2 | 61 | GATAAGCTTGCCGCCACCATGAAATGCAGCTGGGTTATCTTCTTCCTGATGGCAGTGGTTA |
| 45 | A77VHrev | 45 | GGATGGGCCCTTGGTGCTGGCCGCAGAGACAGTGACCAGAGTCCC |
| 46 | A77VLfor1 | 64 | CCTCATGTCCCTGCTGTTCTGGGTATCTGGTACCTGTGGGGACGTTGTGATGACCCAGACTCCA |
| 47 | A77VLfor2 | 62 | ACGAAGCTTGCCGCCACCATGGAATCACAGACTCAGGTCCTCATGTCCCTGCTGTTCTGGGT |
| 48 | IgG4delfor | 44 | AACTCCCAATCTTCTCTCTGCAGCTCAAGGCGGGACAGGTGCCC |
| 49 | IgG4delrev | 44 | GGGCACCTGTCCCGCCTTGAGCTGCAGAGAGAAGATTGGGAGTT |
| 50 | RACEG1A1 | 22 | GGGAGTAGAGTCCTGAGGACTG |
| 51 | RACEKA1` | 22 | TATCCACCTTCCACTGTACTTT |
| 52 | 2f8HCexfor | 45 | CGATGGAAGCTTGCCGCCACCATGGAATTGGGGCTGAGCTGGGTT |
| 53 | 2f8HCexrev | 36 | GAAGACCGATGGGCCCTTGGTGCTAGCTGAGGAGAC |

FIGURE 25

| HIV-1 isolate | HuMax-CD4 starting conc (ug/ml) | Inhibition HuMax-CD4 IC50 (nM) | Fab fragments starting conc (ug/ml) | Inhibition Fab IC50 (nM) |
|---|---|---|---|---|
| YU2 | 10 | 9.9 | 30 | 119.9 |
| IIIB | 20 | 4.7 | 60 | 46.4 |
| ADA | 10 | 2.5 | 30 | 32.9 |
| 89.6 | 3 | 1.8 | 9 | 17.8 |
| US143 | 1 | 0.6 | 3 | 11.9 |
| JR-FL | 1 | 2.1 | 30 | 29.1 |
| JR-CSF | 1 | 0.3 | 30 | 9.5 |
| SF 162 | 1 | 0.6 | 30 | 6.3 |

FIGURE 26

Date of reconsitution: 8/11/03   Date of infection: 8/26/03   Date of single injection: 9/08/03

| Mouse number | Molecule i.p. | Genre | N. of cells (x106) | Vol. (ml) | % Hu cells | % Murine cells | % CD4 cells | % CD8 cells | CD4/CD8 | AVG | SD |
|---|---|---|---|---|---|---|---|---|---|---|---|
| 754 | 1mg Ig-CD4 | F | 1.5 | 7 | 0 | 5.61 | 0.03 | 0 | 0 | | |
| 757 | 1mg Ig-CD4 | F | 1 | 6 | 9.53 | 82.77 | 1.12 | 10.5 | 0.106 | | |
| 750 | 1mg Ig-CD4 | F | 2 | 7 | 22.25 | 69.45 | 1.82 | 20.8 | 0.08 | 0.1 | 0.01 |
| 759 | 1mg Ig-CD4 | M | 3 | 8 | 35.44 | 46.27 | 2.34 | 20.53 | 0.114 | | |
| 755 | 1mg Ig-cont | F | 2 | 6 | 86.29 | 10.03 | 2.46 | 84.87 | 0.028 | | |
| 746 | 1mg Ig-cont | F | 1 | 7 | 83.9 | 13.14 | 1.15 | 82.95 | 0.013 | 0.02 | 0.01 |
| 749 | 1mg Ig-cont | F | 3.2 | 8 | 86.48 | 10.76 | 1.69 | 86.08 | 0.019 | | |
| 756 | Non treated | F | 3 | 6 | 58.88 | 38.57 | 1.19 | 58.7 | 0.02 | | |
| 748 | Non treated | F | 4 | 7 | 95.52 | 2.44 | 0.82 | 96.3 | 0.008 | 0.04 | 0.04 |
| 758 | Non treated | M | 3 | 6 | 86.28 | 10.73 | 7.37 | 79.72 | 0.092 | | |
| 761 | Non infected | M | 4 | 8 | 80.85 | 17.39 | 22.94 | 53.77 | 0.426 | 0.48 | 0.06 |
| 762 | Non infected | M | 4 | 7 | 48.5 | 13.2 | 16.6 | 30.93 | 0.536 | | |

FIGURE 34
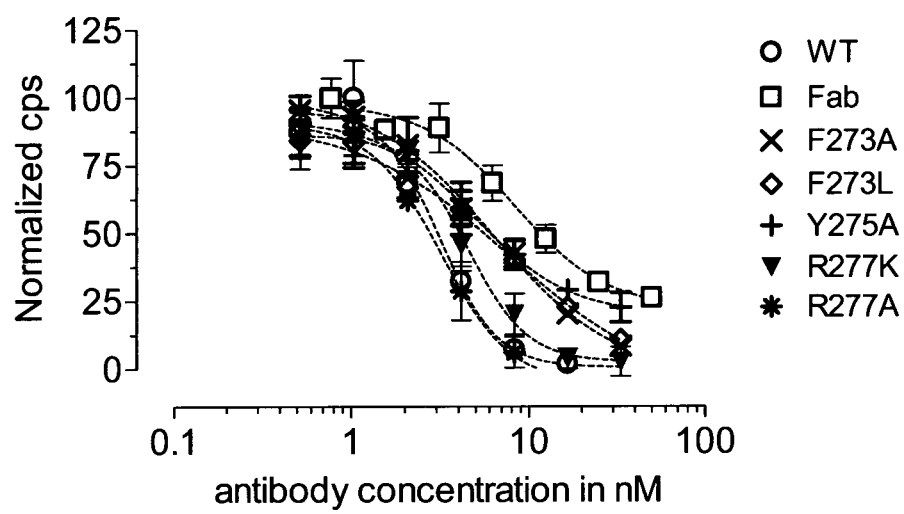
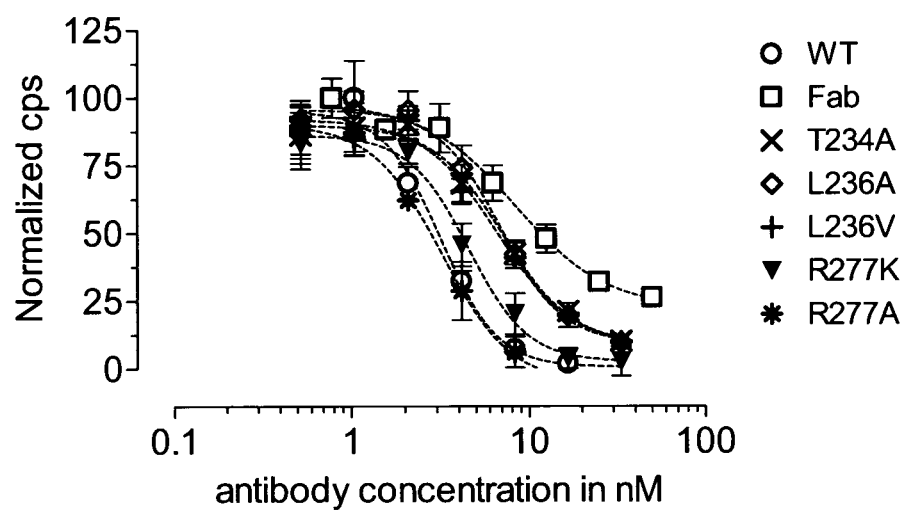

| Molecule | EC50 (µM) |
|---|---|
| WT | 0.039 |
| F273A | 3.059 |
| L236V | 2.155 |
| R277K | - |
| Y275A | 2.192 |

SEQUENCE LISTING

<160> NUMBER OF SEQ ID NOS: 56

<210> SEQ ID NO 1
<211> LENGTH: 321
<212> TYPE: DNA
<213> ORGANISM: Homo sapiens

<400> SEQUENCE: 1

```
cgtacggtgg ctgcaccatc tgtcttcatc ttcccgccat ctgatgagca gttgaaatct        60
ggaactgcct ctgttgtgtg cctgctgaat aacttctatc ccagagaggc caaagtacag       120
tggaaggtgg ataacgccct ccaatcgggt aactcccagg agagtgtcac agagcaggac       180
agcaaggaca gcacctacag cctcagcagc accctgacgc tgagcaaagc agactacgag       240
aaacacaaag tctacgcctg cgaagtcacc catcagggcc tgagctcgcc cgtcacaaag       300
agcttcaaca ggggagagtg t                                                 321
```

<210> SEQ ID NO 2
<211> LENGTH: 107
<212> TYPE: PRT
<213> ORGANISM: Homo sapiens

<400> SEQUENCE: 2

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 3
<211> LENGTH: 327
<212> TYPE: DNA
<213> ORGANISM: Homo sapiens

<400> SEQUENCE: 3

```
accgtcctag gtcagcccaa ggctgccccc tcggtcactc tgttcccgcc ctcctctgag      60
gagcttcaag ccaacaaggc cacactggtg tgtctcataa gtgacttcta cccgggagcc     120
gtgacagtgg cctggaaggc agatagcagc cccgtcaagg cgggagtgga gaccaccaca     180
ccctccaaac aaagcaacaa caagtacgcg gccagcagct acctgagcct gacgcctgag     240
cagtggaagt cccacagaag ctacagctgc caggtcacgc atgaagggag caccgtggag     300
aagacagtgg cccctacaga atgttca                                        327
```

<210> SEQ ID NO 4
<211> LENGTH: 109
<212> TYPE: PRT
<213> ORGANISM: Homo sapiens

<400> SEQUENCE: 4

```
Thr Val Leu Gly Gln Pro Lys Ala Ala Pro Ser Val Thr Leu Phe Pro
1               5                   10                  15

Pro Ser Ser Glu Glu Leu Gln Ala Asn Lys Ala Thr Leu Val Cys Leu
            20                  25                  30

Ile Ser Asp Phe Tyr Pro Gly Ala Val Thr Val Ala Trp Lys Ala Asp
        35                  40                  45

Ser Ser Pro Val Lys Ala Gly Val Glu Thr Thr Thr Pro Ser Lys Gln
    50                  55                  60

Ser Asn Asn Lys Tyr Ala Ala Ser Ser Tyr Leu Ser Leu Thr Pro Glu
65                  70                  75                  80

Gln Trp Lys Ser His Arg Ser Tyr Ser Cys Gln Val Thr His Glu Gly
                85                  90                  95

Ser Thr Val Glu Lys Thr Val Ala Pro Thr Glu Cys Ser
            100                 105
```

<210> SEQ ID NO 5
<211> LENGTH: 366
<212> TYPE: DNA
<213> ORGANISM: Homo sapiens

<400> SEQUENCE: 5

```
gaagtgcagc tggtggagtc tgggggaggc ttggtacagc ctgacaggtc cctgagactc      60
tcctgtgcag cctctggatt caccttcat gattatgcca tgcactgggt ccggcaagct     120
ccagggaagg gctggagtg gtctcaact attagttgga atagtggtac cataggctat     180
gcggactctg tgaagggccg attcaccatc tccagagaca acgccaagaa ctccctgtat     240
ctgcaaatga acagtctgag agctgaggac acggccttgt attactgtgc aaaagatata     300
cagtacggca actactacta cggtatggac gtctggggcc aagggaccac ggtcaccgtc     360
tcctca                                                              366
```

<210> SEQ ID NO 6
<211> LENGTH: 122
<212> TYPE: PRT
<213> ORGANISM: Homo sapiens

<400> SEQUENCE: 6

Glu Val Gln Leu Val Glu Ser Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
            115                 120

<210> SEQ ID NO 7
<211> LENGTH: 354
<212> TYPE: DNA
<213> ORGANISM: Mus musculus

<400> SEQUENCE: 7
gaggttcagc tgcagcagtc tggggcagag cttgtgaaac caggggcctc agtcaagttg      60
tcctgcacag cttctggctt caacattaaa gacacctata tccactgggt gaagcagagg     120
cctgaacagg gcctggagtg ggttggaagg attgatcctg cgactggcaa tactagatat     180 gaccccgaagt ccagggcaa ggccactata acagctgaca catcctccaa cacagcctac     240
ctgcaactca gcagcctgac atctgaggac actgccgtct attactgtgc tagttttagg     300
ccggggtatg ctctggacta ctggggtcaa ggaacctcag tcaccgtctc ctca            354

<210> SEQ ID NO 8
<211> LENGTH: 118
<212> TYPE: PRT
<213> ORGANISM: Mus musculus

<400> SEQUENCE: 8

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Val
        35                  40                  45

Gly Arg Ile Asp Pro Ala Thr Gly Asn Thr Arg Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Phe Arg Pro Gly Tyr Ala Leu Asp Tyr Trp Gly Gln Gly Thr
            100                 105                 110

Ser Val Thr Val Ser Ser
            115

<210> SEQ ID NO 9
<211> LENGTH: 321

```
<212> TYPE: DNA
<213> ORGANISM: Homo sapiens

<400> SEQUENCE: 9
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgatcac cttcggccaa   300
gggacacgac tggagattaa a                                              321

<210> SEQ ID NO 10
<211> LENGTH: 107
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Thr Phe Gly Gln Gly Thr Arg Leu Glu Ile Lys
            100                 105

<210> SEQ ID NO 11
<211> LENGTH: 321
<212> TYPE: DNA
<213> ORGANISM: Mus musculus

<400> SEQUENCE: 11
gacattgtga tgacccagtc tcacaaattc atgtccacat cagttggaga cagggtcagc    60
ttcacctgca aggccagtca ggatgtgttt actgctgtag cctggtatca acaaaaacca   120
gggcaatctc ctaaactact gatttactgg gcatccaccc ggcgcactgg agtccctgat   180
cgcttcacag gcagtggatc tgggacagat tatactctca ccatcagcag tgtgcaggct   240
gaagacctgg cactttatta ctgtcagcaa cattttagca ctcctccgac gttcggtgga   300
ggcaccaagc tggaaatcaa a                                              321

<210> SEQ ID NO 12
<211> LENGTH: 107
<212> TYPE: PRT
<213> ORGANISM: Mus musculus

<400> SEQUENCE: 12

Asp Ile Val Met Thr Gln Ser His Lys Phe Met Ser Thr Ser Val Gly
 1               5                  10                  15

Asp Arg Val Ser Phe Thr Cys Lys Ala Ser Gln Asp Val Phe Thr Ala
             20                  25                  30
```

Val Ala Trp Tyr Gln Gln Lys Pro Gly Gln Ser Pro Lys Leu Leu Ile
            35                  40                  45

Tyr Trp Ala Ser Thr Arg Arg Thr Gly Val Pro Asp Arg Phe Thr Gly
        50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Phe Ser Thr Pro Pro
                85                  90                  95

Thr Phe Gly Gly Gly Thr Lys Leu Glu Ile Lys
            100                 105

<210> SEQ ID NO 13
<211> LENGTH: 1588
<212> TYPE: DNA
<213> ORGANISM: Homo sapiens

<400> SEQUENCE: 13

| | | | | | |
|---|---|---|---|---|---|
| gctagcacca | agggcccatc | cgtcttcccc | ctggcgccct | gctccaggag | cacctccgag | 60 |
| agcacagccg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacgaagacc | 240 |
| tacacctgca | acgtagatca | caagcccagc | aacaccaagg | tggacaagag | agttggtgag | 300 |
| aggccagcac | agggagggag | ggtgtctgct | ggaagccagg | ctcagccctc | ctgcctggac | 360 |
| gcaccccggc | tgtgcagccc | cagcccaggg | cagcaaggca | tgccccatct | gtctcctcac | 420 |
| ccggaggcct | ctgaccaccc | cactcatgct | cagggagagg | tcttctgga | tttttccacc | 480 |
| aggctccggg | cagccacagg | ctggatgccc | taccccagg | ccctgcgcat | acaggggcag | 540 |
| gtgctgcgct | cagacctgcc | aagagccata | tccggaggga | ccctgcccct | gacctaagcc | 600 |
| cacccccaaag | gccaaactct | ccactcccctc | agctcagaca | ccttctctcc | tcccagatct | 660 |
| gagtaactcc | caatcttctc | tctgcagagt | ccaaatatgg | tcccccatgc | ccatcatgcc | 720 |
| caggtaagcc | aacccaggcc | tcgccctcca | gctcaaggcg | ggacaggtgc | cctagagtag | 780 |
| cctgcatcca | gggacaggcc | ccagccgggt | gctgacgcat | ccacctccat | ctcttcctca | 840 |
| gcacctgagt | tcctgggggg | accatcagtc | ttcctgttcc | ccccaaaacc | caaggacact | 900 |
| ctcatgatct | cccggaccccc | tgaggtcacg | tgcgtggtgg | tggacgtgag | ccaggaagac | 960 |
| cccgaggtcc | agttcaactg | gtacgtggat | ggcgtggagg | tgcataatgc | caagacaaag | 1020 |
| ccgcgggagg | agcagttcaa | cagcacgtac | cgtgtggtca | gcgtcctcac | cgtcctgcac | 1080 |
| caggactggc | tgaacggcaa | ggagtacaag | tgcaaggtct | ccaacaaagg | cctcccgtcc | 1140 |
| tccatcgaga | aaaccatctc | caaagccaaa | ggtgggaccc | acggggtgcg | agggccacat | 1200 |
| ggacagaggt | cagctcggcc | caccctctgc | cctgggagtg | accgctgtgc | caacctctgt | 1260 |
| ccctacaggg | cagccccgag | agccacaggt | gtacaccctg | cccccatccc | aggaggagat | 1320 |
| gaccaagaac | caggtcagcc | tgacctgcct | ggtcaaaggc | ttctacccca | gcgacatcgc | 1380 |
| cgtggagtgg | gagagcaatg | ggcagccgga | gaacaactac | aagaccacgc | ctcccgtgct | 1440 |
| ggactccgac | ggctccttct | tcctctacag | caggctaacc | gtggacaaga | gcaggtggca | 1500 |
| ggagggaat | gtcttctcat | gctccgtgat | gcatgaggct | ctgcacaacc | actacacaca | 1560 |
| gaagagcctc | tccctgtctc | tgggtaaa | | | | 1588 |

```
<210> SEQ ID NO 14
<211> LENGTH: 327
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 15
<211> LENGTH: 1588
<212> TYPE: DNA
<213> ORGANISM: Homo sapiens

<400> SEQUENCE: 15
gctagcacca agggcccatc cgtcttcccc ctggcgccct gctccaggag cacctccgag    60
```

```
agcacagccg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacgaagacc      240
tacacctgca acgtagatca caagcccagc aacaccaagg tggacaagag agttggtgag      300
aggccagcac agggagggag ggtgtctgct ggaagccagg ctcagccctc ctgcctggac      360
gcaccccggc tgtgcagccc cagcccaggg cagcaaggca tgccccatct gtctcctcac      420
ccggaggcct ctgaccaccc cactcatgct cagggagagg gtcttctgga ttttccacc      480 aggctccggg cagccacagg ctggatgccc tacccccagg ccctgcgcat acaggggcag      540
gtgctgcgct cagacctgcc aagagccata tccggagga ccctgcccct gacctaagcc      600 cacccccaaag gccaaactct ccactccctc agctcagaca ccttctctcc tcccagatct      660
gagtaactcc caatcttctc tctgcagagt ccaaatatgg tccccatgc ccaccatgcc      720 cgggtaagcc aacccaggcc tcgccctcca gctcaaggcg ggacaggtgc cctagagtag      780
cctgcatcca gggacaggcc ccagccgggt gctgacgcat ccacctccat ctcttcctca      840
gcacctgagt tcctgggggg accatcagtc ttcctgttcc ccccaaaacc caaggacact      900
ctcatgatct cccggacccc tgaggtcacg tgcgtggtgg tggacgtgag ccaggaagac      960
cccgaggtcc agttcaactg gtacgtggat ggcgtggagg tgcataatgc caagacaaag     1020
ccgcgggagg agcagttcaa cagcacgtac cgtgtggtca gcgtcctcac cgtcctgcac     1080
caggactggc tgaacggcaa ggagtacaag tgcaaggtct ccaacaaagg cctcccgtcc     1140
tccatcgaga aaaccatctc caaagccaaa ggtgggaccc acggggtgcg agggccacat     1200
ggacagaggt cagctcggcc cacccctctgc cctgggagtg accgctgtgc caacctctgt     1260
ccctacaggg cagccccgag agccacaggt gtacaccctg cccccatccc aggagagat     1320 gaccaagaac caggtcagcc tgacctgcct ggtcaaaggc ttctacccca gcgacatcgc     1380
cgtggagtgg gagagcaatg ggcagccgga gaacaactac aagaccacgc ctcccgtgct     1440
ggactccgac ggctccttct tcctctacag caggctaacc gtggacaaga gcaggtggca     1500 ggagggaat gtcttctcat gctccgtgat gcatgaggct ctgcacaacc actacacaca     1560
gaagagcctc tccctgtctc tgggtaaa                                        1588
```

<210> SEQ ID NO 16
<211> LENGTH: 315
<212> TYPE: PRT
<213> ORGANISM: Homo sapiens

<400> SEQUENCE: 16

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

Arg Val Ala Pro Glu Phe Leu Gly Gly Pro Ser Val Phe Leu Phe Pro
                100                 105                 110

Pro Lys Pro Lys Asp Thr Leu Met Ile Ser Arg Thr Pro Glu Val Thr
            115                 120                 125

Cys Val Val Val Asp Val Ser Gln Glu Asp Pro Glu Val Gln Phe Asn
        130                 135                 140

Trp Tyr Val Asp Gly Val Glu Val His Asn Ala Lys Thr Lys Pro Arg
145                 150                 155                 160

Glu Glu Gln Phe Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Gly Leu Pro Ser Ser Ile Glu Lys Thr Ile Ser Lys Ala Lys
        195                 200                 205

Gly Gln Pro Arg Glu Pro Gln Val Tyr Thr Leu Pro Pro Ser Gln Glu
    210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
                245                 250                 255

Asn Asn Tyr Lys Thr Thr Pro Pro Val Leu Asp Ser Asp Gly Ser Phe
            260                 265                 270

Phe Leu Tyr Ser Arg Leu Thr Val Asp Lys Ser Arg Trp Gln Glu Gly
        275                 280                 285

Asn Val Phe Ser Cys Ser Val Met His Glu Ala Leu His Asn His Tyr
    290                 295                 300

Thr Gln Lys Ser Leu Ser Leu Ser Leu Gly Lys
305                 310                 315

<210> SEQ ID NO 17
<211> LENGTH: 105
<212> TYPE: PRT
<213> ORGANISM: Homo sapiens

<400> SEQUENCE: 17

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 18
<211> LENGTH: 106
<212> TYPE: PRT
<213> ORGANISM: Homo sapiens

<400> SEQUENCE: 18

```
Thr Val Ala Ala Pro Ser Val Phe Ile Phe Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu

Ser Leu Ser Pro Gly Lys
                325

<210> SEQ ID NO 21
<211> LENGTH: 377
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375

<210> SEQ ID NO 22
<211> LENGTH: 36
<212> TYPE: DNA
<213> ORGANISM: artificial
<220> FEATURE:
<223> OTHER INFORMATION: primer

<400> SEQUENCE: 22
agccaccgta cgtttgattt ccagcttggt gcctcc                                36

<210> SEQ ID NO 23
<211> LENGTH: 44
<212> TYPE: DNA
<213> ORGANISM: artificial
<220> FEATURE:
<223> OTHER INFORMATION: primer

<400> SEQUENCE: 23
gatgcaagct tgccgccacc atggagtcac agattcaggc attt                       44

<210> SEQ ID NO 24
<211> LENGTH: 42
<212> TYPE: DNA
<213> ORGANISM: artificial
<220> FEATURE:
<223> OTHER INFORMATION: primer

<400> SEQUENCE: 24
cgatgggccc ttggtgctgg ctgaggagac ggtgactgag gt                         42

<210> SEQ ID NO 25
<211> LENGTH: 44
<212> TYPE: DNA
<213> ORGANISM: artificial
<220> FEATURE:
<223> OTHER INFORMATION: primer

<400> SEQUENCE: 25
gatgcaagct tgccgccacc atgaaatgca gctgggttat cttc                       44

<210> SEQ ID NO 26
<211> LENGTH: 23
<212> TYPE: DNA
<213> ORGANISM: artificial
<220> FEATURE:
<223> OTHER INFORMATION: primer

<400> SEQUENCE: 26
tgtactttgg cctctctggg ata                                              23

<210> SEQ ID NO 27
<211> LENGTH: 29
<212> TYPE: DNA
<213> ORGANISM: artificial
<220> FEATURE:
<223> OTHER INFORMATION: primer

<400> SEQUENCE: 27
ctggagatta aacgtacggt ggctgcacc                                        29

```
<210> SEQ ID NO 28
<211> LENGTH: 45
<212> TYPE: DNA
<213> ORGANISM: artificial
<220> FEATURE:
<223> OTHER INFORMATION: primer

<400> SEQUENCE: 28
gcgactaagc ttgccgccac catggaagcc ccagctcagc ttctc            45

<210> SEQ ID NO 29
<211> LENGTH: 44
<212> TYPE: DNA
<213> ORGANISM: artificial
<220> FEATURE:
<223> OTHER INFORMATION: primer

<400> SEQUENCE: 29
gctgaaagct tgccgccacc atggagttgg gactgagctg gatt             44

<210> SEQ ID NO 30
<211> LENGTH: 23
<212> TYPE: DNA
<213> ORGANISM: artificial
<220> FEATURE:
<223> OTHER INFORMATION: primer

<400> SEQUENCE: 30
gtagtctgag cagtactcgt tgc                                    23

<210> SEQ ID NO 31
<211> LENGTH: 23
<212> TYPE: DNA
<213> ORGANISM: artificial
<220> FEATURE:
<223> OTHER INFORMATION: primer

<400> SEQUENCE: 31
gaagacttaa ggcagcggca gaa                                    23

<210> SEQ ID NO 32
<211> LENGTH: 23
<212> TYPE: DNA
<213> ORGANISM: artificial
<220> FEATURE:
<223> OTHER INFORMATION: primer

<400> SEQUENCE: 32
ggtcagggcg cctgagttcc acg                                    23

<210> SEQ ID NO 33
<211> LENGTH: 23
<212> TYPE: DNA
<213> ORGANISM: artificial
<220> FEATURE:
<223> OTHER INFORMATION: primer

<400> SEQUENCE: 33
atgcaggcta ctctagggca cct                                    23

<210> SEQ ID NO 34
<211> LENGTH: 36
<212> TYPE: DNA
<213> ORGANISM: artificial
<220> FEATURE:
<223> OTHER INFORMATION: primer
```

<400> SEQUENCE: 34
gaagaccgat gggcccttgg tgctagctga ggagac         36

<210> SEQ ID NO 35
<211> LENGTH: 32
<212> TYPE: DNA
<213> ORGANISM: artificial
<220> FEATURE:
<223> OTHER INFORMATION: primer

<400> SEQUENCE: 35
tgagaattcg gtgggtgctt tatttccatg ct         32

<210> SEQ ID NO 36
<211> LENGTH: 33
<212> TYPE: DNA
<213> ORGANISM: artificial
<220> FEATURE:
<223> OTHER INFORMATION: primer

<400> SEQUENCE: 36
gtagaagctt accatcgcgg atagacaaga acc         33

<210> SEQ ID NO 37
<211> LENGTH: 33
<212> TYPE: DNA
<213> ORGANISM: artificial
<220> FEATURE:
<223> OTHER INFORMATION: primer

<400> SEQUENCE: 37
ggtcccccat gcccaccatg cccgggtaag cca         33

<210> SEQ ID NO 38
<211> LENGTH: 33
<212> TYPE: DNA
<213> ORGANISM: artificial
<220> FEATURE:
<223> OTHER INFORMATION: primer

<400> SEQUENCE: 38
tggcttaccc gggcatggtg ggcatggggg acc         33

<210> SEQ ID NO 39
<211> LENGTH: 26
<212> TYPE: DNA
<213> ORGANISM: artificial
<220> FEATURE:
<223> OTHER INFORMATION: primer

<400> SEQUENCE: 39
tgttaactgc tcactggatg gtggga         26

<210> SEQ ID NO 40
<211> LENGTH: 27
<212> TYPE: DNA
<213> ORGANISM: artificial
<220> FEATURE:
<223> OTHER INFORMATION: primer

<400> SEQUENCE: 40
tccctgggca caatttttctt gtccacc         27

<210> SEQ ID NO 41
<211> LENGTH: 31

```
<212> TYPE: DNA
<213> ORGANISM: artificial
<220> FEATURE:
<223> OTHER INFORMATION: primer

<400> SEQUENCE: 41
tgaaagcttc taatacgact cactataggg c                              31

<210> SEQ ID NO 42
<211> LENGTH: 54
<212> TYPE: DNA
<213> ORGANISM: artificial
<220> FEATURE:
<223> OTHER INFORMATION: primer

<400> SEQUENCE: 42
tgaaagcttc taatacgact cactataggg caagcagtgg tatcaacgca gagt     54

<210> SEQ ID NO 43
<211> LENGTH: 62
<212> TYPE: DNA
<213> ORGANISM: artificial
<220> FEATURE:
<223> OTHER INFORMATION: primer

<400> SEQUENCE: 43
tcttcttcct gatggcagtg gttacagggg tcaattcaga ggtccagctg cagcagactg    60
ga                                                              62

<210> SEQ ID NO 44
<211> LENGTH: 61
<212> TYPE: DNA
<213> ORGANISM: artificial
<220> FEATURE:
<223> OTHER INFORMATION: primer

<400> SEQUENCE: 44
gataagcttg ccgccaccat gaaatgcagc tgggttatct tcttcctgat ggcagtggtt    60
a                                                               61

<210> SEQ ID NO 45
<211> LENGTH: 45
<212> TYPE: DNA
<213> ORGANISM: artificial
<220> FEATURE:
<223> OTHER INFORMATION: primer

<400> SEQUENCE: 45
ggatgggccc ttggtgctgg ccgcagagac agtgaccaga gtccc                45

<210> SEQ ID NO 46
<211> LENGTH: 64
<212> TYPE: DNA
<213> ORGANISM: artificial
<220> FEATURE:
<223> OTHER INFORMATION: primer

<400> SEQUENCE: 46
cctcatgtcc ctgctgttct gggtatctgg tacctgtggg acgttgtga tgacccagac    60 tcca                                                            64

<210> SEQ ID NO 47
<211> LENGTH: 62
<212> TYPE: DNA
```

-continued

<213> ORGANISM: artificial
<220> FEATURE:
<223> OTHER INFORMATION: primer

<400> SEQUENCE: 47
acgaagcttg ccgccaccat ggaatcacag actcaggtcc tcatgtccct gctgttctgg    60
gt                                                                  62

<210> SEQ ID NO 48
<211> LENGTH: 44
<212> TYPE: DNA
<213> ORGANISM: artificial
<220> FEATURE:
<223> OTHER INFORMATION: primer

<400> SEQUENCE: 48
aactcccaat cttctctctg cagctcaagg cgggacaggt gccc                    44

<210> SEQ ID NO 49
<211> LENGTH: 44
<212> TYPE: DNA
<213> ORGANISM: artificial
<220> FEATURE:
<223> OTHER INFORMATION: primer

<400> SEQUENCE: 49
gggcacctgt cccgccttga gctgcagaga gaagattggg agtt                    44

<210> SEQ ID NO 50
<211> LENGTH: 22
<212> TYPE: DNA
<213> ORGANISM: artificial
<220> FEATURE:
<223> OTHER INFORMATION: primer

<400> SEQUENCE: 50
gggagtagag tcctgaggac tg                                            22

<210> SEQ ID NO 51
<211> LENGTH: 22
<212> TYPE: DNA
<213> ORGANISM: artificial
<220> FEATURE:
<223> OTHER INFORMATION: primer

<400> SEQUENCE: 51
tatccacctt ccactgtact tt                                            22

<210> SEQ ID NO 52
<211> LENGTH: 45
<212> TYPE: DNA
<213> ORGANISM: artificial
<220> FEATURE:
<223> OTHER INFORMATION: primer

<400> SEQUENCE: 52
cgatggaagc ttgccgccac catggaattg gggctgagct gggtt                   45

<210> SEQ ID NO 53
<211> LENGTH: 36
<212> TYPE: DNA
<213> ORGANISM: artificial
<220> FEATURE:
<223> OTHER INFORMATION: primer

<400> SEQUENCE: 53

```
gaagaccgat gggcccttgg tgctagctga ggagac                              36
```

<210> SEQ ID NO 54
<211> LENGTH: 19
<212> TYPE: PRT
<213> ORGANISM: artificial
<220> FEATURE:
<223> OTHER INFORMATION: synthetic peptide

<400> SEQUENCE: 54

```
Val Ala Pro Glu Phe Leu Gly Gly Pro Ser Val Phe Leu Phe Pro Pro
1               5                   10                  15

Lys Pro Lys
```

<210> SEQ ID NO 55
<211> LENGTH: 32
<212> TYPE: PRT
<213> ORGANISM: homo sapiens

<400> SEQUENCE: 55

```
Lys Pro Ser Asn Thr Lys Val Asp Lys Arg Val Glu Ser Lys Tyr Gly
1               5                   10                  15

Pro Pro Cys Pro Ser Cys Pro Ala Pro Glu Phe Leu Gly Gly Pro Ser
                20                  25                  30
```

<210> SEQ ID NO 56
<211> LENGTH: 20
<212> TYPE: PRT
<213> ORGANISM: artificial
<220> FEATURE:
<223> OTHER INFORMATION: synthetic peptide

<400> SEQUENCE: 56

```
Lys Pro Ser Asn Thr Lys Val Asp Lys Arg Val Ala Pro Glu Phe Leu
1               5                   10                  15

Gly Gly Pro Ser
            20
```

RECOMBINANT IGG4 MONOVALENT ANTIBODIES

All patents, pending patent applications and other publications cited herein are hereby incorporated by reference in their entirety.

FIELD OF INVENTION

The present invention relates to novel non-human transgenic animals, which upon antigenic stimulation are capable of producing monovalent antibodies binding to a selected antigen, modified heavy chain transgenes, methods for producing the non-human transgenic animals, methods for immunizing the non-human transgenic animals for as well as monovalent antibodies obtainable by such immunization methods.

BACKGROUND OF THE INVENTION

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each light chain is comprised of a light chain variable region (abbreviated herein as $V_L$) and a light chain constant region (abbreviated herein as $C_L$). Each heavy chain is comprised of a heavy chain variable region ($V_H$) and a heavy chain constant region ($C_H$) consisting of three domain, $C_H1$, $C_H2$ and $C_H3$). $C_H1$ and $C_H2$ of the heavy chain are separated from each other by the so-called hinge region. The hinge region normally comprises one or more cysteine residues, which may form disulphide bridges with the cysteine residues of the hinge region of the other heavy chain in the antibody molecule.

Recently, antibodies have become a major focus area for therapeutic applications, and many antibody drug products have been approved or are in the process of being approved for use as therapeutic drugs. The desired characteristics of therapeutic antibodies may vary according to the specific condition which is to be treated. For some indications, only antigen binding is required, for instance where the therapeutic effect of the antibody is to block interaction between the antigen and one or more specific molecules otherwise capable of binding to the antigen. For such indications, the use of Fab fragments, the only function of which is to bind antigen, may be preferred. For other indications, further effects may also be required, such as for instance the ability to induce complement activation and/or the ability to for instance bind Fc receptors, protect from catabolism, recruit immune required. Some full-length antibodies may exhibit agonistic effects (which may be considered to be undesirable) upon binding to the target antigen, even though the antibody works as an antagonist when used as a Fab fragment. In some instances, this effect may be attributed to "cross-linking" of the bivalent antibodies, which in turn promotes target dimerization, which may lead to activation, especially when the target is a receptor. In the case of soluble antigens, dimerization may form undesirable immune complexes.

In some cases, monovalent binding to an antigen, such as in the case of FcαRI may induce apoptotic signals (Kanamura et al, Blood published on line Sep. 25, 2006))

For some indications, monovalent antibodies may thus be preferable. The presently available Fab fragments show inferior pharmacokinetics due to their small size resulting to filtration in the kidneys as well as their inability to interact with the Brambell receptor FcRn (Junghans R P et al., Proc Natl Acad Sci USA 93(11), 5512-6 (1996)), therefore being unstable in vivo and having very rapid clearance after administration.

Dimeric, monovalent antibodies (Fab/c), wherein the Fc region comprises two Fc polypeptides, have also been described (WO200563816 to Genentech and Parham P, J Immunol. 131(6), 2895-902 (1983)).

There is thus a need for stable monovalent antibodies for use as therapeutics.

Deletion of one or more of the domains of full-length antibodies, covering for instance regions comprising amino acid residues necessary for forming disulphide bridges or providing non-covalent inter-heavy chain contacts in the antibody may be a way of constructing monovalent antibodies.

Igarashi et al. (Igarashi, T M. et al., Biochemistry 29, 5727 (1990)) have described the structure of a mouse IgG2a molecule in which the entire $C_H1$ domain was deleted, but the hinge region was intact. The $C_H1$ deleted antibody is shown to exist as an elongated structure with a relatively small hinge angle. The molecule however retained the regular tetrameric configuration consisting of two light chains and two heavy chains expected for IgGs, and was thus still bivalent, and the $C_H1$ deletion did not affect the affinity of the mutated antibody.

Larson et al. (Larson, S B. et al., J Mol Biol 348, 1177 (2005)) have described the structure of a humanized IgG1 antibody in which the $C_H2$ domain has been deleted. Such antibody exists in two molecular forms, termed form A and form B. Form A contains two inter-chain disulphide bonds in the hinge, whereas form B does not contain inter-chain disulphide bonds. Form B exists as ~122 kDa molecule which seems to be held together by non-covalent interactions within the $C_H3$ domain. The antibody displays rapid serum clearance because of an inability to bind and recycle through FcRn receptors.

Ig half-molecules, which have a dimeric configuration consisting of only one light chain and only one heavy chain, have been described as the result of rare deletions in human and murine plasmacytomas. Several patients suffering from extramedullary soft-tissue plasmacytoma, Waldenström macroglobulinemia, plasma cell leukemia and multiple myeloma, excreted IgG half molecules into their urine. Half-molecules were also found to be present in their serum. Studies on the biochemical nature of these half-molecules showed that they consist of IgG1 molecules in which the heavy chain $C_H1$, hinge and $C_H2$ regions appeared normal, whereas deletions were found in the $C_H3$ region. The deletion on the $C_H3$ constant domain in the IgG1 half-molecule analyzed by Spiegelberg was shown to encompass 5,000-8,000 dalton and the hinge peptide sequence was identical to wild type IgG1. The mutations appeared to be located in $C_H3$ and the hinge peptide appeared normal (Hobbs, J R et al., Clin Exp Immunol 5, 199 (1969); Hobbs, J R, Br Med J 2, 67 (1971); Spiegelberg, H L et al., Blood 45, 305 (1975); Spiegelberg, H L et al., Biochemistry 14, 2157 (1975); Seligmann M E et al., Ann Immunol (Paris) 129C, 855-870 (1978); Gallango, M L et al., Blut 48, 91 (1983)). It was also showed that this human IgG1 half-molecule is rapidly catabolized (half-life in man was 4.3 days) and, in monomeric form, is unable to bind C1q or Fc receptors on human lymphocytes, monocytes or neutrophils (Spiegelberg, H L. J Clin Invest 56, 588 (1975)). It was concluded from these studies that the IgG1 half-molecule lacks non-covalent interactions characteristic for the Fc portion of the IgG heavy chain which destabilizes the molecule, and that the $C_H3$ domain may be particularly important in maintaining the interactions between IgG heavy chains.

Murine IgA half-molecules which were generated by somatic mutation have also been described (Mushinski, J F, J Immunol 106, 41 (1971); Mushinski, J F et al., J Immunol 117, 1668 (1976); Potter, M et al., J Mol Biol 93, 537 (1964); Robinson, E A et al., J Biol Chem 249, 6605 (1974); Zack, D J et al., J Exp Med 154, 1554 (1981)). These molecules were shown to all contain deletions of the $C_H3$ domain or mutations at the $C_H2$-$C_H3$ boundary. Human IgA half-molecules have also been detected in patients with multiple myeloma. These molecules were found to have deletions located to the $C_H3$ regions as well (Spiegelberg, H L et al., J Clin Invest 58, 1259 (1976); Kawai et al., Ann Acad Med Singapore 9, 50 (1980); Sakurabayashi, I. et al., Blood 53, 269 (1979); Biewenga, J. et al., Clin Exp Immunol 51, 395 (1983)).

Human IgG1 mutants having hinge deletions have been described and crystallized (Saphire, E O. et al., J Mol Biol 319, 95 (2002)). Dob and Mcg are human myeloma proteins of the human IgG1 subclass which contain a deletion of the hinge region. These hinge deleted IgG1 molecules form stable Igs with a structure consisting of two heavy and two light chains, which is the typical heterotetrameric structure of antibodies, that however form inter-chain disulphide bonds between the light chains resulting in molecules that are strongly conformationally restricted and which display little to no effector function (Burton D R et al., J Mol Biol 319, 9 (2002); Steiner, A et al., Biochemistry 18, 4068 (1979); Silverton, E W et al., Proc Natl Acad Sci USA 74, 5140 (1977); Rajan, S S et al., Mol Immunol 20 787 (1983); Guddat, W et al. Proc Natl Acad Sci USA 90, 4271 (1993); Sarma et al., J. Applied Cryst. 15, 476 (1982); Klein, M., et al., Proc Natl Acad Sci USA 78, 524 (1981)).

An IgG3 molecule in which the upper and middle hinge regions or the full hinge region was deleted, has been designed (Brekke, O H et al., Nature 363, 628 (1993); Brekke, O H et al., Nature 383, 103 (1996)). The molecule with the complete hinge deleted showed the presence of half-molecules upon analysis on non-reducing SDS-PAGE. A second hinge deleted molecule in which the complete upper and lower IgG3 hinge were replaced by a single cysteine and the lower IgG3 hinge contained a single Ala deletion, also contained half-molecules when analyzed on SDS-PAGE. However, the results show that under physiological conditions, the two heavy-light chain half-molecules are held together by non-covalent interactions between the IgG3 $C_H3$ domains; and intact IgG molecules were therefore formed.

A matched set of chimeric IgG1 and IgG4 antibodies has also been prepared (Horgan, C. et al. J Immunol 150, 5400 (1993)). To investigate the role of the IgG hinge region in antibody binding to antigen, mutants were prepared of both IgG1 and IgG4 which lacked the hinge region. The mutants were generated at the DNA level by deleting the hinge region exon from the IgG1 and IgG4 heavy chain genes. It was reported that both the IgG1 and IgG4 hinge-deleted molecules were bivalent, therefore having the typical heterotetrameric structure. In support of this, the functional affinity of the hinge-deleted IgG4 showed better binding to antigen than the wild-type IgG4, indicating that the avidity of the hinge-deleted molecule is not affected by the hinge deletion thus generated.

Human IgG4 molecules exist in various molecular forms which differ by the absence or presence of inter-heavy chain disulphide bonds located in the hinge region. Thus IgG4 molecules exist in which two, one or no inter-heavy chain disulphide bonds have been formed (Schuurman, J. et al., Mol Immunol 38, 1 (2001)). Under physiological conditions, these molecular forms of IgG4 may be in equilibrium with each other. Human IgG4s exist as tetramers in solution consisting of two Ig heavy and two light chains, as common for immunoglobulin G molecules, irrespective of the absence or presence of these interchain disulphide bonds (Schuurman 2001 supra; Gregory, L. et al. Mol Immunol 24, 821 (1987)). Only upon denaturation under non-reducing conditions, the two non-covalently associated half-molecules dissociate as demonstrated by size-determination analysis such as SDS-PAGE (Schuurman, J. et al. Mol Immunol 38, 1 (2001); Deng, L. et al. Biotechnol Appl Biochem 40, 261 (2004)). It has been shown that mutation of the residues of the hinge region which are involved in inter-chain disulphide bond formation or deletion of the hinge region lead to creation of a homogeneous pool of IgG4 molecules in solution, which pool consists of tetrameric molecules consisting of two light chains and two heavy chains (Schuurman, J. et al. Mol Immunol 38, 1 (2001); Horgan, C. et al. J Immunol 150, 5400 (1993)). The IgG4 hinge-deleted and mutated antibodies also demonstrated an improved capability of antigen crosslinking when compared to native $IgG_4$ molecules (Horgan, C. (1993) supra).

A number of studies have now shown that mutation or deletion of the IgG constant region domains $C_H1$ and $C_H2$ do not affect the assembly of IgG molecules into their natural two heavy and two light chain heterotetrameric configuration. Recombinant antibody molecules containing different deletions in their constant regions of the heavy chain have been shown to be affected in their effector function, e.g. they are not capable of complement activating, however, they remain their ability of antigen crosslinking. Further, it has been demonstrated that antibody half-molecules containing one heavy chain and one light chain are not stable in vivo and/or have a decreased half-life in vivo. Deletions in/of the $C_H3$ region provide half-molecules having a rapid metabolization making them unfit for most therapeutic purposes.

There is thus a need for a simple and improved procedure for the production of a stable monovalent antibody, which would be suitable for therapeutic applications, wherein blocking of an antigen-mediated activity requires monovalent antibody binding (absence of cross-linking).

SUMMARY OF THE INVENTION

In a first main aspect, the invention relates to a non-human transgenic animal, which upon antigenic stimulation is capable of producing a monovalent antibody binding to a selected antigen, which monovalent antibody comprises a heavy chain, which heavy chain comprises
  (i) a human $V_H$ region, and
  (ii) a human $C_H$ region, wherein the $C_H$ region has been modified such that the region corresponding to the hinge region and, optionally other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

The transgenic animals of the invention provide an efficient way of generating monovalent human antibodies having a long half-life. The transgenic animals of the invention are highly suitable for obtaining and selecting high-affinity monovalent antibodies. During immunization the monovalent human antibodies undergo affinity maturation in the non-human transgenic animal, resulting in antibodies with high affinity.

The transgenic animals of the invention may be generated using well-known methods or techniques used for generating transgenic animals. For example, the transgenic animals may be generated using a method analogous to any of the methods referred to above for generating the HuMab™, KM-Mouse™, TC-Mouse™ or Xenomouse™.

In a further main aspect, the invention relates to a non-human transgenic animal, which upon antigenic stimulation is capable of producing a monovalent IgG4 antibody binding to a selected antigen, which monovalent antibody comprises
    a heavy chain, which heavy chain comprises
        (i) a human $V_H$ region, and
        (ii) a human $C_H$ region, wherein the $C_H$ region has been modified such that the region corresponding to the hinge region does not comprise any amino acid residues, which are capable of forming disulfide bonds with an identical $C_H$ region, and
    a light chain, which light chain comprises
        (i) a human $V_L$ region, and
        (ii) a human $C_L$ region.

In a further main aspect, the invention relates to a non-human transgenic animal, which upon antigenic stimulation is capable of producing a monovalent IgG4 antibody binding to a selected antigen, which monovalent antibody comprises
    a heavy chain, which heavy chain comprises
        (i) a human $V_H$ region, and
        (ii) a human $C_H$ region, wherein the $C_H$ region has been modified such that the region corresponding to the hinge region does not comprise any amino acid residues which are capable of forming disulfide bonds with an identical $C_H$ region, and wherein the $C_H3$ region has the sequence as set forth in SEQ ID NO: 16, but wherein the $C_H3$ region has been modified so that one or more of the following amino acid substitutions have been made: Thr (T) in position 234 has been replaced by Ala (A); Leu (L) in position 236 has been replaced by Val (V); Phe (F) in position 273 has been replaced by Ala (A); Phe (F) in position 273 has been replaced by Leu (L); Tyr (Y) in position 275 has been replaced by Ala (A); Arg (R) in position 277 has been replaced by Ala (A),
and
    a light chain, which light chain comprises
        (i) a human $V_L$ region, and
        (ii) a human $C_L$ region.

In a further main aspect, the invention relates to a non-human transgenic animal, which upon antigenic stimulation is capable of producing a monovalent IgG1 antibody binding to a selected antigen, which monovalent antibody comprises a heavy chain, which heavy chain comprises
    (i) a human $V_H$ region, and
    (ii) a human $C_H$ region, wherein the $C_H$ region has been modified such that the region corresponding to the hinge region and the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG,
and a light chain, which light chain comprises
    (i) a human $V_L$ region, and
    (ii) a human $C_L$ region, which has been modified such that the $C_L$ region does not contain any amino acids, which are capable of forming disulfide bonds with an identical $C_L$ region or other covalent bonds with an identical $C_L$ region in the presence of polyclonal human IgG.

In a further main aspect, the invention relates to a heavy chain transgene comprising (i) a plurality of human V genes, a plurality of human D genes, a plurality of human J genes,
(ii) a plurality of human $C_H$ genes and associated isotype switch sequences, comprising a human $\mu$ $C_H$ gene and at least one modified $\gamma$ $C_H$ gene, wherein the human $\gamma$ $C_H$ gene is in closer proximity to the human $\mu$ $C_H$ gene than in a naturally occurring human immunoglobulin heavy chain gene locus.

In a further main aspect, the invention relates to a method of producing a monovalent antibody binding to a selected antigen comprising
(i) immunizing the animal according to the invention with a selected antigen, a cell expressing a selected antigen, or a nucleic acid construct encoding a selected antigen or a combination thereof
(ii) obtaining B cells from the transgenic animal expressing monovalent antibodies binding to the selected antigen,
(iii) optionally generating hybridomas from said B cells,
(iv) testing the monovalent antibodies produced by the B cells or hybridomas for binding to the selected antigen, and
(v) identifying one or more monovalent antibodies capable of binding to the selected antigen.

In a further main aspect, the invention relates to a monovalent antibody obtainable by the method according to the invention as defined herein.

In a further main aspect, the invention relates to a monovalent antibody obtained by the method according to the invention as defined herein.

In a further main aspect, the invention relates to the use of a non-human transgenic animal according to the invention as defined herein for generating a monovalent antibody.

In a further main aspect, the invention relates to a method for producing a non-human transgenic animal according to the invention as defined herein, comprising
(i) introducing into the embryonic stem cells of a non-human animal, a heavy chain transgene construct according to the invention, and optionally a light chain transgene capable of producing the light chain as defined herein,
(ii) selecting embryonic stem cells expressing the transgene(s),
(iii) injecting the transformed embryonic stem cells into the inner mass of a blastocyst,
(iv) implanting the blastocysts into the uterus or oviduct of a non-human pseudopregnant female animal,
(v) testing the offspring for the presence of the transgene(s), and
(vi) mating two heterozygous offspring to produce homozygous transgenic strain of the non-human animal.

In a further main aspect, the invention relates to a method for producing a non-human transgenic animal according to the invention, comprising
(i) injecting into the pronucleus of a fertilized ovum of a non-human animal of a vector construct comprising the transgene according to the invention, and optionally a light chain transgene capable of producing the light chain defined herein,
(ii) implanting the fertilized ovum into the uterus or oviduct of a non-human pseudopregnant female animal,
(iii) testing the offspring for the presence of the transgene(s), and
(iv) mating two heterozygous offspring to produce homozygous transgenic strain of the non-human animal.

In a further main aspect, the invention relates to a method for producing a non-human transgenic animal according to the invention, comprising
(i) introducing into the embryonic stem cells of a non-human transgenic animal, which transgenic animal comprises pre-existing transgenic sequences allowing the animal to producing human antibodies, a transgene comprising a sequence which encodes a $C_H$ region or fragment thereof comprising the modifications as defined herein, and, optionally, a transgene comprising a sequence which encodes a $C_L$ region or fragment thereof comprising the modification herein, said transgene(s) being designed to, upon genomic integration and replacement of the corresponding human $C_H$ region or fragment thereof, and, optionally, corresponding human $C_L$ region or fragment thereof, of the transgenic animal genome become(s) operably linked to the remaining pre-existing transgenic sequences thus allowing the animal to produce monovalent antibodies as defined herein, (ii) selecting embryonic stem cells expressing the transgene(s) introduced in step (i), (iii) injecting the transformed embryonic stem cells into the inner mass of a blastocyst, (iv) implanting the blastocysts into the uterus or oviduct of a non-human pseudopregnant female animal, (v) testing the offspring for the presence of the transgene(s), and (vi) mating two heterozygous offspring to produce homozygous transgenic strain of the non-human animal.

In a further main aspect, the invention relates to a method for producing a non-human transgenic animal according to the invention, comprising (i) injecting into the pronucleus of a fertilized ovum of a non-human transgenic animal, which transgenic animal comprises pre-existing transgenic sequences allowing the animal to producing human antibodies, a transgene comprising a sequence which encodes a $C_H$ region or fragment thereof comprising the modifications as defined herein, and, optionally, a transgene comprising a sequence which encodes a $C_L$ region or fragment thereof comprising the modification as defined herein, said transgene(s) being designed to, upon genomic integration and replacement of the corresponding human $C_H$ region or fragment thereof, and, optionally, corresponding human $C_L$ region or fragment thereof, of the transgenic animal genome become(s) operably linked to the remaining pre-existing transgenic sequences thus allowing the animal to produce monovalent antibodies as defined herein, (ii) implanting the fertilized ovum into the uterus or oviduct of a non-human pseudopregnant female animal, (iii) testing the offspring for the presence of the transgene(s) introduced in step (i), and (iv) mating two heterozygous offspring to produce homozygous transgenic strain of the non-human animal.

In a further aspect, the invention relates to a non-human transgenic animal obtainable or obtained by the above methods.

Lane 1: Marker SeuBlue plus2 prestained (Invitrogen BV, The Netherlands), Lane 2: internal control, Lane 3: 7D8-IgG1, Lane 4: 7D8-IgG4, and Lane 5: 7D8-HG.

Figure 2:
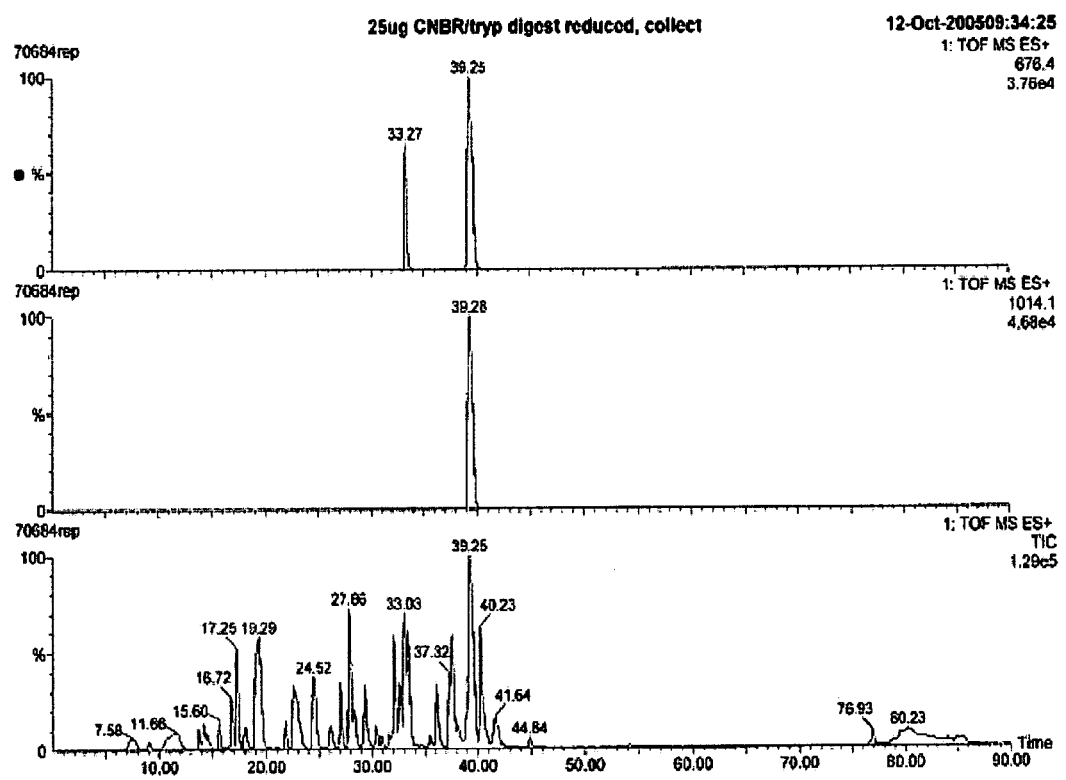

FIG. 2: Extracted ion chromatogram for [M+3H]3+ and [M+2H]2+ ions (m/z 676.4 and 1014.1 respectively) eluting at 39.3 mins TIC time in the reduced CNBr/tryptic digest of 7D8-HG.

Figure 3:
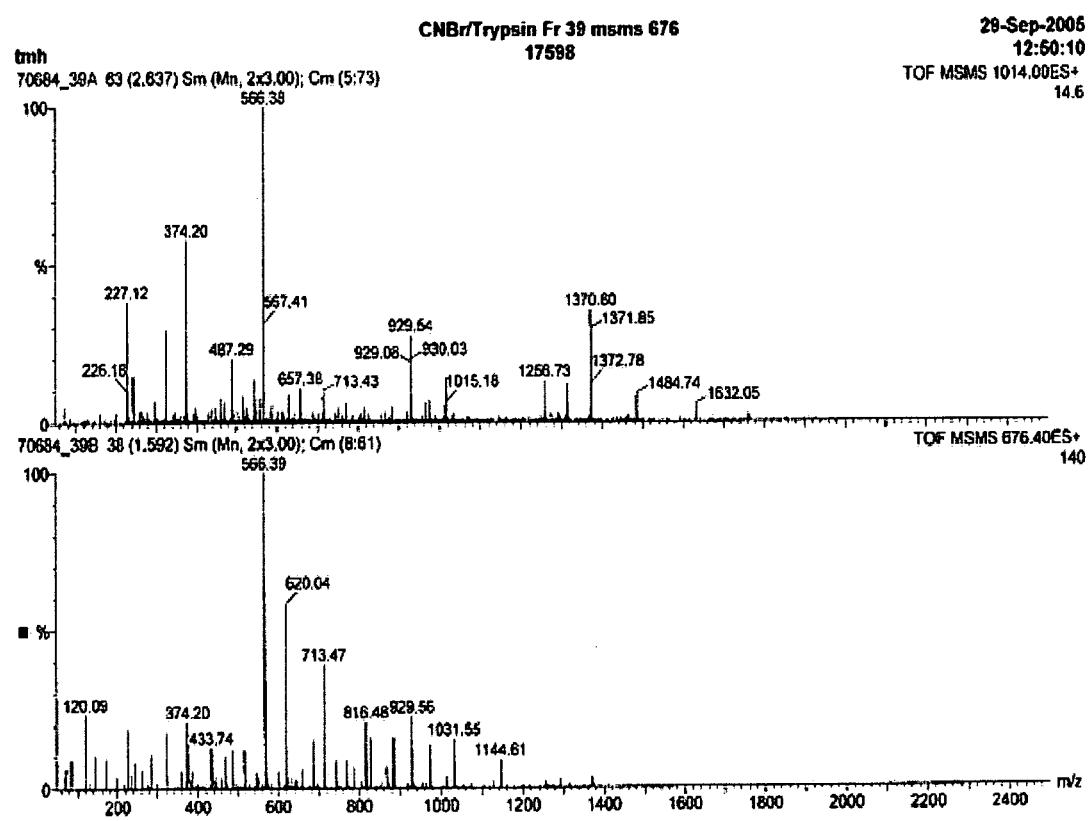

FIG. 3: The raw data obtained from nanospray-MS/MS analysis of the m/z signals consistent with a peptide covering amino acid residues 220 to 238 (220VAPEFLGGPSVFLFP-PKPK238) (SEQ ID NO: 54) from a reduced CNBr/tryptic digest of 7D8-HG.

Figures 4A, 4B:
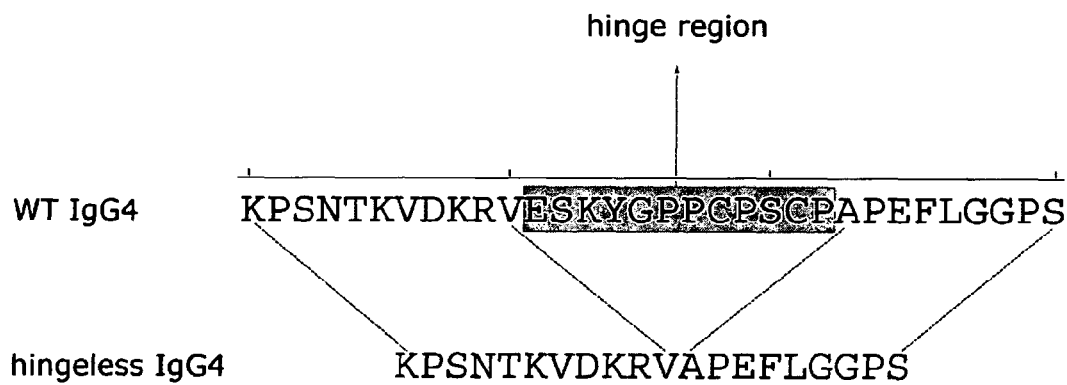

FIGS. 4A and B: Interpretation of the raw data obtained from nanospray-MS/MS analysis of the m/z signals consistent with a peptide covering amino acid residues 220 to 238 (220VAPEFLGGPSVFLFPPKPK238) (SEQ ID NO: 54) from a reduced CNBr/tryptic digest of 7D8-HG. The sequences shown in FIG. 4B are given in SEQ ID NO: 55 and SEQ ID NO: 56. The highlighted sequence corresponds to amino acids 99-110 of SEQ ID NO: 14 which are deleted in SEQ ID NO: 16.

Figure 5:
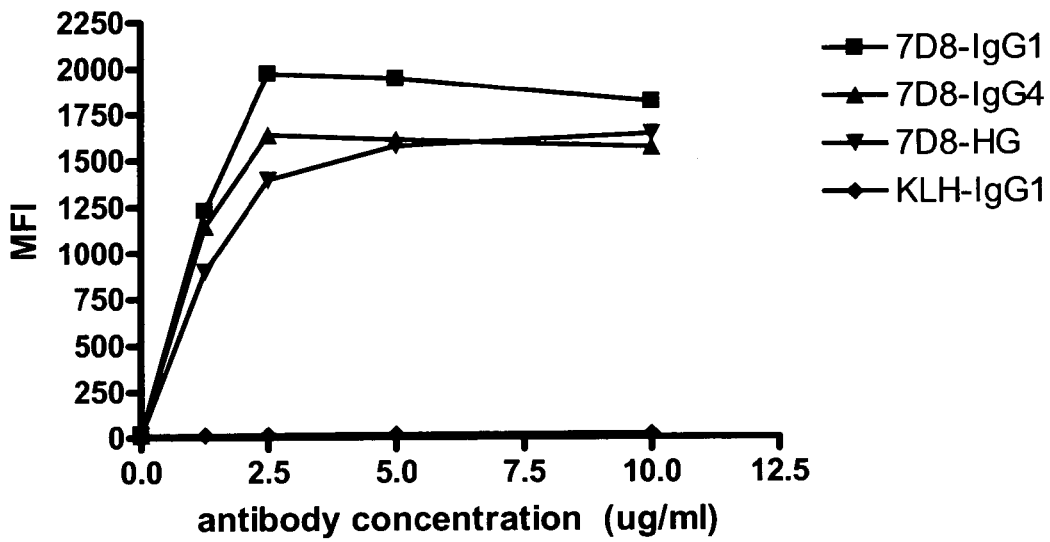

FIG. 5: The CD20-specific antibodies 7D8-IgG1, 7D8-IgG4 and 7D8-HG were evaluated on their binding to CD20 transfected cells.

Figure 6:
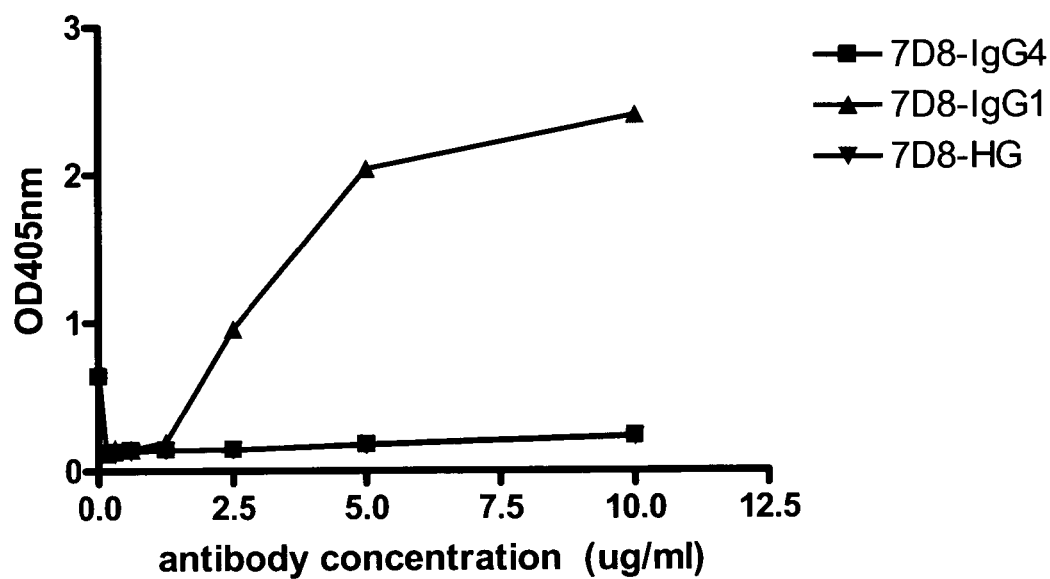

FIG. 6: The CD20-specific antibodies 7D8-IgG1, 7D8-IgG4 and 7D8-HG were coated on an ELISA plate (concentration range as indicated on x-axis). C1q binding (2 µg/ml) was evaluated.

FIG. 7: A) Daudi cells were pre-incubated with a concentration range of the CD20-specific antibodies for 10 minutes, before NHS was added. Forty-five minutes after induction of CDC, cells were resuspended in PI solution. Cell lysis (number of PI-positive cells) was measured by flow cytometry. Data show the Mean Fluorecence intensity of the PI-positive (dead) cells.

B) To evaluate the role of complement in the lysis measured, heat-inactivated serum (serum ΔT) was added to cells incubated with 10 µg antibody. Data show the mean fluorescence intensity of the PI-positive (dead) cells.

Figure 8:
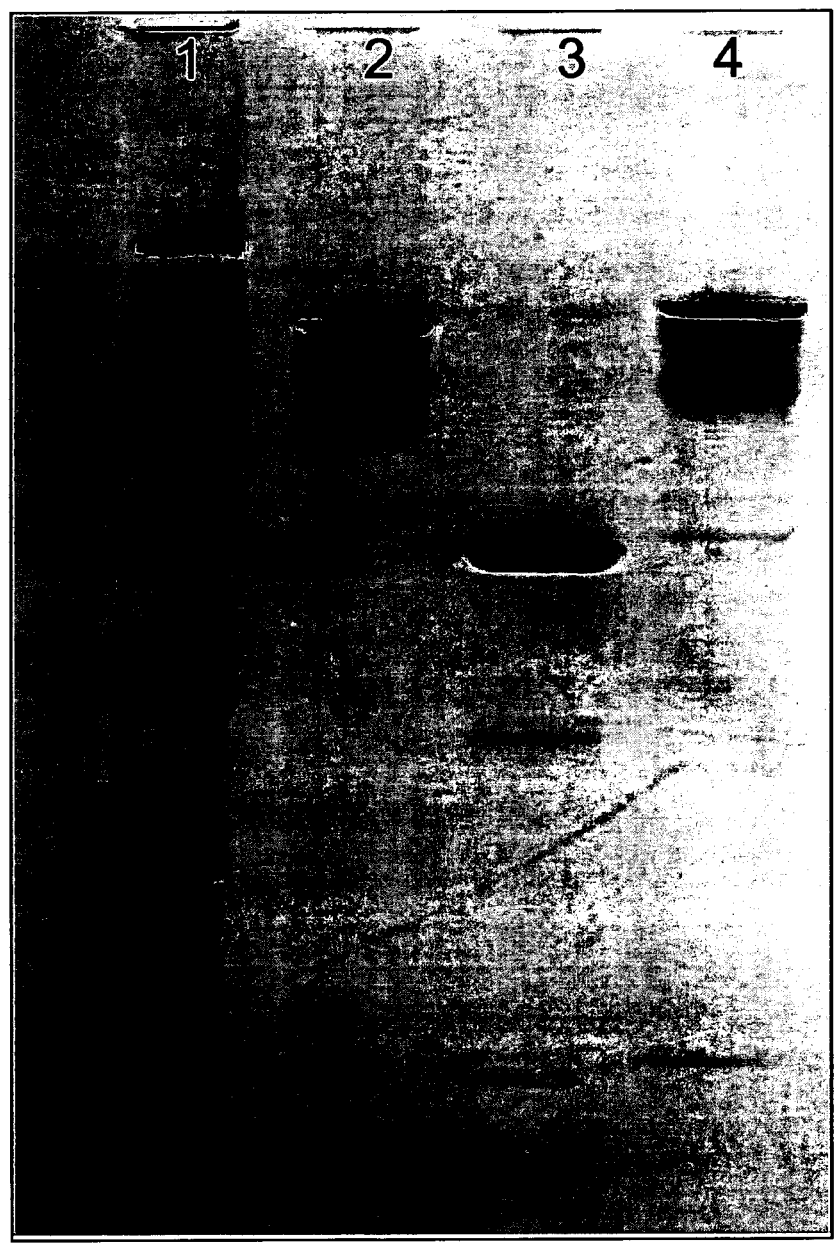

FIG. 8: The hingeless IgG4 antibody directed against Bet v 1 (Betv1-HG) was tested on non-reducing SDS-PAGE.

Lane 1: Marker SeaBlue plus2 prestained (Invitrogen BV, The Netherlands), lane 2: internal control, lane 3: BetV1-HG, lane 4: IgG1 control.

Figure 9:
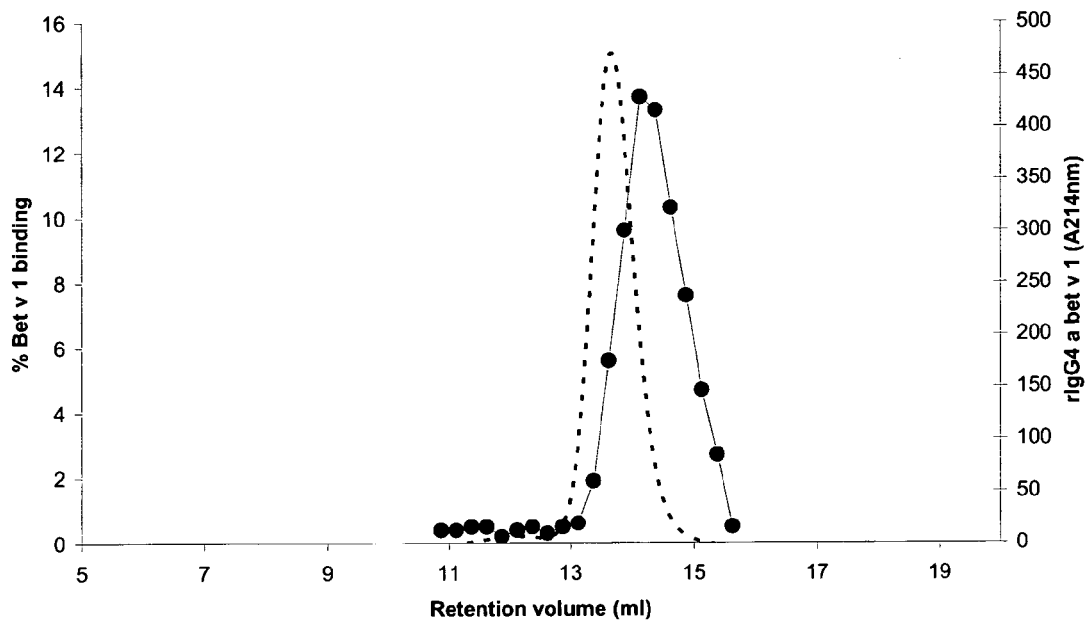

FIG. 9: Gelfiltration of Betv1-HG (hingeless IgG4 anti-Bet v 1). Conditioned medium from HEK cells containing hingeless rIgG4 Betv1-HG was fractionated on a Superdex200 column. A total 1 µg of Betv1-HG was applied to the column. In the fractions, Bet v 1 specific IgG (•) was measured by incubating 10 µl of each fraction in the Bet v 1 binding test. The results are expressed as percentage of radiolabeled Bet v 1 binding relative to the amount added. The dashed curve represents the elution of purified Betv1-IgG4 (10 µg), which was followed on the HPLC by measuring the absorption at 214 nm (A214 nm).

Figure 10:
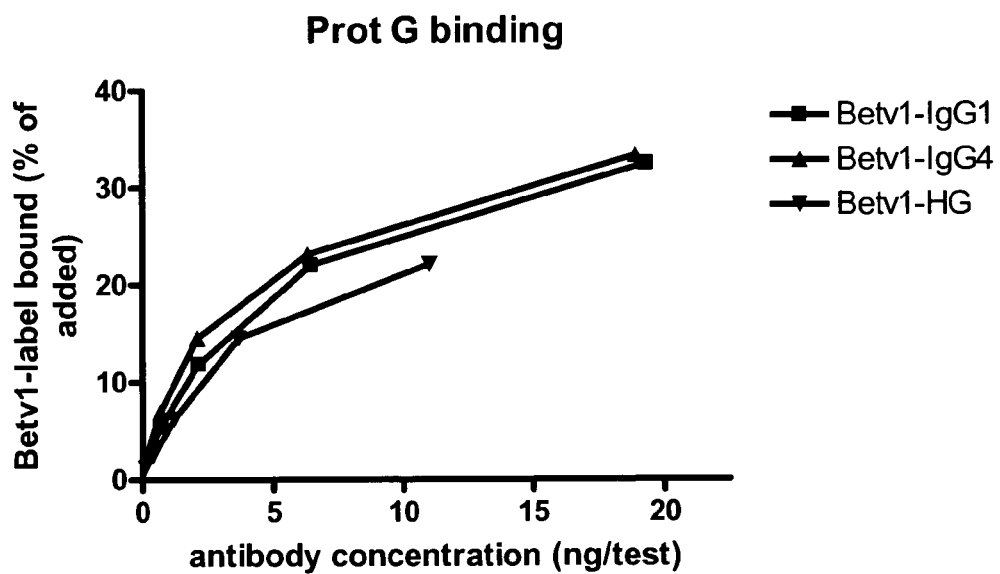

FIG. 10: The binding of Betv1-IgG1, Betv1-IgG4 and Betv1-HG was examined in a radio immuno assay. The binding of $^{125}$I-labelled Bet v1 to serial dilutions of the antibodies bound to Protein G Sepharose was examined.

Figure 11:
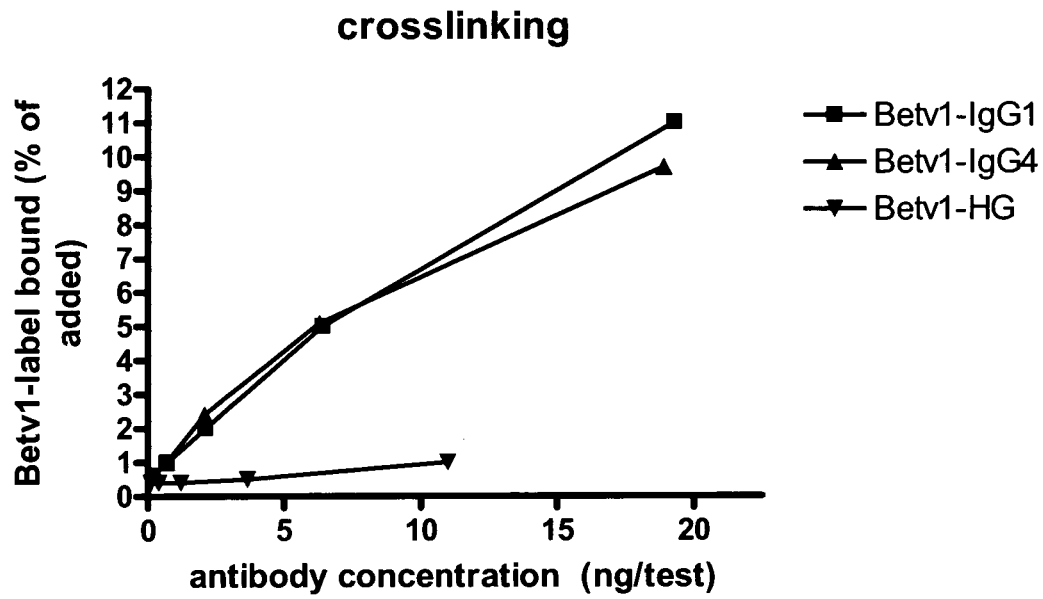

FIG. 11: The ability of Betv1-IgG1, Betv1-IgG4 and Betv1-HG to crosslink Sepharose bound Bet v 1 to radiolabelled Bet v 1 was examined in an radio immuno assay. The binding of $^{125}$I-labelled Bet v1 to serial dilutions of the antibodies bound to Bet v 1 Sepharose was examined.

Figure 12:
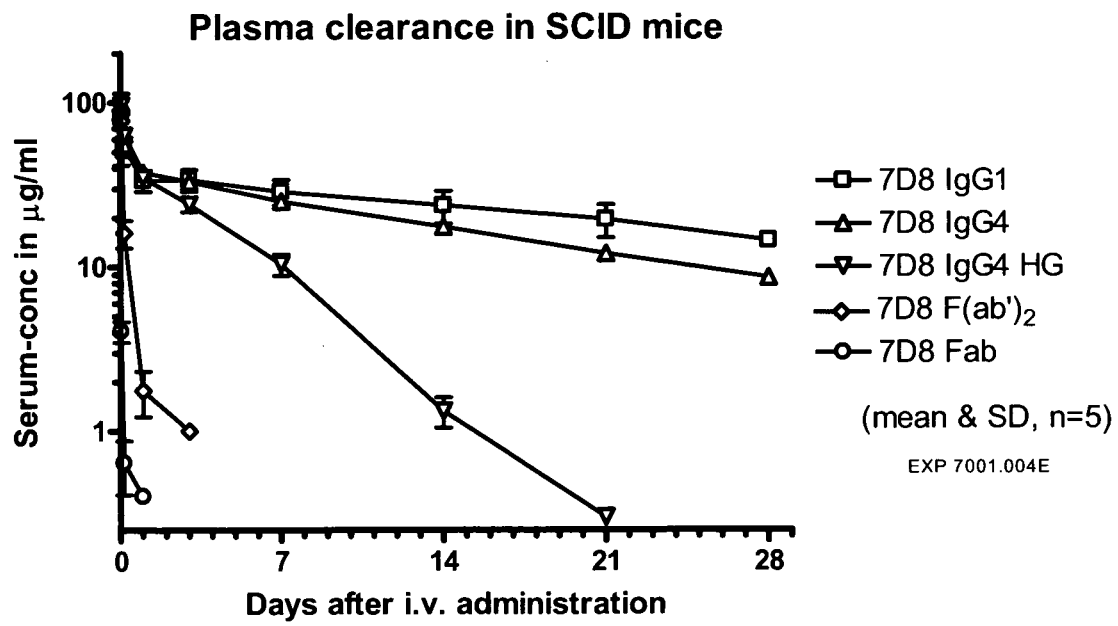

FIG. 12: Semilogarithmic plot of the mouse plasma concentrations of 7D8-HG in comparison with normal 7D8-IgG4, intact 7D8-IgG1, 7D8-IgG1, F(ab')2 and 7D8-IgG1 Fab fragments after intravenous administration of 100 ug per mouse.

Figure 13:
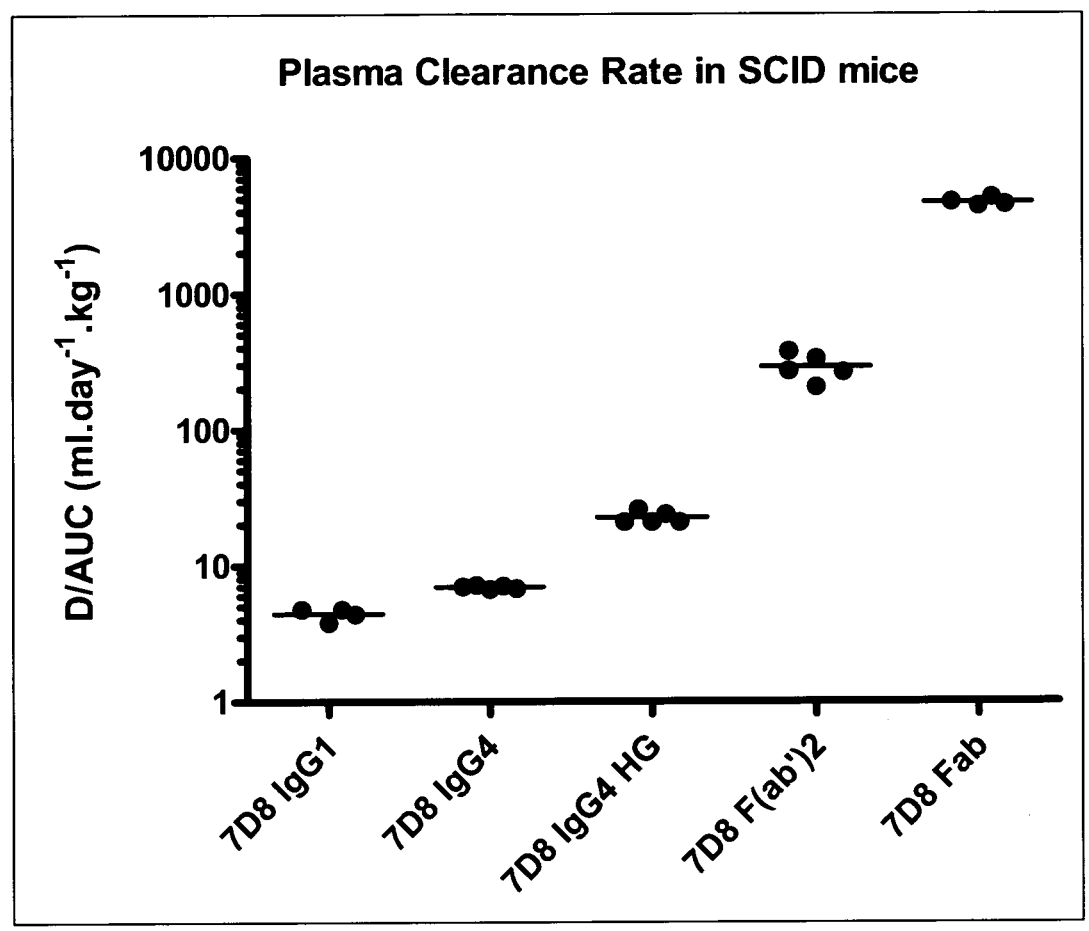

FIG. 13: Logarithmic plot of the plasma clearance rates as dose/area under the curve calculated from the concentration-time curves (D/AUC). The data represent individual mice and are expressed in ml·day$^{-1}$·kg$^{-1}$.

Figure 14:
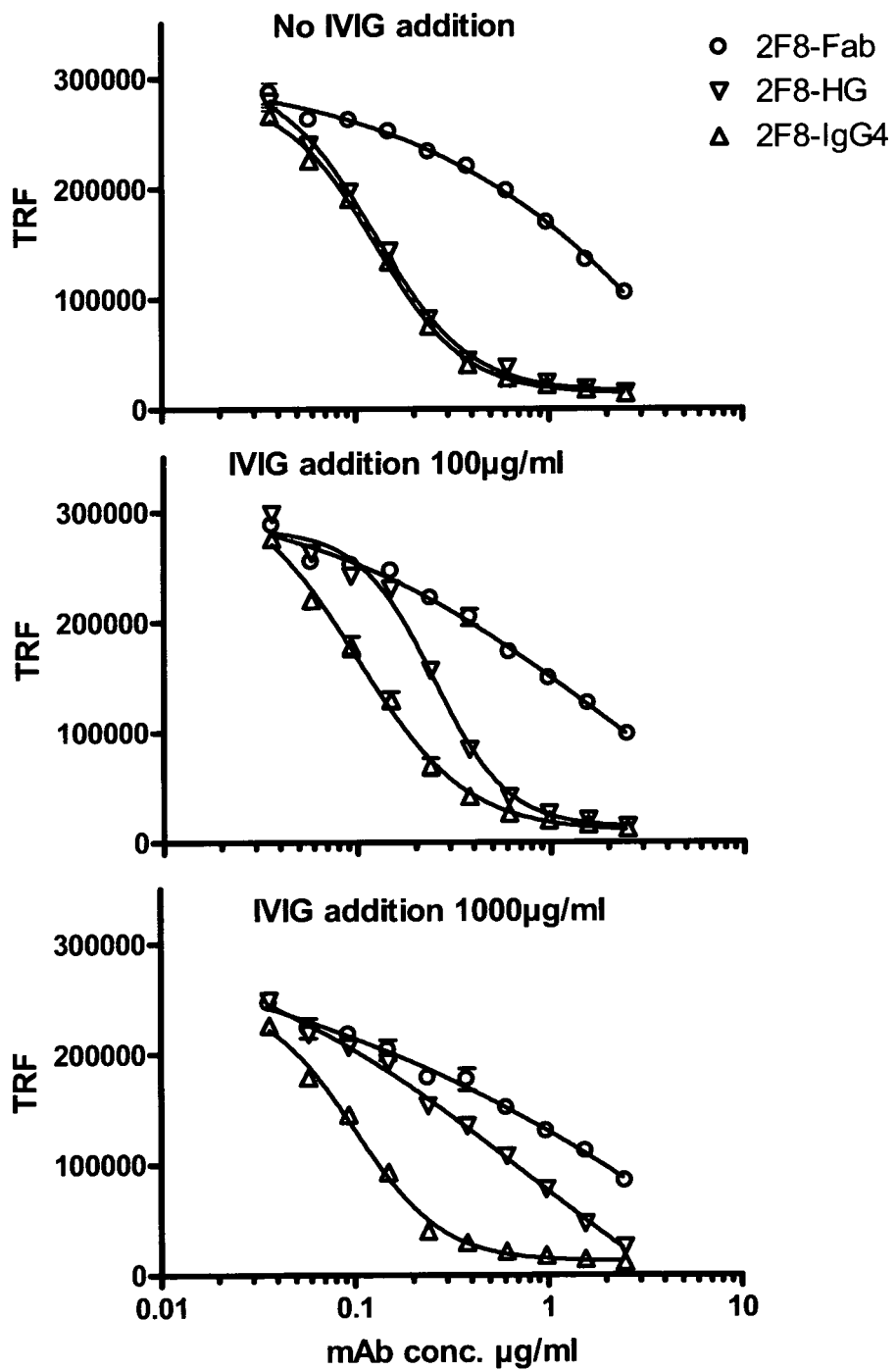

FIG. 14: Dose-response curves showing the inhibition of EGF-induced EGFr phosphorylation in A431 cells by anti-EGFr mAb 2F8-HG, compared with 2F8-IgG4 and 2F8-Fab fragments. The upper panel shows the inhibition curves in serum-deprived medium, the middle and lower panels the inhibition when IVIG was added to the medium at a concentration of 100 µg/ml and 1000 µg/ml, respectively. The y-axis represents phosphorylated EGFr as detected with an anti-phospho-tyrosine mAb and is expressed in time-resolved fluorescence units (TRF units). On the x-axis, the mAb concentration in µg/ml. Data points are mean and SEM of 4 replicates.

Figure 15:
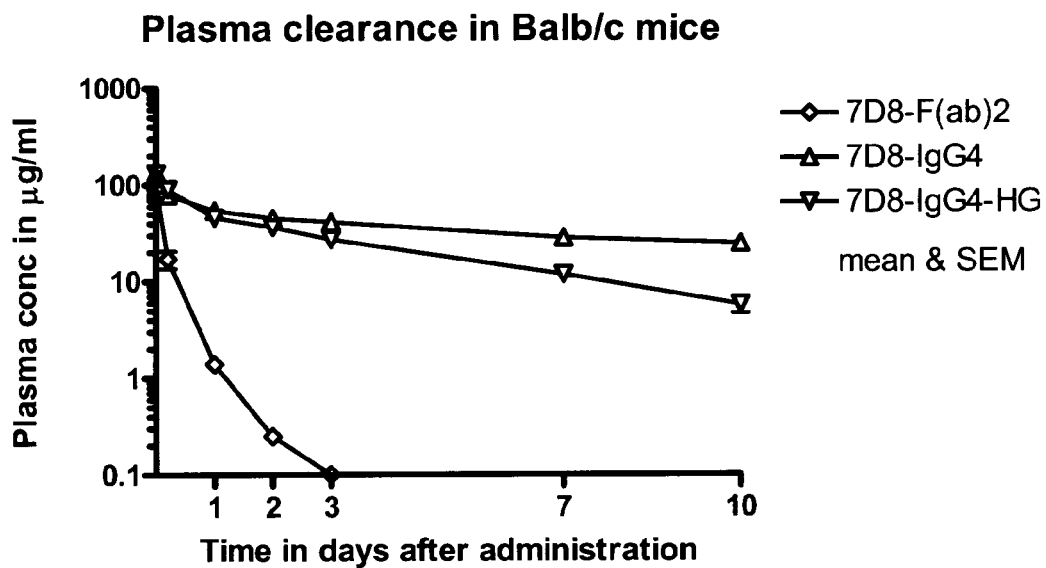

FIG. 15: A semilogarithmic plot of the concentrations in time. The initial plasma concentrations were all in the order of 100 µg/ml, which is consistent with an initial distribution into the plasma compartment of the mice. The clearance of the hingeless IgG4 variant was only slightly faster than that of normal IgG4. Importantly, the clearance of the hingeless variant was much slower than that of F(ab')₂ fragments, which have a comparable molecular size.

This experiment indicates that the Fc-part has a favorable effect on the plasma residence time in mice having a normal immune system and provides an indication of a functional interaction with the neonatal Fc receptor (FcRn) also in the presence of endogenous IgG.

Figure 16:
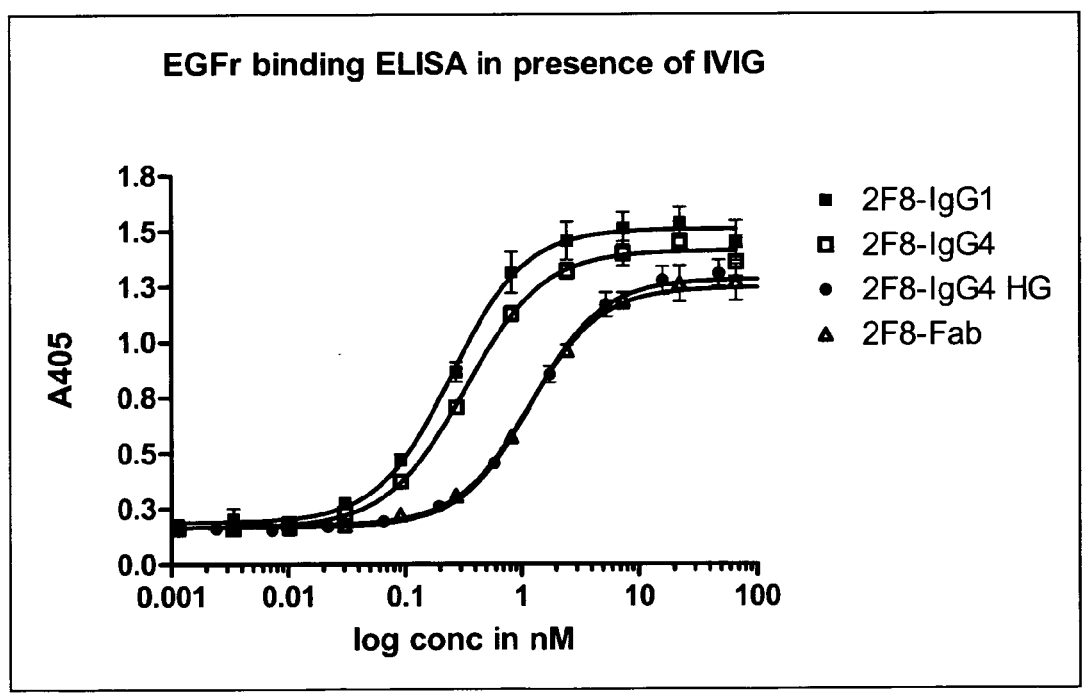

FIG. 16: The binding of 2F8-HG to a coat of EGFr protein was compared in an ELISA to that of 2F8-IgG4, 2F8-IgG1 and Fab fragments of 2F8-IgG1, in the presence of polyclonal human IgG (IVIG) at a concentration of 100 µg/ml.

Figure 17:
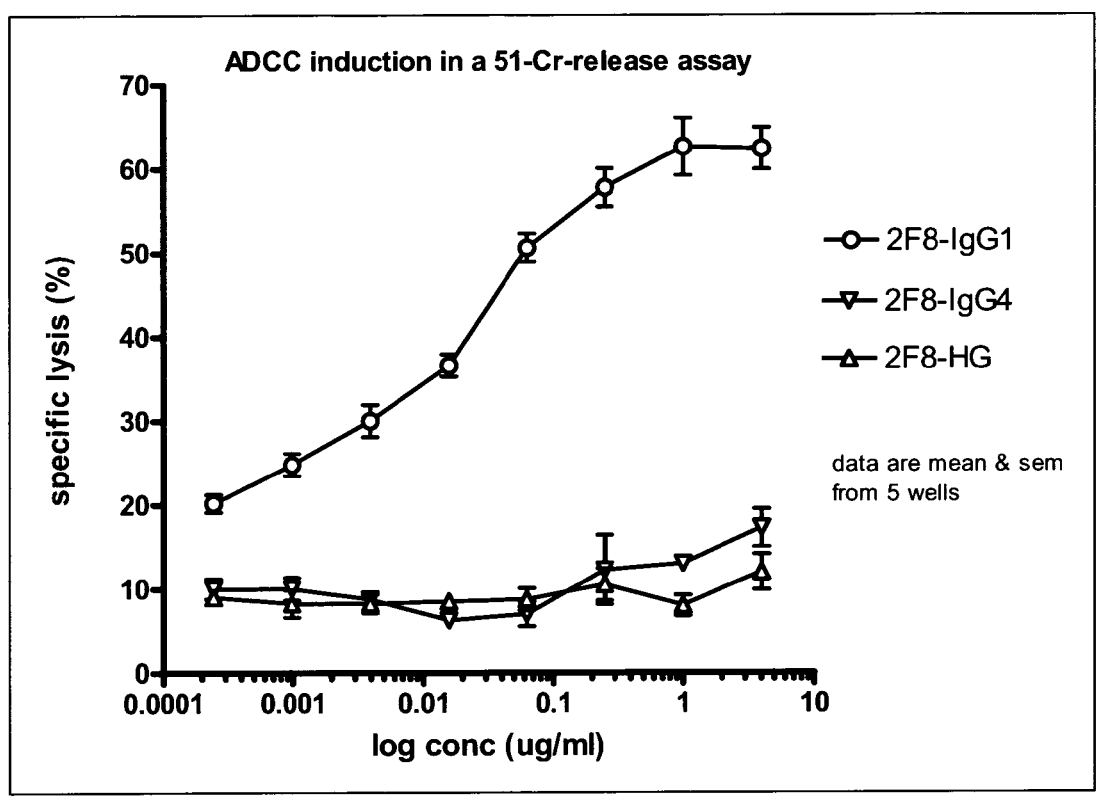

FIG. 17: The induction of ADCC by 2F8-HG was compared to that by 2F8-IgG1 and 2F8-IgG4. A431 cells were used as target cells and human peripheral blood mononuclear cells as effector cells FIG. 18: Sequence of primers used in the Examples.

FIG. 19: Sequences of primers used in the Examples.

Figure 20:
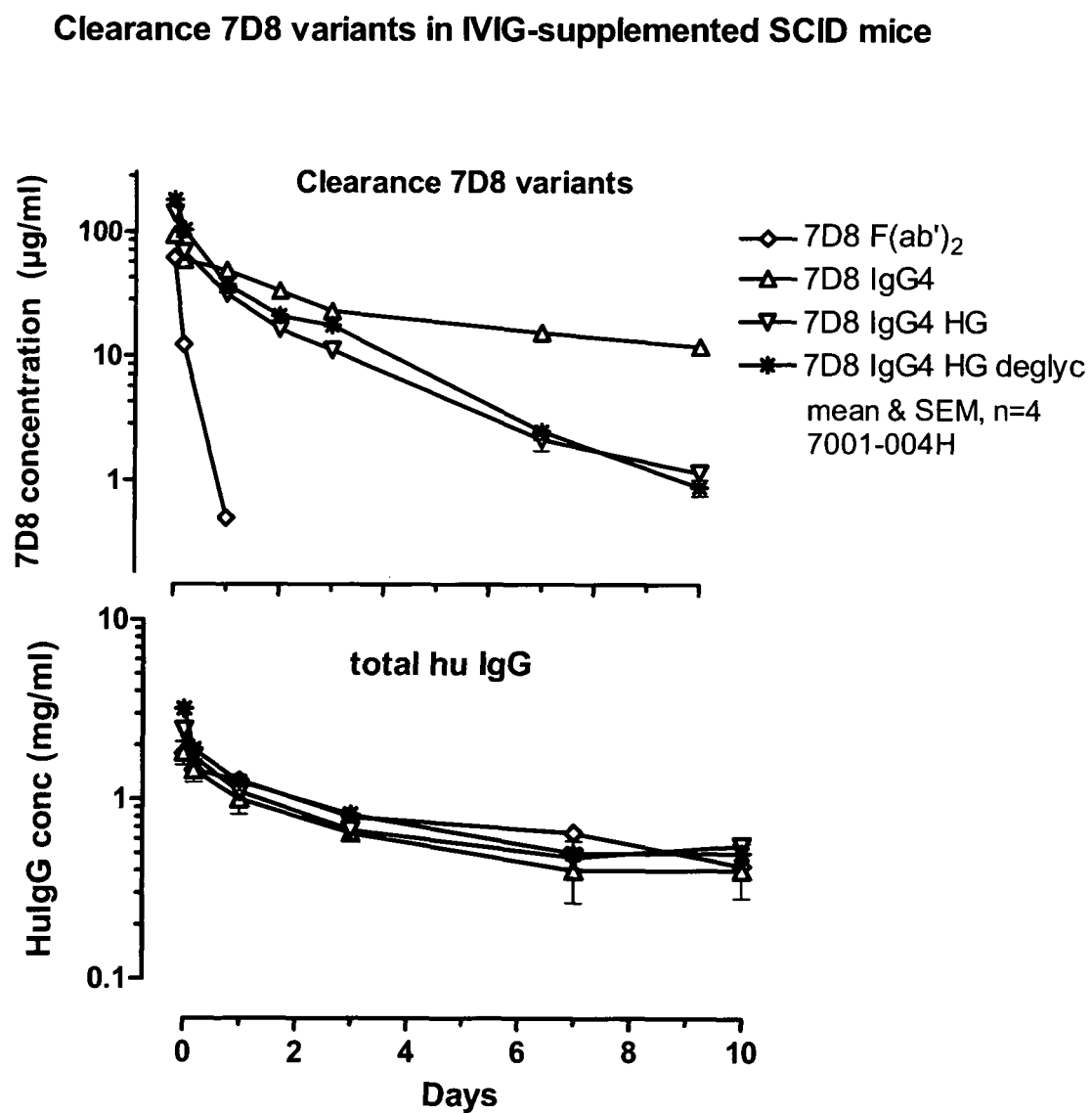

FIG. 20: Clearance of 7D8 variants in IVIG supplemented SCID mice. The figure shows in the upper panel semi-logarithmic plots of the concentrations of the mAb 7D8 variants in time and in the lower panel the total human IgG concentrations.

Figure 21:
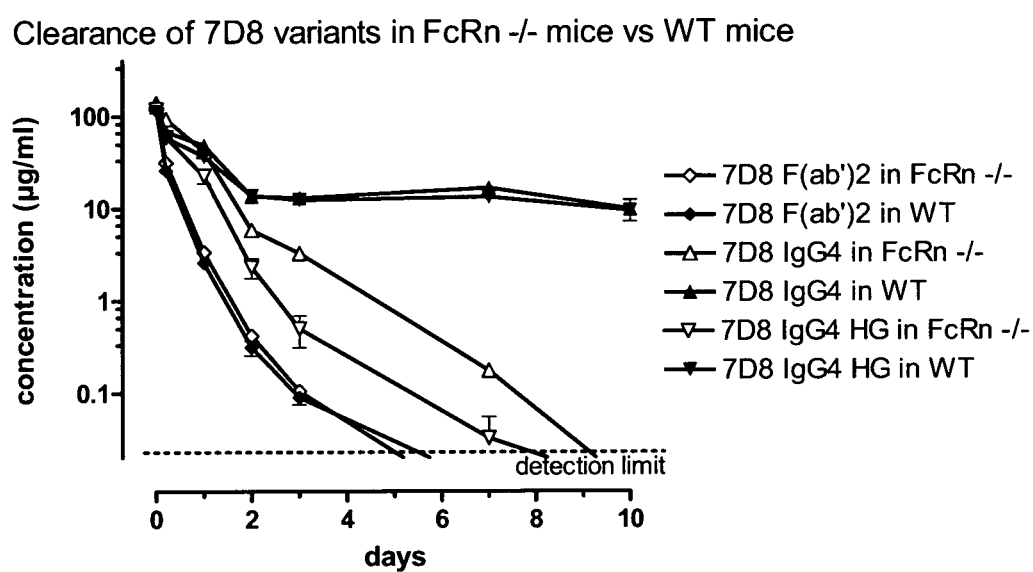

FIG. 21: Clearance with 7D8 variants in FcRn −/− mice vs wild type mice. The figure shows a semi-logarithmic plot of the concentrations in time. The initial plasma concentrations were all in the order of 100 µg/ml, which is consistent with an initial distribution in the plasma compartment of the mice. The hingeless IgG4 variant (7D8-HG), normal human IgG4 (7D8-IgG4) and F(ab')₂ fragments from 7D8 IgG1 (7D8-G1-F(ab')₂) were compared in the model.

Figure 22A:
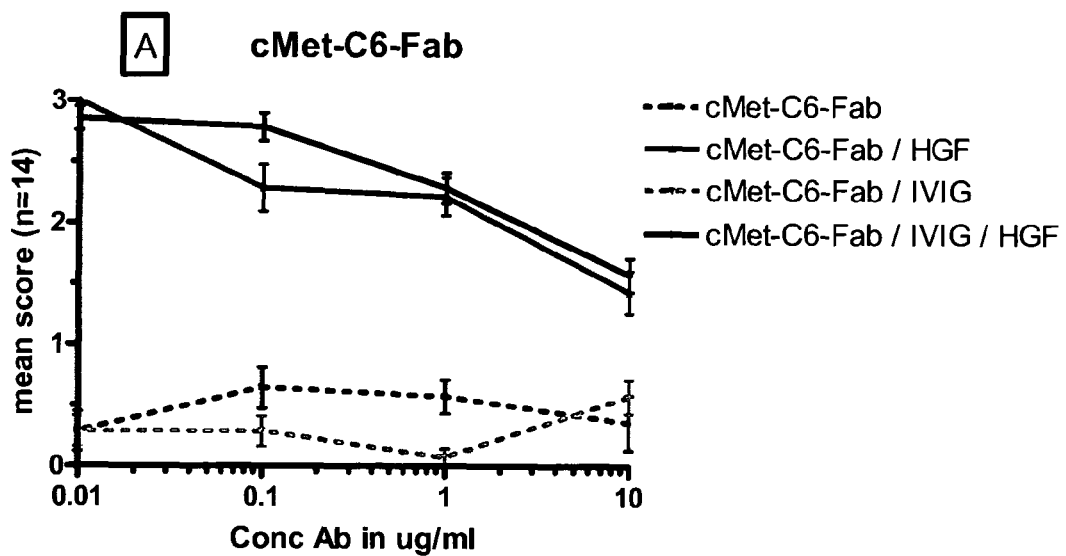
Figure 22B:
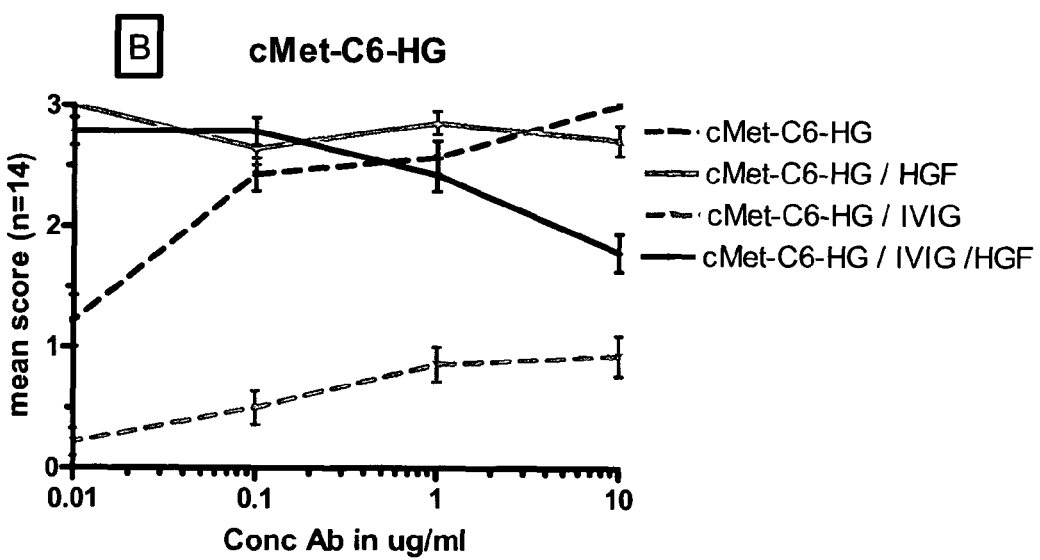

FIG. 22: DU-145 cells were cultured and incubated with a serial dilution of (A) cMet-Fab, cMet-Fab and IVIG, cMet-Fab and HGF, cMet-Fab and IVIG and HGF (B) cMet-HG, cMet-HG and IVIG, cMet-HG and HGF, cMet-HG and IVIG and HGF. Scattering was observed double-blinded (scored by 14 people) by microscope after 48 h and the averaged score±SEM is plotted.

Figure 23:
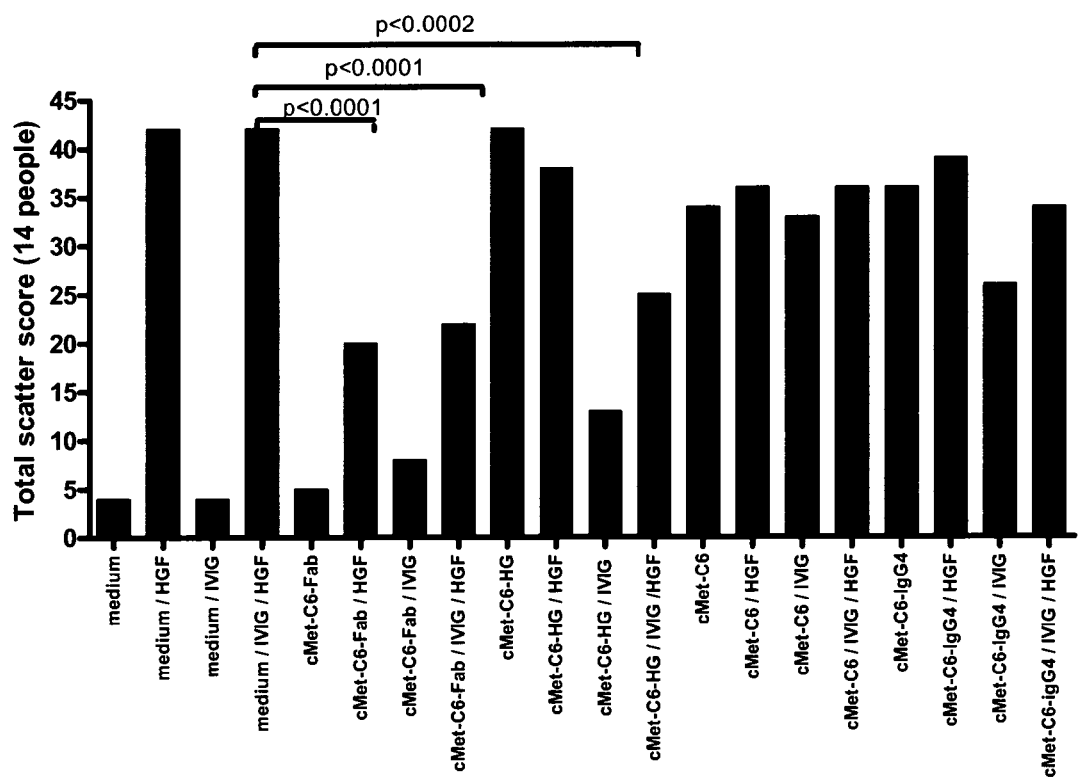

FIG. 23: DU-145 cells were cultured and incubated with 10 µg/ml of (A) cMet-Fab, cMet-Fab and IVIG, cMet-Fab and HGF, cMet-Fab and IVIG and HGF (B) cMet-HG, cMet-HG and IVIG, cMet-HG and HGF, cMet-HG and IVIG and HGF. Scattering was observed double-blinded (scored by 14 people) by microscope after 48 h. cMet-Fab with or without IVIG and cMet-HG pre-incubated with IVIG significantly inhibited the HGF induced scattering. For statistical analysis a two-tailed Wilcoxon signed ranked test was done with a hypothetical median value of 3 (maximal scattering).

Figure 24:
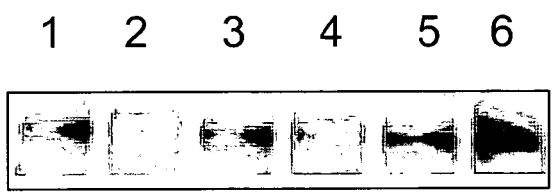

FIG. 24: Extracts prepared from A549 cells incubated with cMet-HG (lane 1), cMet-HG and IVIG (lane 2), cMet-HG and HGF (lane 3), cMet-HG, IVIG and HGF (lane 4), cMet-IgG1 (lane 5), cMet-IgG1 and IVIG (lane 6) were resolved by SDS-PAGE on a 4-20% Tris-HCl Criterion Precast gel and Western blotting on a nitrocellulose membrane. The membrane was incubated over night at 4° C. with anti-phospho-Met(pYpYpY 1230 1234 1235)-rabbit IgG, (Abcam, ab5662). After washing with TBST, the secondary antibodies, goat-anti-rabbit-HRP, Cell Signalling, 7074 in blocking reagent were incubated for 60 min. at room temperature on a roller bank. The membrane was washed 6 times with TBST. Finally the bands were developed with Luminol Enhancer stop solution and analyzed on a Lumiimager. The Western blot shows a 169 Kd band indicating phospho-Met(pYpYpY 1230 1234 1235).

FIG. 25: Starting concentration of addition of HuMax-CD4 or Fab fragments of HuMax-CD4 to the in vitro HIV-1 neutralization assay. The IC50 values of inhibition by HuMax-CD4 and Fab fragments of HuMax-CD4 are calculated by a 4 parameter logistic curve fit and indicated for each of the virus constructs.

FIG. 26: The % human T cells, % murine cells, and % CD4 and % CD8 cells, and the ratio CD4/CD8 of the individual PBMC reconstituted mice treated intraperitoneally with HuMax-CD4, IgG control or non treated, and infected with HIV-1.

Figure 27:
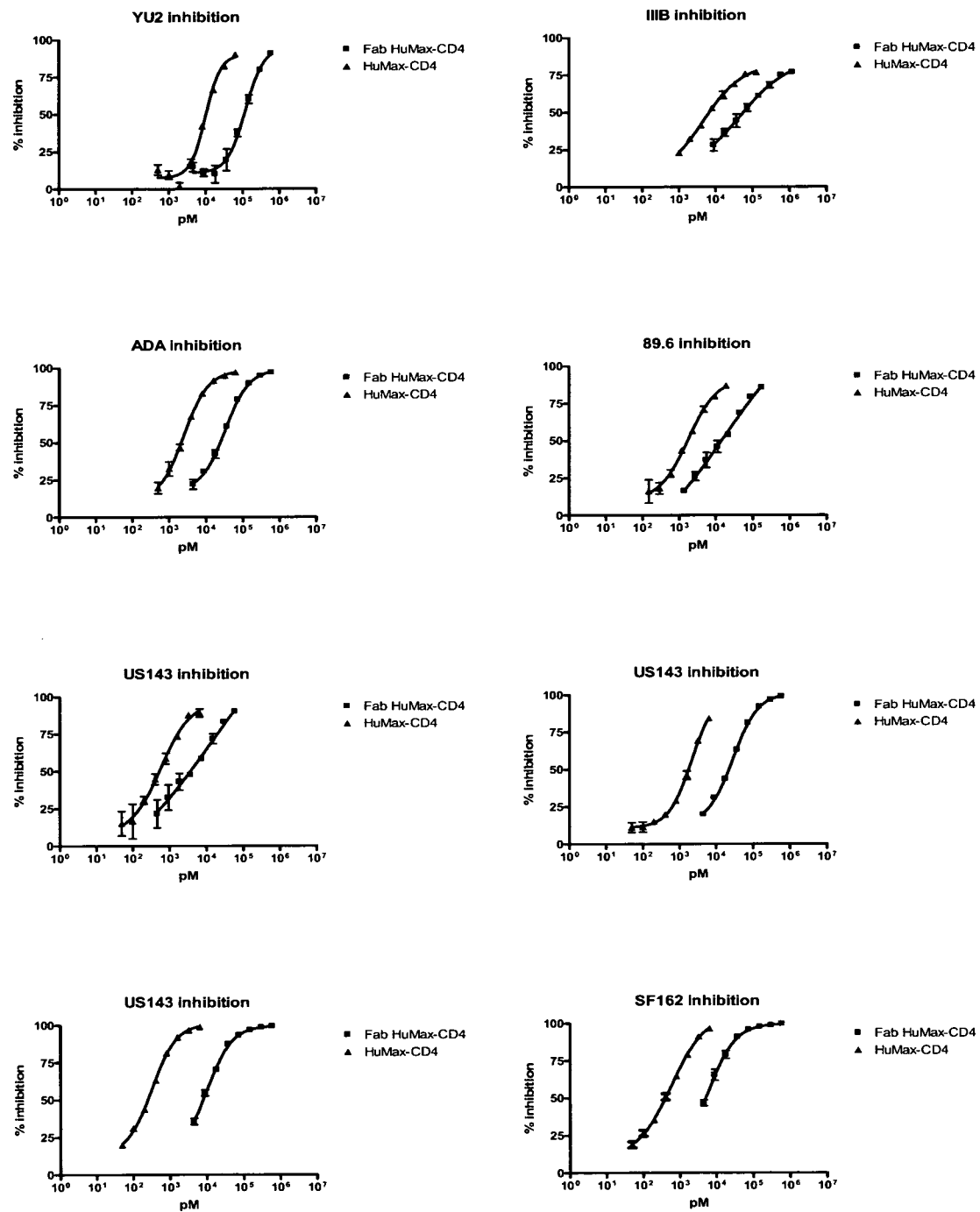

FIG. 27: The inhibition curves of HuMax-CD4 and the Fab fragments of HuMax-CD4 of the infection of several strains of HIV-1 of CD4-CCR5 or CD4-CXCR4 positive cells measured by luciferase activity (mean of triplicate measurements).

Figure 28:
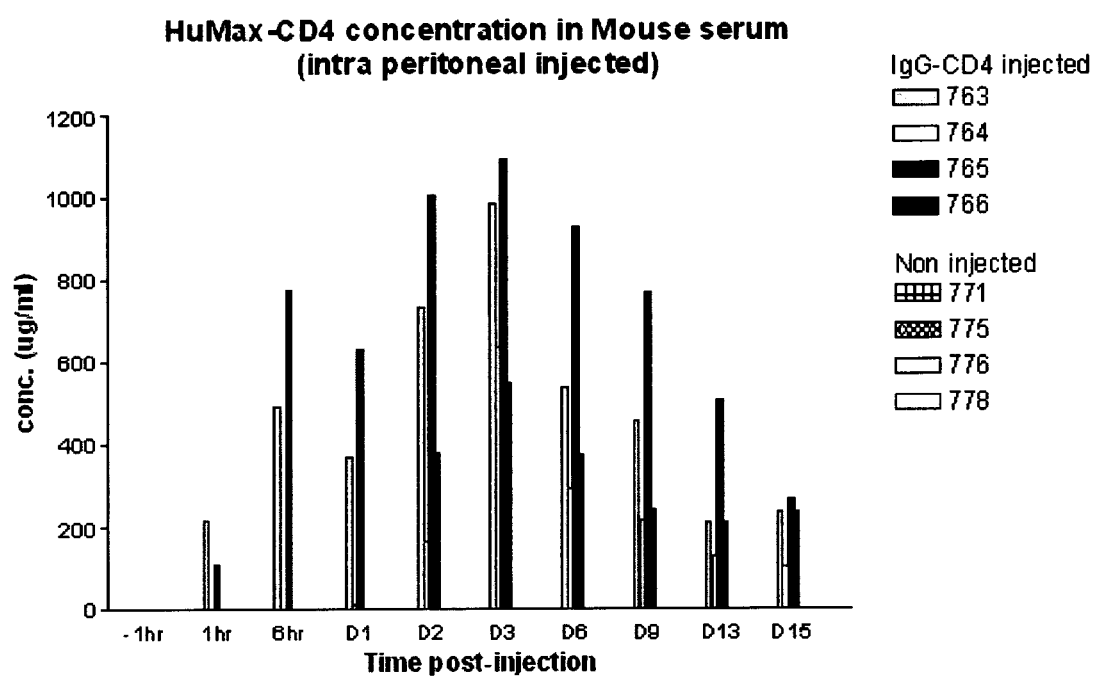

FIG. 28: The plasma HuMax-CD4 concentrations in time of the individual PBMC reconstituted mice treated intraperitoneally with HuMax-CD4, or non treated, and infected with HIV-1.

Figure 29:
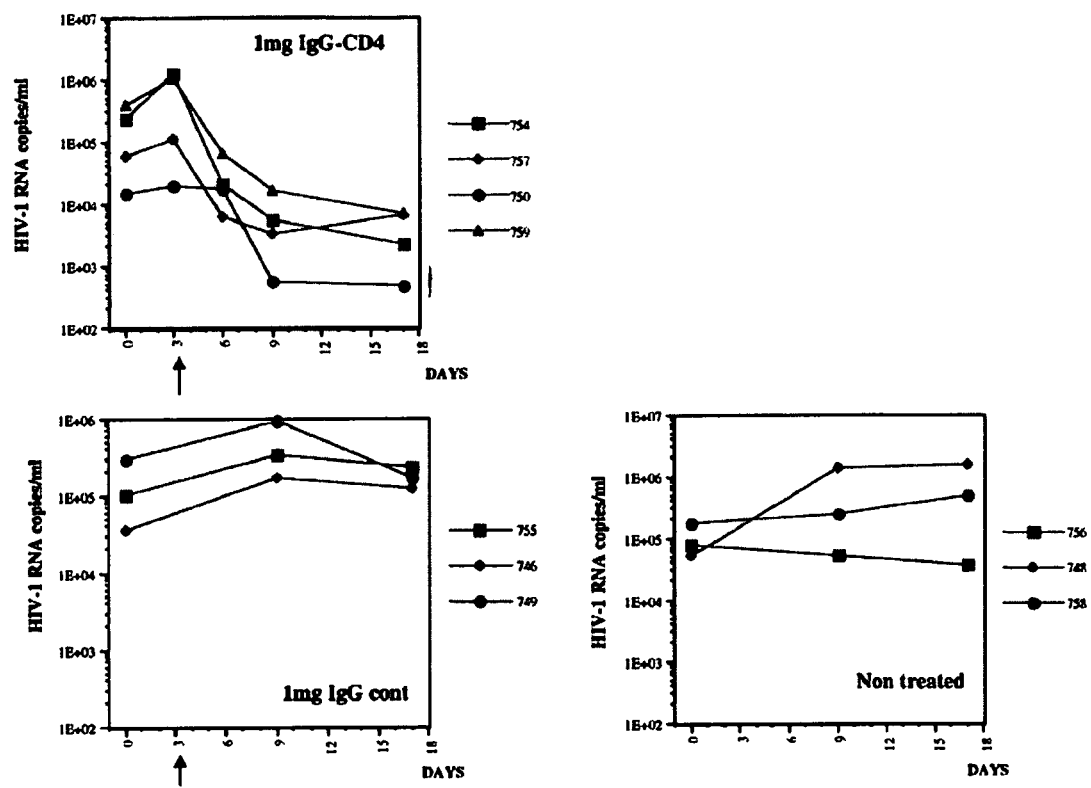

FIG. 29: The measured HIV-1 RNA copies in time of the individual PBMC reconstituted mice treated intraperitoneally with HuMax-CD4, of IgG control or non treated, and infected with HIV-1.

Figure 30:
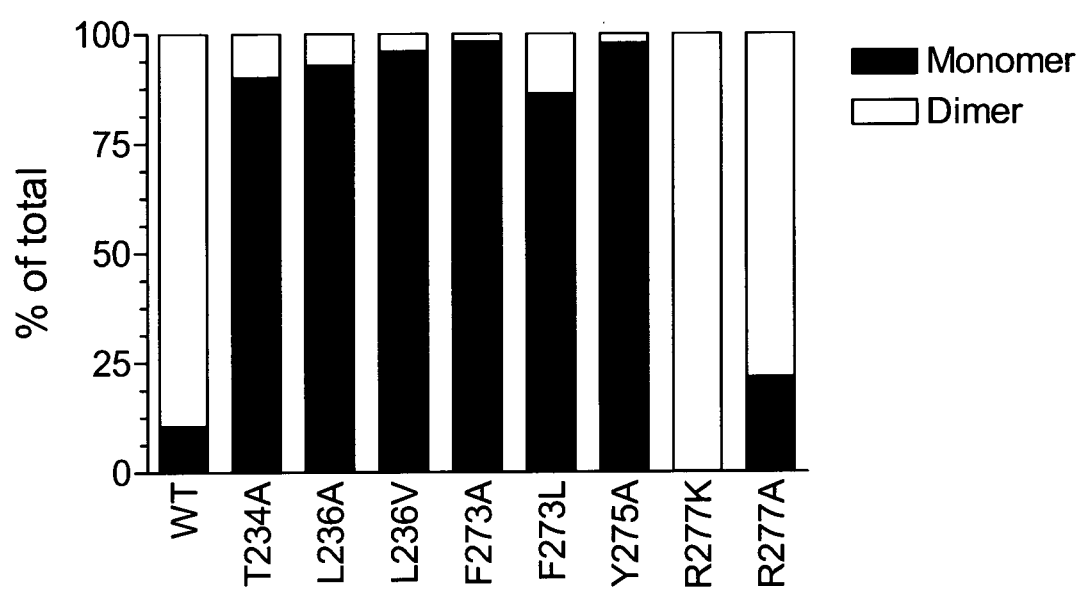

FIG. 30: Percentage of molecules present as monomers for each HG mutant tested using non-covalent nano-electrospray mass spectrometry. HG mutant samples were prepared in aqueous 50 mM ammonium acetate solutions at a concentration of 1 µM.

Figure 31:
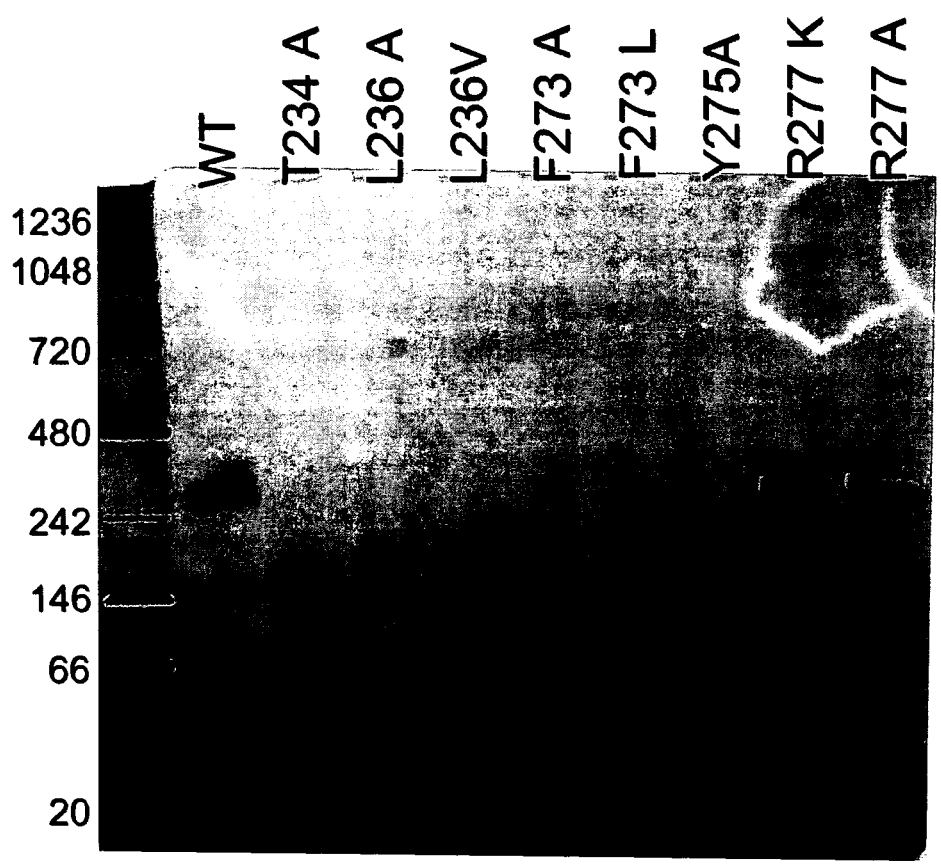

FIG. 31: NativePAGE™ Novex® Bis-Tris gel electrophoresis of CH3 mutants compared to 2F8-HG (WT) and R277K HG mutant control.

Figure 32:
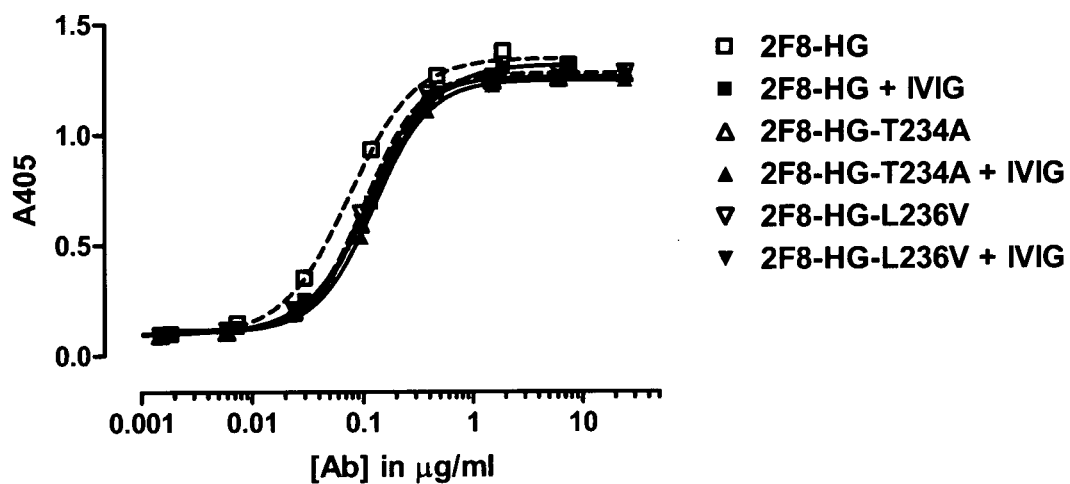

FIG. 32: The binding of 2F8-HG and CH3 mutants 2F8-HG-T234A and 2F8-HG-L236V was tested in EGFR ELISA in the presence and absence of polyclonal human IgG.

Figure 33:
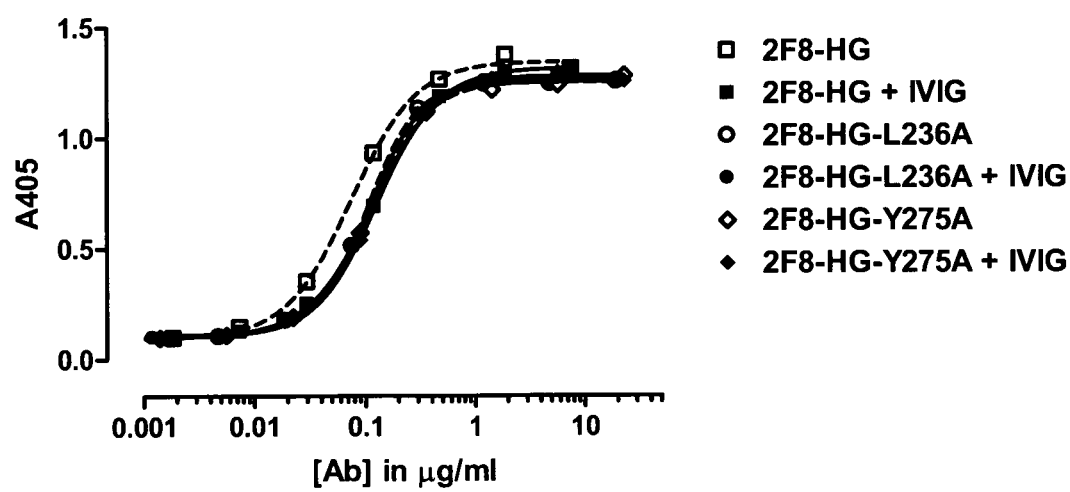

FIG. 33: The binding of 2F8-HG and CH3 mutants 2F8-HG-L236A and 2F8-HG-Y275A was tested in EGFR ELISA in the presence and absence of polyclonal human IgG.

FIG. 34: Dose-response curves showing the inhibition of EGF-induced EGFr phosphorylation in A431 cells by anti-EGFr 2F8-HG (WT) and CH3 mutants thereof.

Figure 35:
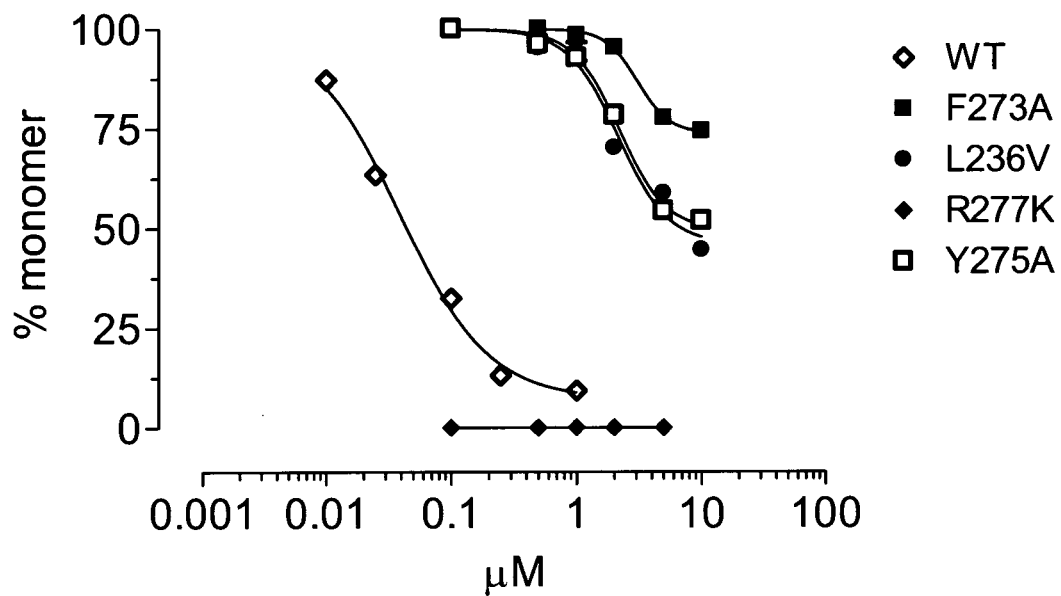

FIG. 35: Percentage molecules present as monomers at different molar concentrations of CH3 mutants compared to 2F8-HG (WT) and R277K. The Table shows EC50 values of monomer to dimer conversion, calculated for each CH3 mutant and 2F8-HG (WT) based on the curves presented in the figure.

Figure 36:
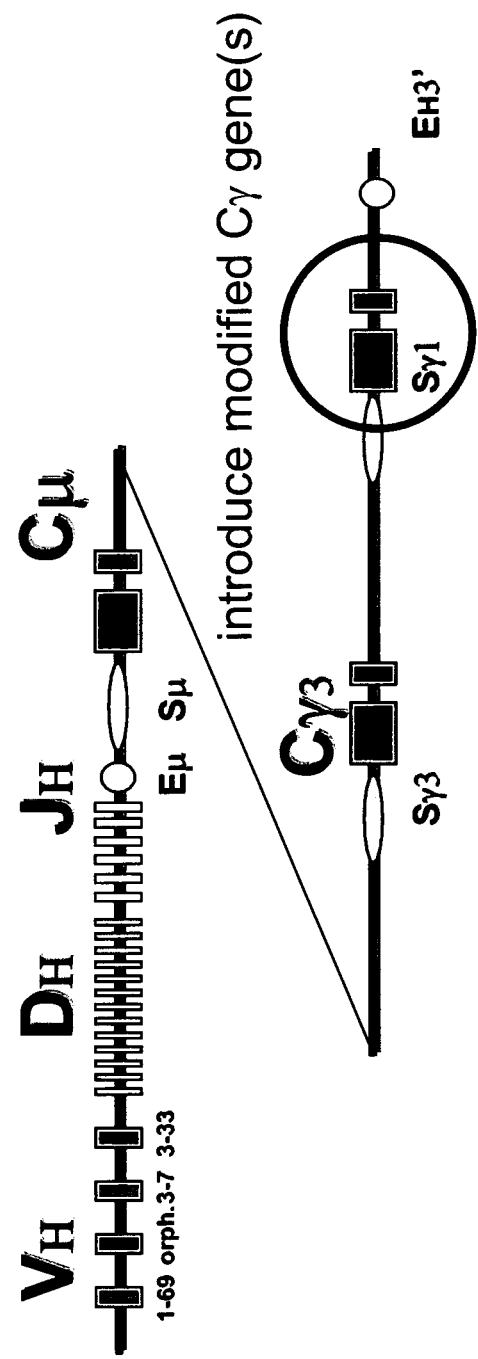

FIG. 36: Schematic overview of one possible embodiment of a heavy chain transgene according to the invention.

DETAILED DESCRIPTION OF THE SEQUENCE LISTINGS

SEQ ID No: 1: The nucleic acid sequence of $C_L$ kappa of human Ig
SEQ ID No: 2: The amino acid sequence of the kappa light chain of human Ig
SEQ ID No: 3: The nucleic acid sequence of $C_L$ lambda of human Ig SEQ ID No: 4: The amino acid sequence of the lambda light chain of human Ig SEQ ID No: 5: The nucleic acid sequence of the $V_H$ region of HuMab-7D8

SEQ ID No: 6: The amino acid sequence of the $V_H$ region of HuMab-7D8

SEQ ID No: 7: The nucleic acid sequence of the $V_H$ region of mouse anti-Betv-1

SEQ ID No: 8: The amino acid sequence for the $V_H$ region of mouse anti-Betv-1

SEQ ID No: 9: The nucleic acid sequence of the $V_L$ region of HuMab-7D8

SEQ ID No: 10: The amino acid sequence of the $V_L$ region of HuMab-7D8

SEQ ID No: 11: The nucleic acid sequence of the $V_L$ region of mouse anti-Betv1

SEQ ID No: 12: The amino acid sequence of the $V_L$ region of mouse anti-Betv1

SEQ ID No: 13: The nucleic acid sequence of the wildtype $C_H$ region of human IgG4

SEQ ID No: 14: The amino acid sequence of the wildtype CH region of human IgG4.

Sequences in italics represent the CH1 region, highlighted sequences represent the hinge region, regular sequences represent the CH2 region and underlined sequences represent the CH3 region.

SEQ ID No: 15: The nucleic acid sequence of the CH region of human IgG4 (SEQ ID No: 13) mutated in positions 714 and 722

SEQ ID No: 16: The amino acid sequence of the hingeless CH region of a human IgG4

SEQ ID NO: 17: The amino acid sequence of the lambda chain constant human (accession number S25751)

SEQ ID NO: 18: The amino acid sequence of the kappa chain constant human (accession number P01834)

SEQ ID NO: 19: The amino acid sequence of IgG1 constant region (accession number P01857). Sequences in italics represent the CH1 region, highlighted sequences represent the hinge region, regular sequences represent the CH2 region and underlined sequences represent the CH3 region SEQ ID NO: 20: The amino acid sequence of the IgG2 constant region (accession number P01859). Sequences in italics represent the CH1 region, highlighted sequences represent the hinge region, regular sequences represent the CH2 region and underlined sequences represent the CH3 region SEQ ID NO: 21: The amino acid sequence of the IgG3 constant region (accession number A23511). Sequences in italics represent the CH1 region, highlighted sequences represent the hinge region, regular sequences represent the CH2 region and underlined sequences represent the CH3 region SEQ ID NOs: 22 to 53 show oligonucleotide primers used for preparation of DNA constructs SEQ ID NO: 54: A peptide of a hingeless IgG4

SEQ ID NO: 55: A portion of the constant region of IgG4

SEQ ID NO: 56: A portion of the constant region of a hingeless IgG4

DETAILED DESCRIPTION OF THE INVENTION

The term "antibody" as referred to herein includes whole antibody molecules, antigen binding fragments, monovalent antibodies, and single chains thereof. Antibody molecules belong to a family of plasma proteins called immunoglobulins, whose basic building block, the immunoglobulin fold or domain, is used in various forms in many molecules of the immune system and other biological recognition systems. Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain may also have regularly spaced intrachain disulfide bridges. Each light chain is comprised of a light chain variable region (abbreviated herein as $V_L$) and a light chain constant region (abbreviated herein as $C_L$). Each heavy chain is comprised of a heavy chain variable region ($V_H$) and a heavy chain constant region ($C_H$) consisting of three domains, $C_H1$, $C_H2$ and $C_H3$, and the hinge region). The constant domain of the light chain is aligned with the first constant domain ($C_H1$) of the heavy chain, and the light chain variable domain is aligned with the variable domain of the heavy chain forming what is known as the "Fab fragment". $C_H1$ and $C_H2$ of the heavy chain are separated form each other by the so-called hinge region, which allows the Fab "arms" of the antibody molecule to swing to some degree. The hinge region normally comprises one or more cysteine residues, which are capable of forming disulphide bridges with the cysteine residues of the hinge region of the other heavy chain in the antibody molecule.

The variable regions of the heavy and light chains contain a binding domain that interacts with an antigen. The constant regions of the antibodies may mediate the binding of the immunoglobulin to host tissues or factors, including various cells of the immune system (for instance effector cells) and the first component (C1q) of the classical complement system Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), for instance IgG1, IgG2, IgG3 and IgG4; IgA1 and IgA2. The genes for the heavy chains constant domains that correspond to the different classes of immunoglobulins are called alpha (α), delta (δ), epsilon (ε), gamma (γ) and mu (μ), respectively. Immunoglobulin subclasses are encoded by different genes such as γ1, γ2, γ3 and γ4. The genes for the light chains of antibodies are assigned to one of two clearly distinct types, called kappa (K) and lambda (A), based on the amino sequences of their constant domain. The subunit structures and three-dimensional configurations of different classes of immunoglobulins are well known. Distinct allotypes of immunoglobulins exist within the human population such as G1m(a), G1m(x), G1m(f) and G1m(z) for IgG1 heavy chain and Km1, Km1,2 and Km3 for the kappa light chain. These allotypes differ at distinct amino acids in their region encoding the constant regions.

The term "human antibody", as used herein, is intended to include antibodies having variable and constant regions derived from human germline immunoglobulin sequences. The human antibodies of the invention may include amino acid residues not encoded by human germline immunoglobulin sequences (for instance mutations introduced by random or site-specific mutagenesis in vitro or by somatic mutation in vivo). However, the term "human antibody", as used herein, is not intended to include antibodies in which CDR1 or CDR2 sequences derived from the germline of another mammalian species, such as a mouse, or the CDR3 region derived from an antibody from another species, such as mouse, have been grafted onto human framework sequences.

The term "$K_D$" (M), as used herein, refers to the dissociation equilibrium constant of a particular antibody-antigen interaction.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

The term "nucleic acid", nucleic acid construct" or "nucleic acid molecule", as used herein, is intended to include DNA molecules and RNA molecules. A nucleic acid molecule may be single-stranded or double-stranded.

A nucleic acid is "operably linked" when it is placed into a functional relationship with another nucleic acid sequence. For instance, a promoter or enhancer is operably linked to a coding sequence if it affects the transcription of the sequence. For switch sequences, operably linked indicates that the sequences are capable of effecting switch recombination.

When reference is made to "physiological condition" it is meant a condition that exists in vivo, within the organism, or an in vivo condition which is recreated by fully or partially mimicking said in vivo condition, for example a water solution with an equivalent osmotic value as the blood.

The term "recombinant human antibody", as used herein, includes all human antibodies that are prepared, expressed, created or isolated by recombinant means, such as for instance (a) antibodies isolated from an animal (for instance a mouse) that is transgenic or transchromosomal for human immunoglobulin genes or a hybridoma prepared therefrom, (b) antibodies isolated from a host cell transformed to express the antibody, for instance from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. Such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "specific binding'" refers to the binding of an antibody, or antigen-binding fragment thereof, to a predetermined antigen. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when measured for instance using sulfon plasmon resonance on BIAcore or as apparent affinities based on $IC_{50}$ values in FACS or ELISA, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antigen binding peptide, so that when the $K_D$ of the antigen binding peptide is very low (that is, the antigen binding peptide is highly specific), then the amount with which the affinity for the antigen is lower than the affinity for a non-specific antigen may be at least 10,000 fold.

The terms "non-human transgenic animal" refers to a non-human animal having a genome comprising one or more human heavy and/or light chain transgenes or transchromosomes and which is capable of expressing human antibodies. For example, a transgenic mouse can have a human light chain transgene and either a human heavy chain transgene or human heavy chain transchromosome, such that the mouse produces human antibodies when immunized with an antigen and/or cells expressing an antigen. The human heavy chain transgene is can be integrated into the chromosomal DNA of the mouse, as is the case for transgenic, for instance HuMAb™ mice, such as HCo7 or HCo12 mice, or the human heavy chain transgene can be maintained extrachromosomally, as is the case for transchromosomal a KM-Mouse™ as described in WO 02/43478. Such transgenic and transchromosomal mice are capable of producing multiple isotypes of human monovalent antibodies binding to selected antigens (e.g., IgG, IgA and/or IgE) by undergoing V-D-J recombination and isotype switching.

The KM-Mouse™ contains a human heavy chain transchromosome and a human kappa light chain transgene. The endogenous mouse heavy and light chain genes also have been disrupted in the KM-Mouse™ such that immunization of the mice leads to production of human immunoglobulins rather than mouse immunoglobulins.

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368 (6474): 856-859). Accordingly, the mice exhibit reduced expression of mouse IgM or κ and in response to immunization, the introduced human heavy and light chain transgenes, undergo class switching and somatic mutation to generate high affinity human IgG κ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol. Vol.* 13: 65-93, and Harding, F. and Lonberg, N. (1995) *Ann. N.Y. Acad. Sci.* 764: 536-546). The preparation of HuMAb mice is described in detail in Taylor, L. et al. (1992) *Nucleic Acids Research* 20:6287-6295; Chen, J. et al. (1993) *International Immunology* 5: 647-656; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol. Vol.* 13:65-93; Harding, F. and Lonberg, N. (1995) *Ann. N.Y. Acad. Sci.* 764:536-546; Fishwild, D. et al. (1996) *Nature Biotechnology* 14:845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; WO 98/24884, WO 94/25585, WO 93/1227, WO 92/22645, WO 92/03918 and WO 01/09187.

XenoMouse™ Technology comprising transgenic mice capable of making fully human antibodies comprising Kappa light chain is described in U.S. Pat. No. 5,939,598. Abgenix in WO2003047336 (hereby incorporated by reference), presented a further version of their XenoMouse™ Technology, which relates to transgenic animals which bear one or more human lambda light chain loci in addition to the kappa light chain loci. These transgenic animals comprise a substantially complete human lambda light chain locus comprising V, J, and constant region genes, or a portion of said human lambda light chain locus, wherein said portion comprises at least 500 kb of said human lambda light chain locus.

Further methods for producing transgenic animals have been described in Animal Transgenesis and Cloning (2003) Louise-Marie Houdebine. John Wiley & Sons, Ltd., and in WO02/12437.

The term "valence of an antibody" means the maximum number of antigenic determinates with which the antibody can react. For example IgG antibodies contain two Fab regions and can bind two molecules of antigen or two identical sites on the same particle, and thus have a valence of two.

The term "monovalent antibody" means in the present context that an antibody molecule at most contains one Fab region and normally is capable of binding a single molecule of the antigen only, and thus is not able of antigen crosslinking.

The term "vector", as used herein, is intended to refer to a nucleic acid molecule capable of transporting and inducing replication of another nucleic acid to which it has been linked. One type of vector is a "plasmid", which refers to a circular double stranded DNA loop into which additional DNA segments may be ligated. Another type of vector is a viral vector, wherein additional DNA or RNA segments may be ligated into the viral genome. Certain vectors are capable of autonomous replication in a host cell into which they are introduced (for instance bacterial vectors having a bacterial origin of replication and episomal mammalian vectors). Other vectors (for instance non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (for instance replication defective retroviruses, adenoviruses and adeno-associated viruses), which serve equivalent functions.

Five different classes of immunoglobulins exist, i.e. IgM, IgD, IgG, IgA and IgE, and these classes can be distinguished by their C regions.

Within the IgG class of antibodies several subclasses exist, i.e. in human IgG1, IgG2, IgG3, and IgG4 (Jefferis, R. 1990. Molecular structure of human IgG subclasses. In The human IgG subclasses. F. Shakib, ed. Pergamon Press, Oxford, p. 15). Each IgG heavy chain is composed of structurally related peptide sequences (i.e. variable and constant region domains) that are encoded by distinct gene segments or exons. The hinge region linking the CH1 and CH2 domain is encoded by a separate exon. Each of the four IgG subclass heavy chains may be expressed in combination with either kappa or lambda light chains to give an essentially symmetrical molecule composed of two identical heavy chains and two identical kappa or lambda light chains. Comparison within the heavy chain defines the CH1, CH2 and CH3 homology regions. Comparisons between like homology regions of each of the four subclasses reveals >95% sequence identity (Jefferis, R. 1990. F. Shakib, ed. Pergamon Press, Oxford, p. 15). The sequence between the CH1 and CH2 domains is referred to as the hinge region because it allows molecular flexibility. The CH3 domains are paired and the non-covalent interactions are sufficient for the IgG molecule to maintain its structural integrity following reduction of the inter-heavy chain disulphide bridges under mild conditions. CH3 domain pairing is compact and similar to pairing in the Fab, with a nearly exact dyad between the two domains (Saphire, et al., 2002. *J Mol Biol* 319:9). This is in contrast to the CH2 domains, which do not associate closely and their contact is primarily mediated by the two carbohydrate chains attached to the Asn297 residues (Saphire, et al., 2002. *J Mol Biol* 319:9).

The characteristic IgG structure in which two heavy-light chain heterodimers are linked is thus maintained by the inter-heavy chain disulphide bridges of the hinge region and the non-covalent interactions of the CH3 domains.

The interaction in the CH3 region has shown to be important in IgG1. Ig half-molecules, which have a dimeric configuration consisting of only one light chain and only one heavy chain, have been described as the result of rare deletions in human and murine plasmacytomas. Several patients suffering from extramedullary soft-tissue plasmacytoma, Waldenström macroglobulinemia, plasma cell leukemia and multiple myeloma, excreted IgG half molecules into their urine. Half-molecules were also found to be present in their serum. Studies on the biochemical nature of these half-molecules showed that they consist of IgG1 molecules in which the heavy chain $C_H1$, hinge and $C_H2$ regions appeared normal, whereas deletions were found in the $C_H3$ region.

We show in this application that removal of the hinge region in IgG4 results in the formation of monovalent antibodies in which the linkage between the two heavy-light chain heterodimers is lost or diminished. Consequently, changes in hinge region disulphide bridges of other IgG subclasses alone or in combination with mutations in the CH3 domain interactions may result in the formation of monovalent antibodies for these other subclasses as well.

The monovalent human antibodies produced by the non-human transgenic animals of the present invention have the advantage of having a long half-life in vivo, leading to a longer therapeutic window, as compared to e.g. a Fab fragment of the same antibody which has a considerably shorter half-life in vivo.

These antibodies are suitable for therapeutic applications, wherein blocking of an antigen-mediated activity requires monovalent antibody binding (absence of cross-linking).

In a first main aspect, the invention relates to a non-human transgenic animal, which upon antigenic stimulation is capable of producing a monovalent antibody binding to a selected antigen, which monovalent antibody comprises a heavy chain, which heavy chain comprises
 (i) a human $V_H$ region, and
 (ii) a human $C_H$ region, wherein the $C_H$ region has been modified such that the region corresponding to the hinge region and, optionally other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

Said optional modification of other regions of the $C_H$ region, such as the $C_H3$ region is most relevant if the $C_H$ region is of a non-IgG4 isotype, such as an IgG1, IgG2 or IgG3 isotype, because in these other isotypes, inter-heavy chain bonds, in particular non-covalent bonds could potentially keep the antibody in a divalent form, even in the absence of cysteines in the hinge region.

The non-human transgenic animals according to the present invention have not been modified in a way that is likely to cause them suffering without any substantial medical benefit to man or animal.

In one embodiment, the non-human transgenic animal of the invention is capable of producing a monovalent antibody, which further comprises a light chain, which light chain comprises
(i) a human $V_L$ region, and
(ii) a human $C_L$ region, which optionally has been modified such that the $C_L$ region does not contain any amino acids, which are capable of forming disulfide bonds with an identical $C_L$ region or other covalent bonds with an identical $C_L$ region in the presence of polyclonal human IgG.

Said optional modification of the $C_L$ region is most relevant if the $C_H$ region is of the IgG1 isotype, because in an IgG1, a free cysteine residue of the light chain could potentially keep the antibody in a divalent form, even in the absence of cysteines in the hinge region.

In a further embodiment, the non-human transgenic animal comprises in its genome a heavy chain transgene comprising, in operable linkage,
(i) a plurality of human V genes, a plurality of human D genes, a plurality of human J genes,
(ii) a plurality of human $C_H$ genes and associated isotype switch sequences, comprising a human µ $C_H$ gene and at least one modified γ $C_H$ gene,
wherein the transgene undergoes productive VDJ rearrangement and isotype switching in the lymphocytes of the animal. ("modified" herein above refers to the hinge and optional other $C_H$ modifications defined above in the main first aspect of the invention).

In an even further embodiment, the non-human transgenic animal comprises a κ light chain transgene comprising
(i) a plurality of human κ V genes, a plurality of human κ J genes, and
(ii) a human κ $C_L$ gene, which optionally, in particular if the $C_H$ region is of the IgG1 isotype, contains the modification as defined above.

In an even further embodiment, the non-human transgenic animal comprises a λ light chain transgene comprising
(i) a plurality of human λ V genes, at least one human λ J gene, and
(ii) at least one human λ $C_L$ gene, which optionally, in particular if the $C_H$ region is of the IgG1 isotype, contains the modification as defined above.

In a further main aspect, the invention relates to a non-human transgenic animal, which upon antigenic stimulation is capable of producing a monovalent IgG4 antibody binding to a selected antigen, which monovalent antibody comprises
a heavy chain, which heavy chain comprises
(i) a human $V_H$ region, and
(ii) a human $C_H$ region, wherein the $C_H$ region has been modified such that the region corresponding to the hinge region does not comprise any amino acid residues, which are capable of forming disulfide bonds with an identical $C_H$ region, and
a light chain, which light chain comprises
(i) a human $V_L$ region, and
(ii) a human $C_L$ region.

In one embodiment hereof, the animal comprises in its genome,
(i) a heavy chain transgene comprising, in operable linkage,
a plurality of human V genes, a plurality of human D genes, a plurality of human J genes, and
a plurality of human $C_H$ genes and associated isotype switch sequences, comprising a human µ $C_H$ gene and at least one hinge modified Cγ4 gene, and
(iia) a κ light chain transgene comprising, in operable linkage,
a plurality of human κ V genes, a plurality of human κ J genes, and
a human κ $C_L$ gene, and/or
(iib) a λ light chain transgene comprising, in operable linkage,
a plurality of human λ V genes, at least one human λ J gene, and
at least one human λ $C_L$ gene,
wherein the transgene undergoes productive V(D)J rearrangement and isotype switching in the lymphocytes of the animal.

In a further main aspect, the invention relates to a non-human transgenic animal, which upon antigenic stimulation is capable of producing a monovalent IgG4 antibody binding to a selected antigen, which monovalent antibody comprises
a heavy chain, which heavy chain comprises
(i) a human $V_H$ region, and
(ii) a human $C_H$ region, wherein the $C_H$ region has been modified such that the region corresponding to the hinge region does not comprise any amino acid residues which are capable of forming disulfide bonds with an identical $C_H$ region, and wherein the $C_H3$ region has the sequence as set forth in SEQ ID NO: 16, but wherein the $C_H3$ region has been modified so that one or more of the following amino acid substitutions have been made: Thr (T) in position 234 has been replaced by Ala (A); Leu (L) in position 236 has been replaced by Ala (A); Leu (L) in position 236 has been replaced by Val (V); Phe (F) in position 273 has been replaced by Ala (A); Phe (F) in position 273 has been replaced by Leu (L); Tyr (Y) in position 275 has been replaced by Ala (A); Arg (R) in position 277 has been replaced by Ala (A),
and
a light chain, which light chain comprises
(i) a human $V_L$ region, and
(ii) a human $C_L$ region.

In one embodiment hereof, the animal comprises in its genome,
(i) a heavy chain transgene comprising, in operable linkage,
a plurality of human V genes, a plurality of human D genes, a plurality of human J genes, and
a plurality of human $C_H$ genes and associated isotype switch sequences, comprising a human µ $C_H$ gene and at least one modified Cγ4 gene, and
(iia) a κ light chain transgene comprising, in operable linkage,
a plurality of human κ V genes, a plurality of human κ J genes, and
a human κ $C_L$ gene, and/or
(iib) a λ light chain transgene comprising, in operable linkage,
a plurality of human λ V genes, at least one human λ J gene, and
at least one human λ $C_L$ gene,
wherein the transgene undergoes productive V(D)J rearrangement and isotype switching in the lymphocytes of the animal.

In a further main aspect, the invention relates to a non-human transgenic animal, which upon antigenic stimulation is capable of producing a monovalent IgG1 antibody binding to a selected antigen, which monovalent antibody comprises a heavy chain, which heavy chain comprises
(i) a human $V_H$ region, and
(ii) a human $C_H$ region, wherein the $C_H$ region has been modified such that the region corresponding to the hinge region and the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG, and a light chain, which light chain comprises
(i) a human $V_L$ region, and
(ii) a human $C_L$ region, which has been modified such that the $C_L$ region does not contain any amino acids, which are capable of forming disulfide bonds with an identical $C_L$ region or other covalent bonds with an identical $C_L$ region in the presence of polyclonal human IgG.

In one embodiment hereof, the animal comprises in its genome,
(i) a heavy chain transgene comprising, in operable linkage,
a plurality of human V genes, a plurality of human D genes, a plurality of human J genes, and
a plurality of human $C_H$ genes and associated isotype switch sequences, comprising a human μ $C_H$ gene and at least one modified Cγ1 gene, and
(iia) a κ light chain transgene comprising, in operable linkage,
a plurality of human κ V genes, a plurality of human κ J genes, and
a modified human κ $C_L$ gene, and/or
(iib) a λ light chain transgene comprising, in operable linkage,
a plurality of human λ V genes, at least one human λ J gene, and
at least one modified human λ $C_L$ gene,
wherein the transgene undergoes productive V(D)J rearrangement and isotype switching in the lymphocytes of the animal.

In a further embodiment hereof, the animal is further capable of producing an IgG4 monovalent antibody as defined herein.

In another embodiment of the non-human transgenic animal according to invention, the endogenous animal immunoglobulin heavy chain gene locus has been inactivated. Alternatively, or in addition, the endogenous animal immunoglobulin κ light chain gene locus and/or the endogenous animal immunoglobulin λ light chain gene locus has been inactivated.

In another embodiment of the non-human transgenic animal according to invention, the human γ $C_H$ gene is in closer proximity to the human μ $C_H$ gene than in a naturally occurring human immunoglobulin heavy chain gene locus.

In one embodiment of the non-human transgenic animal according the invention, the heavy chain transgene encodes a $C_H$ region of the IgG1 isotype comprising the $C_H3$ region as set as set forth in SEQ ID NO: 19, but wherein the $C_H3$ region has been modified so that one or more of the following amino acid substitutions have been made: Arg (R) in position 238 has been replaced by Gln (Q); Asp (D) in position 239 has been replaced by Glu (E); Thr (T) in position 249 has been replaced by Ala (A); Leu (L) in position 251 has been replaced by Ala (A); Leu (L) in position 251 has been replaced by Val (V); Phe (F) in position 288 has been replaced by Ala (A); Phe (F) in position 288 has been replaced by Leu (L); Tyr (Y) in position 290 has been replaced by Ala (A); Lys (K) in position 292 has been replaced by Arg (R); Lys (K) in position 292 has been replaced by Ala (A); Gln (Q) in position 302 has been replaced by Glu (E); and Pro (P) in position 328 has been replaced by Leu (L).

In a further embodiment hereof, one or more of the following amino acid substitutions have been made: Arg (R) in position 238 has been replaced by Gln (Q); Asp (D) in position 239 has been replaced by Glu (E); Lys (K) in position 292 has been replaced by Arg (R); Gln (Q) in position 302 has been replaced by Glu (E); and Pro (P) in position 328 has been replaced by Leu (L).

In an even further embodiment hereof,
(i) Arg (R) in position 238 has been replaced by Gln (Q),
(ii) Arg (R) in position 238 has been replaced by Gln (Q), and Pro (P) in position 328 has been replaced by Leu (L), or
(iii) all 9 amino acids mentioned above have been substituted.

In another further embodiment, the heavy chain transgene further encodes the $C_H1$ and/or $C_H2$ regions as set forth in SEQ ID NO: 19.

In yet another further embodiment, the light chain transgene encodes the kappa $C_L$ region having the amino acid sequence as set forth in SEQ ID NO: 18, but wherein the sequence has been modified so that the terminal cysteine residue in position 106 has been replaced with another amino acid residue or has been deleted.

In a different further embodiment, the light chain transgene encodes the lambda $C_L$ region having the amino acid sequence as set forth in SEQ ID NO: 17, but wherein the sequence has been modified so that the cysteine residue in position 104 has been replaced with another amino acid residue or has been deleted.

In an even further different embodiment, the heavy chain transgene further encodes the $C_H1$ region as set forth in SEQ ID NO: 19, but wherein the $C_H1$ region has been modified so that Ser (S) in position 14 has been replaced by a cysteine residue.

In one embodiment of the non-human transgenic animal according the invention, the heavy chain transgene encodes a $C_H$ region of the IgG2 isotype comprising the $C_H3$ region as set forth in SEQ ID NO: 20, but wherein the $C_H3$ region has been modified so that one or more of the of the following amino acid substitutions have been made: Arg (R) in position 234 has been replaced by Gln (Q); Thr (T) in position 245 has been replaced by Ala (A); Leu (L) in position 247 has been replaced by Ala (A); Leu (L) in position 247 has been replaced by Val (V); Met (M) in position 276 has been replaced by Val (V); Phe (F) in position 284 has been replaced by Ala (A); Phe (F) in position 284 has been replaced by Leu (L); Tyr (Y) in position 286 has been replaced by Ala (A); Lys (K) in position 288 has been replaced by Arg (R); Lys (K) in position 288 has been replaced by Ala (A); Gln (Q) in position 298 has been replaced by Glu (E); and Pro (P) in position 324 has been replaced by Leu (L).

In a further embodiment hereof, the heavy chain transgene further encodes the $C_H1$ and/or $C_H2$ regions as set forth in SEQ ID NO: 20.

In one embodiment of the non-human transgenic animal according the invention, the heavy chain transgene encodes a $C_H$ region of the IgG3 isotype comprising the $C_H3$ region as set forth in SEQ ID NO: 21, but wherein the $C_H3$ region has been modified so that one or more of the following amino acid substitutions have been made: Arg (R) in position 285 has been replaced by Gln (Q); Thr (T) in position 296 has been replaced by Ala (A); Leu (L) in position 298 has been replaced by Ala (A); Leu (L) in position 298 has been replaced by Val (V); Ser (S) in position 314 has been replaced by Asn (N); Asn (N) in position 322 has been replaced by Lys (K); Met (M) in position 327 has been replaced by Val (V); Phe (F) in position 335 has been replaced by Ala (A); Phe (F) in position 335 has been replaced by Leu (L); Tyr (Y) in position 337 has been replaced by Ala (A); Lys (K) in position 339 has been replaced by Arg (R); Lys (K) in position 339 has been replaced by Ala (A); Gln (Q) in position 349 has been replaced by Glu (E); Ile (I) in position 352 has been replaced by Val (V); Arg (R) in position 365 has been replaced by His (H); Phe (F) in position 366 has been replaced by Tyr (Y); and Pro (P) in position 375 has been replaced by Leu (L).

In a further embodiment hereof, the heavy chain transgene further encodes the $C_H1$ and/or $C_H2$ regions as set forth in SEQ ID NO: 21.

The hinge region is a region of an antibody situated between the $C_H1$ and $C_H2$ regions of the constant domain of the heavy chain. The extent of the hinge region is determined by the separate exon, which encodes the hinge region. The hinge region is normally involved in participating in ensuring the correct assembly of the four peptide chains of an antibody into the traditional tetrameric form via the formation of disulphide bonds, or bridges, between one or more cysteine residues in the hinge region of one of the heavy chains and one or more cysteine residues in the hinge region of the other heavy chain. A modification of the hinge region so that none of the amino acid residues in the hinge region are capable of participating in the formation of disulphide bonds may thus for instance comprise the deletion and/or substitution of the cysteine residues present in the unmodified hinge region. A region corresponding to the hinge region should for the purpose of this specification be construed to mean the region between region $C_H1$ and $C_H2$ of a heavy chain of an antibody. In the context of the present invention, such a region may also comprise no amino acid residues at all, corresponding to a deletion of the hinge region, resulting in the $C_H1$ and $C_H2$ regions being connected to each other without any intervening amino acid residues. Such a region may also comprise only one or a few amino acid residues, which residues need not be the amino acid residues present in the N- or C-terminal of the original hinge region.

In a further embodiment of any of the above mentioned non-human transgenic animals, the heavy chain transgene encodes a $C_H$ region, which has been modified such that the region corresponding to the hinge region of the $C_H$ region does not comprise any cysteine residues.

In another embodiment, the heavy chain transgene encodes a $C_H$ region, which has been modified such that the amino acids corresponding to the amino acids 106 and 109 of the $C_H$ sequence of SEQ ID No: 14 have been deleted.

In another embodiment, the heavy chain transgene encodes a $C_H$ region, which has been modified such that one of the amino acid residues corresponding to amino acids 106 and 109 of the $C_H$ sequence of SEQ ID No: 14 has been substituted with an amino acid residue different from cysteine, and the other of the amino acid residues corresponding to amino acid residues 106 and 109 of the sequence of SEQ ID No: 14 has been deleted.

In another embodiment, the heavy chain transgene encodes a $C_H$ region, which has been modified such that the amino acid residue corresponding to amino acid residue 106 has been substituted with an amino acid residue different from cysteine, and the amino acid residue corresponding to amino acid residue 109 has been deleted.

In another embodiment, the heavy chain transgene encodes a $C_H$ region, which has been modified such that the amino acid residue corresponding to amino acid residue 106 has been deleted, and the amino acid residue corresponding to amino acid residue 109 has been substituted with an amino acid residue different from cysteine.

In another embodiment, the heavy chain transgene encodes a $C_H$ region, which has been modified such that at least the amino acid residues corresponding to amino acid residues 106 to 109 of the $C_H$ sequence of SEQ ID No: 14 have been deleted.

In another embodiment, the heavy chain transgene encodes a $C_H$ region, which has been modified such that at least the amino acid residues corresponding to amino acid residues 99 to 110 of the sequence of SEQ ID No: 14 have been deleted.

In another embodiment, the heavy chain transgene encodes a $C_H$ region as set forth in SEQ ID No: 16.

In another embodiment, the heavy chain transgene encodes a $C_H$ region, which has been modified such that the entire hinge region has been deleted.

In a different embodiment of the invention, the transgenic animal does not comprise a human Cγ4 gene.

In another embodiment of the invention, the transgenic animal does not comprise a human Cγ4 gene, which has been modified to delete the sequence encoding the hinge region.

In a further embodiment of the invention, the animal is capable of producing a monovalent antibody which binds to the selected antigen, such as c-Met, with a dissociation constant ($k_d$) of $10^{-7}$ M or less, such as $10^{-8}$ M, $10^{-9}$ M, $10^{-10}$ M or $10^{-11}$ M or less.

In one embodiment, the non-human transgenic animal according to the invention is a mammal, such as a camelidae, for example a llama or camel, or a rodent, for example a mouse, rabbit, guinea pig or a rat.

For example, in one embodiment, the animal is a mouse, such as mouse derived from strain C57BL/6J, CBA/J, DBA/2J, 129/sv or SJL/J.

In a further main aspect, the invention relates to a heavy chain transgene comprising
(i) a plurality of human V genes, a plurality of human D genes, a plurality of human J genes,
(ii) a plurality of human $C_H$ genes and associated isotype switch sequences, comprising a human μ $C_H$ gene and at least one modified γ $C_H$ gene, wherein the human γ $C_H$ gene is in closer proximity to the human μ $C_H$ gene than in a naturally occurring human immunoglobulin heavy chain gene locus.

A non-limiting example of an embodiment of the transgene of the invention is shown schematically in FIG. 36.

A DNA construct comprising the transgene according to the invention may be prepared synthetically by established standard methods, for instance the phosphoamidine method described by Beaucage et al., Tetrahedron Lett. 22, 1859-1869 (1981), or the method described by Matthes et al., EMBO J. 3, 801-805 (1984). According to the phosphoamidine method, oligonucleotides are synthesised, for instance in an automatic DNA synthesizer, purified, annealed, ligated and cloned in suitable vectors.

A DNA sequence encoding the may also be of genomic or cDNA origin, for instance obtained by preparing a genomic or cDNA library and screening for DNA sequences coding for all or part of the antibody by hybridization using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al. Science 239, 487-491 (1988).

In another main aspect, the invention relates to a method of producing a monovalent antibody binding to a selected antigen comprising
(i) immunizing the animal of the invention with a selected antigen, a cell expressing a selected antigen, or a nucleic acid construct encoding a selected antigen or a combination thereof
(ii) obtaining B cells from the transgenic animal expressing monovalent antibodies binding to the selected antigen,
(iii) optionally generating hybridomas from said B cells,
(iv) testing the monovalent antibodies produced by the B cells or hybridomas for binding to the selected antigen, and (v) identifying one or more monovalent antibodies capable of binding to the selected antigen.

In one embodiment hereof, the method comprises the further steps of (vi) identifying the coding sequences for said monovalent antibodies and (vii) producing said monovalent antibodies in a recombinant expression system.

In another embodiment, said method comprises step (iii) and the further steps of (vi) producing and purifying said monovalent antibodies from the hybridomas.

In one embodiment, the antigen is a human protein molecule. In a preferred embodiment hereof, the antigen is selected from VEGF, c-Met, CD20, CD38, IL-8, CD25, CD74, FcalphaRI, FcepsilonRI, acetyl choline receptor, fas, fasL, TRAIL, hepatitis virus, hepatitis C virus, envelope E2 of hepatitis C virus, tissue factor, a complex of tissue factor and Factor VII, EGFr, CD4, and CD28.

In a further main aspect, the invention relates to the use of a non-human transgenic animal of the invention as defined herein for generating a monovalent human antibody.

In a further main aspect, the invention relates to a monovalent antibody obtained or obtainable by the method described above.

In one embodiment, the monovalent antibody comprises a heavy chain, which heavy chain comprises
  (i) a human $V_H$ region, and
  (ii) a human $C_H$ region, wherein the $C_H$ region has been modified such that the region corresponding to the hinge region does not comprise any amino acid residues which are capable of forming disulfide bonds with an identical $C_H$ region, and wherein the $C_H3$ region has the sequence as set forth in SEQ ID NO: 16, but wherein the $C_H3$ region has been modified so that one or more of the following amino acid substitutions have been made: Thr (T) in position 234 has been replaced by Ala (A); Leu (L) in position 236 has been replaced by Ala (A); Leu (L) in position 236 has been replaced by Val (V); Phe (F) in position 273 has been replaced by Ala (A); Phe (F) in position 273 has been replaced by Leu (L); Tyr (Y) in position 275 has been replaced by Ala (A); Arg (R) in position 277 has been replaced by Ala (A),
and
a light chain, which light chain comprises
  (i) a human $V_L$ region, and
  (ii) a human $C_L$ region.

In a further main aspect the invention relates to a monovalent IgG4 antibody that binds to a selected antigen, which monovalent antibody comprises
a heavy chain, which heavy chain comprises
  (i) a human $V_H$ region, and
  (ii) a human $C_H$ region, wherein the $C_H$ region has been modified such that the region corresponding to the hinge region does not comprise any amino acid residues which are capable of forming disulfide bonds with an identical $C_H$ region, and wherein the $C_H3$ region has the sequence as set forth in SEQ ID NO: 16, but wherein the $C_H3$ region has been modified so that one or more of the following amino acid substitutions have been made: Thr (T) in position 234 has been replaced by Ala (A); Leu (L) in position 236 has been replaced by Ala (A); Leu (L) in position 236 has been replaced by Val (V); Phe (F) in position 273 has been replaced by Ala (A); Phe (F) in position 273 has been replaced by Leu (L); Tyr (Y) in position 275 has been replaced by Ala (A); Arg (R) in position 277 has been replaced by Ala (A),
and
a light chain, which light chain comprises
  (i) a human $V_L$ region, and
  (ii) a human $C_L$ region.

This antibody may be obtained from a non-human transgenic animal of the invention or may be produced by recombinant expression techniques well known in the art.

In one embodiment, the monovalent antibody comprises the CH3 region as set forth in SEQ ID NO: 16.

In another embodiment, the monovalent antibody comprises the CH3 region as set forth in SEQ ID NO: 16, but Glu (E) in position 225 has been replaced by Ala (A).

In another embodiment, the monovalent antibody comprises the CH3 region as set forth in SEQ ID NO: 16, but Thr (T) in position 234 has been replaced by Ala (A).

In another embodiment, the monovalent antibody comprises the CH3 region as set forth in SEQ ID NO: 16, but Leu (L) in position 236 has been replaced by Ala (A).

In another embodiment, the monovalent antibody comprises the CH3 region as set forth in SEQ ID NO: 16, but Leu (L) in position 236 has been replaced by Val (V).

In another embodiment, the monovalent antibody comprises the CH3 region as set forth in SEQ ID NO: 16, but Leu (L) in position 236 has been replaced by Glu (E).

In another embodiment, the monovalent antibody comprises the CH3 region as set forth in SEQ ID NO: 16, but Leu (L) in position 236 has been replaced by Gly (G).

In another embodiment, the monovalent antibody comprises the CH3 region as set forth in SEQ ID NO: 16, but Lys (K) in position 238 has been replaced by Ala (A).

In another embodiment, the monovalent antibody comprises the CH3 region as set forth in SEQ ID NO: 16, but Asp (D) in position 267 has been replaced by Ala (A).

In another embodiment, the monovalent antibody comprises the CH3 region as set forth in SEQ ID NO: 16, but Phe (F) in position 273 has been replaced by Ala (A).

In another embodiment, the monovalent antibody comprises the CH3 region as set forth in SEQ ID NO: 16, but Phe (F) in position 273 has been replaced by Leu (L).

In another embodiment, the monovalent antibody comprises the CH3 region as set forth in SEQ ID NO: 16, but Phe (F) in position 273 has been replaced by Asp (D) and/or Tyr (Y) in position 275 has been replaced by Glu (E).

In another embodiment, the monovalent antibody comprises the CH3 region as set forth in SEQ ID NO: 16, but Phe (F) in position 273 has been replaced by Thr (T) and/or Tyr (Y) in position 275 has been replaced by Glu (E).

In another embodiment, the monovalent antibody comprises the CH3 region as set forth in SEQ ID NO: 16, Tyr (Y) in position 275 has been replaced by Ala (A).

In another embodiment, the monovalent antibody comprises the CH2 region as set forth in SEQ ID NO: 16, but Thr (T) in position 118 has been replaced by Gln (Q) and/or Met (M) in position 296 has been replaced by Leu (L).

In another embodiment, the monovalent antibody comprises the CH2 region as set forth in SEQ ID NO: 16, but one, two or all three of the following substitutions have been made: Met (M) in position 120 has been replaced by Tyr (Y); Ser (S) in position 122 has been replaced by Thr (T); and Thr (T) in position 124 has been replaced by Glu (E).

In another embodiment, the monovalent antibody comprises the CH2 region as set forth in SEQ ID NO: 16, but wherein Asn (N) in position 302 has been replaced by Ala (A).

In another embodiment, the monovalent antibody comprises the CH2 region as set forth in SEQ ID NO: 16, but wherein Asn (N) in position 302 has been replaced by Ala (A) and Thr (T) in position 175 has been replaced by Ala (A) and Glu (E) in position 248 has been replaced by Ala (A).

In a further embodiment, the monovalent antibody comprises two or more of the above mentioned substitutions.

In a further main aspect, the invention relates to method for producing a non-human transgenic animal of the invention, said method comprising
(i) introducing into the embryonic stem cells of a non-human animal, a heavy chain transgene construct according to the invention, and optionally a light chain transgene capable of producing a light chain as defined above,
(ii) selecting embryonic stem cells expressing the transgene(s),
(iii) injecting the transformed embryonic stem cells into the inner mass of a blastocyst,
(iv) implanting the blastocysts into the uterus or oviduct of a non-human pseudopregnant female animal,
(v) testing the offspring for the presence of the transgene(s), and
(vi) mating two heterozygous offspring to produce homozygous transgenic strain of the non-human animal.

In a further main aspect, the invention relates to method for producing a non-human transgenic animal according to the invention, said method comprising
(i) injecting into the pronucleus of a fertilized ovum, such as the male pronucleus of a fertilized ovum, of a non-human animal of a vector construct comprising a transgene of the invention, and optionally a light chain transgene capable of producing a light chain as defined herein,
(ii) implanting the fertilized ovum into the uterus or the oviduct of a non-human pseudopregnant female animal,
(iii) testing the offspring for the presence of the transgene(s), and
(iv) mating two heterozygous offspring to produce homozygous transgenic strain of the non-human animal.

An alternative method for producing a non-human transgenic animal of the invention comprises the use of a transgenic animal which is already capable of producing human antibodies, such as a HuMab-Mouse™ or a Xenomouse™. as a starting point for further genetic modification. This may be a more convenient method for producing the non-human transgenic animal of the invention, since instead of having to introduce an entire transgene comprising all coding regions for a human antibody, it may, in some embodiment, be carried out by a mere replacement of the sequences encoding the C☐ region(s) in said animals by equivalent C☐ sequences encoding $C_H$ regions having the modifications described herein.

Accordingly, in a further main aspect, the invention relates to method for producing a non-human transgenic animal according to the invention, said method comprising
(i) introducing into the embryonic stem cells of a non-human transgenic animal, which transgenic animal comprises pre-existing transgenic sequences allowing the animal to producing human antibodies, a transgene comprising a sequence which encodes a $C_H$ region or fragment thereof comprising the modifications as defined herein, and, optionally, a transgene comprising a sequence which encodes a $C_L$ region or fragment thereof comprising the modification as defined herein above,
said transgene(s) being designed to, upon genomic integration and replacement of the corresponding human $C_H$ region or fragment thereof, and, optionally, corresponding human $C_L$ region or fragment thereof, of the transgenic animal genome become(s) operably linked to the remaining pre-existing transgenic sequences thus allowing the animal to produce monovalent antibodies as defined herein,
(ii) selecting embryonic stem cells expressing the transgene(s) introduced in step (i),
(iii) injecting the transformed embryonic stem cells into the inner mass of a blastocyst,
(iv) implanting the blastocysts into the uterus or oviduct of a non-human pseudopregnant female animal,
(v) testing the offspring for the presence of the transgene(s), and
(vi) mating two heterozygous offspring to produce homozygous transgenic strain of the non-human animal.

In a further main aspect, the invention relates to method for producing a non-human transgenic animal according to the invention, said method comprising
(i) injecting into the pronucleus of a fertilized ovum of a non-human transgenic animal, which transgenic animal comprises pre-existing transgenic sequences allowing the animal to producing human antibodies, a transgene comprising a sequence which encodes a $C_H$ region or fragment thereof comprising the modifications as defined herein, and, optionally, a transgene comprising a sequence which encodes a $C_L$ region or fragment thereof comprising the modification as defined herein above,
said transgene(s) being designed to, upon genomic integration and replacement of the corresponding human $C_H$ region or fragment thereof, and, optionally, corresponding human $C_L$ region or fragment thereof, of the transgenic animal genome become(s) operably linked to the remaining pre-existing transgenic sequences thus allowing the animal to produce monovalent antibodies as defined herein,
(ii) implanting the fertilized ovum into the uterus or oviduct of a non-human pseudopregnant female animal,
(iii) testing the offspring for the presence of the transgene(s) introduced in step (i), and
(iv) mating two heterozygous offspring to produce homozygous transgenic strain of the non-human animal.

In one embodiment of the above methods, the non-human transgenic animal provided in step (i) is a transgenic mouse, such as a HuMab-Mouse™, KM-Mouse™, TC-Mouse™ or a Xenomouse™.

In one embodiment, the monovalent antibody produced by the non-human transgenic animal of the invention is monovalent in the presence of physiological concentrations of polyclonal human IgG.

The present invention is further illustrated by the following examples which should not be construed as further limiting.

EXAMPLES

Example 1

Oligonucleotide Primers and PCR Amplification

Figure 1:
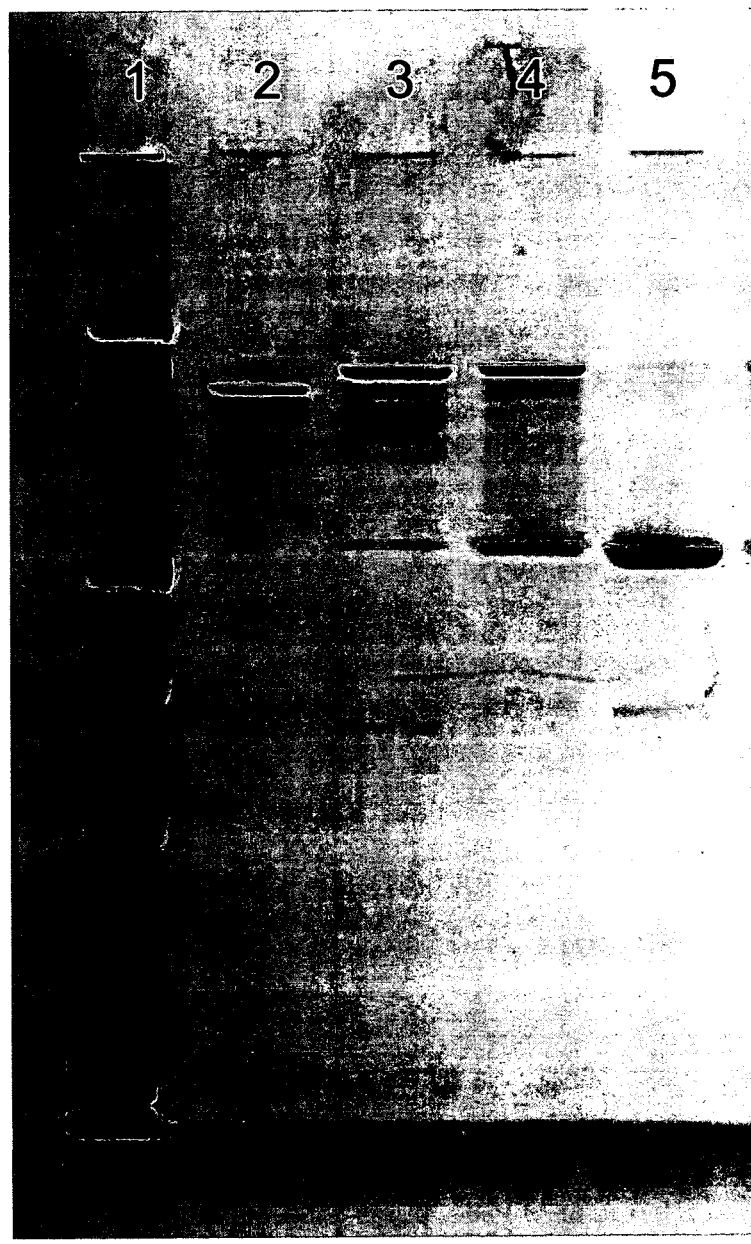
FIG. 1: The CD20-specific antibodies 7D8-IgG1, 7D8-IgG4 and 7D8-HG were evaluated on non-reducing SDS-PAGE.

Oligonucleotide primers were synthesized and quantified by Isogen Bioscience (Maarssen, The Netherlands). Primers were dissolved in $H_2O$ to 100 pmol/μl and stored at −20° C. A summary of all PCR and sequencing primers is tabulated (FIG. 1). For PCR, PfuTurbo® Hotstart DNA polymerase (Stratagene, Amsterdam, The Netherlands) was used according to the manufacturer's instructions. Each reaction mix contained 200 μM mixed dNTPs (Roche Diagnostics, Almere, The Netherlands), 6.7 pmol of both the forward and reverse primer, 100 ng of genomic DNA or 1 ng of plasmid DNA and 1 unit of PfuTurbo® Hotstart DNA polymerase in PCR reaction buffer (supplied with polymerase) in a total volume of 20 μl. PCR reactions were carried out with a TGradient Thermocycler 96 (Whatman Biometra, Goettingen, Germany) using a 32-cycle program: denaturing at 95° C. for 2 min; 30 cycles of 95° C. for 30 sec, a 60-70° C. gradient (or another specific annealing temperature) for 30 sec, and 72° C. for 3 min; final extension at 72° C. for 10 min. If appropriate, the PCR mixtures were stored at 4° C. until further analysis or processing.

Example 2

Agarose Gel Electrophoresis

Agarose gel electrophoresis was performed according to Sambrook (Sambrook J. and Russel, D. V. Molecular Cloning: A Laboratory Manual, 2nd Ed., Cold Spring Harbor, 2000) using gels of 50 ml, in 1× Tris Acetate EDTA buffer. DNA was visualized by the inclusion of ethidium bromide in the gel and observation under UV light. Gel images were recorded by a CCD camera and an image analysis system (GeneGnome; Syngene, via Westburg B. V., Leusden, The Netherlands).

Example 3

Analysis and Purification of PCR Products and Enzymatic Digestion Products

Purification of desired PCR fragments was carried out using a MinElute PCR Purification Kit (Qiagen, via Westburg, Leusden, The Netherlands; product#28006), according to the manufacturer's instructions. Isolated DNA was quantified by UV spectroscopy and the quality was assessed by agarose gel electrophoresis.

Alternatively, PCR or digestion products were separated by agarose gel electrophoresis (for instance when multiple fragments were present) using a 1% Tris Acetate EDTA agarose gel. The desired fragment was excised from the gel and recovered using the QIAEX II Gel Extraction Kit (Qiagen; product#20051), according to the manufacturer's instructions.

Example 4

Quantification of DNA by UV Spectroscopy

Optical density of nucleic acids was determined using a NanoDrop ND-1000 Spectrophotometer (Isogen Life Science, Maarssen, The Netherlands) according to the manufacturer's instructions. The DNA concentration was measured by analysis of the optical density (OD) at 260 nm (one $OD_{260\ nm}$ unit=50 μg/ml). For all samples, the buffer in which the nucleic acids were dissolved was used as a reference.

Example 5

Restriction Enzyme Digestions

Restriction enzymes and supplements were obtained from New England Biolabs (Beverly, Mass., USA) or Fermetas (Vilnius, Lithuania) and used according to the manufacturer's instructions.

DNA (100 ng) was digested with 5 units of enzyme(s) in the appropriate buffer in a final volume of 10 μl (reaction volumes were scaled up as appropriate). Digestions were incubated at the recommended temperature for a minimum of 60 min. For fragments requiring double digestions with restriction enzymes which involve incompatible buffers or temperature requirements, digestions were performed sequentially. If necessary digestion products were purified by agarose gel electrophoresis and gel extraction.

Example 6

Ligation of DNA Fragments

Ligations of DNA fragments were performed with the Quick Ligation Kit (New England Biolabs) according to the manufacturer's instructions. For each ligation, vector DNA was mixed with approximately three-fold molar excess of insert DNA.

Example 7

Transformation of E. coli

Plasmid DNA (1-5 μl of DNA solution, typically 2 μl of DNA ligation mix) was transformed into One Shot DH5α-T1$^R$ or MACH-1 T1$^R$ competent E. coli cells (Invitrogen, Breda, The Netherlands; product#12297-016) using the heat-shock method, according to the manufacturer's instructions. Next, cells were plated on Luria-Bertani (LB) agar plates containing 50 μg/ml ampicillin. Plates were incubated for 16-18 hours at 37° C. until bacterial colonies became evident.

Example 8

Screening of Bacterial Colonies by PCR

Bacterial colonies were screened for the presence of vectors containing the desired sequences via colony PCR using the HotStarTaq Master Mix Kit (Qiagen; product#203445) and the appropriate forward and reverse primers. Selected colonies were lightly touched with a 20 μl pipette tip and touched briefly in 2 ml LB for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Example 9

Plasmid DNA Isolation From E. coli Culture

Plasmid DNA was isolated from E. coli cultures using the following kits from Qiagen (via Westburg, Leusden, The Netherlands), according to the manufacturer's instructions. For bulk plasmid preparation (50-150 ml culture), either a HiSpeed Plasmid Maxi Kit (product#12663) or a HiSpeed Plasmid Midi Kit (product#12643) was used. For small scale plasmid preparation (±2 ml culture) a Qiaprep Spin Miniprep Kit (product#27106) was used and DNA was eluted in 50 μl elution buffer (supplied with kit).

Example 10

Site-Directed Mutagenesis

Site-directed mutagenesis was performed using the QuickChange II XL Site-Directed Mutagenesis Kit (Stratagene, Amsterdam, The Netherlands) according to the manufacturer's instructions. This method included the introduction of a silent extra XmaI site to screen for successful mutagenesis. Briefly, 5 µl 10× reaction buffer, 1 µl oligonucleotide IgG4S228Pf (P16) (100 µmol/µl), 1 µl oligonucleotide IgG4S228Pr (P17) (100 µmol/µl), 1 µl dNTP mix, 3 µl Quicksolution, 1 µl plasmid pTomG4Tom7D8 (see example 16) (50 ng/µl) and 1 µl PfuUltra HF DNA polymerase were mixed in a total volume of 50 µl and amplified with a TGradient Thermocycler 96 (Whatman Biometra, Goettingen, Germany; product#050-801) using an 18-cycle program: denaturing at 95° C. for 1 min; 18 cycles of 95° C. for 50 sec, 60° C. for 50 sec, and 68° C. for 10 min. PCR mixtures were stored at 4° C. until further processing. Next, PCR mixtures were incubated with 1 µl DpnI for 60 min at 37° C. to digest the pTomG47D8 vector and stored at 4° C. until further processing. The reaction mixture was precipitated with 5 µl sM NaAc and 125 µl Ethanol, incubated for 20 minutes at −20° C. and spundown for 20 minutes at 4° C. at 14000×g. The DNA pellet was washed with 70% ethanol, dried and dissolved in 4 µl water. The total 4 µl reaction volume was transformed in One Shot Top 10 competent $E.\ coli$ cells (Invitrogen, Breda, The Netherlands) according to the manufacturer's instructions (Invitrogen). Next, cells were plated on Luria-Bertani (LB) agar plates containing 50 µg/ml ampicillin. Plates were incubated for 16-18 hours at 37° C. until bacterial colonies became evident.

Example 11

DNA Sequencing

DNA sequencing was performed using standard techniques.

Example 12

Transient Expression in HEK-293F Cells

Freestyle™ 293-F (a HEK-293 subclone adapted to suspension growth and chemically defined Freestyle medium, e.g. HEK-293F) cells were obtained from Invitrogen and transfected according to the manufacturer's protocol using 293fectin (Invitrogen).

Example 13

Construction of pConG1fA77

A Vector for the Production of the Heavy Chain of A77-IgG1

The $V_H$ coding region of the mouse anti-FcαRI antibody A77 was amplified from a scFv phage vector, containing the VH and VL coding regions of this antibody, by a double overlap extension PCR. This was used to incorporate a mammalian signal peptide, an ideal Kozak sequence and suitable restriction sites for cloning in pConG1f. The first PCR was done using primers A77VHfor1 and A77VHrev with the scFv phage vector as template. Part of this first PCR was used in a second PCR using primers A77VHfor2 and A77VHrev. The VH fragment was gel purified and cloned into pConG1f0.4. For this the pConG1f0.4 vector and the VH fragment were digested with HindIII and ApaI and purified. The $V_H$ fragment and the pConG1f0.4HindIII-ApaI digested vector were ligated and transformed into competent DH5α-T1$^R$ cells. A clone was selected containing the correct insert size and the sequence was confirmed and was named pConG1fA77.

Example 14

Construction of pConKA77

A Vector for the Production of the Light Chain of A77 Antibodies

The $V_L$ coding region of the mouse anti-FcαRI antibody A77 was amplified from a scFv phage vector, containing the VH and VL of this antibody, by a double overlap extension PCR. This was used to incorporate a mammalian signal peptide, an ideal Kozak sequence and suitable restriction sites for cloning in pConKappa0.4. The first PCR was done using primers A77VLfor1 and A77VLrev with the scFv phage vector as template. Part of this first PCR was used in a second PCR using primers A77VLfor2 and A77VLrev. The PCR product and the pConKappa0.4 vector were digested with HindIII and Pfl23II and purified. The $V_L$ fragment and the pConKappa0.4HindIII-Pfl23II digested vector were ligated and transformed into competent DH5α T1$^R$ $E.\ coli$.

A clone was selected containing the correct insert size and the sequence was confirmed. This plasmid was named pConKA77.

Example 15

Construction of pTomG4A77

A Vector for the Production of the Heavy Chain of A77-IgG4

To construct a vector for expression of A77-IgG4, the VH region of A77 was cloned in pTomG4.

For this, pTomG4 and pConG1fA77 were digested with HindIII and ApaI and the relevant fragments were isolated.

The A77 $V_H$ fragment and the pTomG4HindIII-ApaI digested vector were ligated and transformed into competent DH5α-T1$^R$ cells.

A clone was selected containing the correct insert size. This plasmid was named pTomG4A77.

Example 16

Construction of pTomG4A77HG

A Vector for the Production of the Heavy Chain of A77-HG

To make a construct for expression of A77-HG, the VH region of A77 was cloned in pTomG47D8HG, replacing the VH 7D8 region.

For this pTomG47D8HG and pConG1fA77 were digested with HindIII and ApaI and the relevant fragments were isolated.

The A77 $V_H$ fragment and the pTomG47D8HGHindIII-ApaI digested vector fragment were ligated and transformed into competent DH5α-T1$^R$ cells.

A clone was selected containing the correct insert size. This plasmid was named pTomG4A77HG.

Example 17

Construction of pEE6.4A77Fab

A Vector for the Production of the Heavy Chain of A77-Fab

To make a construct for expression of A77-Fab, the VH region of A77 was cloned in pEE6.42F8Fab, replacing the VH 2F8 region.

For this pEE6.42F8Fab and pConG1fA77 were digested with HindIII and ApaI and the relevant fragments were isolated.

The A77 $V_H$ fragment and the pEE6.42F8Fab HindIII-ApaI digested vector fragment were ligated and transformed into competent DH5α-T1$^R$ cells.

A clone was selected containing the correct insert. This plasmid was named pEE6.4A77Fab.

Example 18

Cloning of the Variable Regions of a Human Anti-cMet Antibody

Total RNA was prepared from 1×10$^6$ mouse hybridoma cells with the RNeasy kit (Qiagen, Westburg, Leusden, Netherlands) according to the manufacturer's protocol.

5'-RACE-Complementary DNA (cDNA) of RNA was prepared from 60 ng total RNA, using the SMART RACE cDNA Amplification kit (BD Biosciences Clontech, Mountain View, Calif., USA), following the manufacturer's protocol.

The VL and VH regions of the cMet antibody were amplified by PCR. For this PfuTurbo® Hotstart DNA polymerase (Stratagene) was used according to the manufacturer's instructions. Each reaction mix contained 5 µl 10× BD Advantage 2 PCR buffer (Clontech), 200 µM mixed dNTPs (Roche Diagnostics), 12 µmol of the reverse primer (RACEG1A1 for the VH region and RACEKA1 for the VL region), 7.2 pmol UPM-Mix (UPM-Mix: 2 µM ShortUPMH3 and 0.4 µM LongUPMH3 oligonucleotide), 1 µl of the 5'RACE cDNA template as described above, and 1 µl 50×BD Advantage 2 polymerase mix (Clontech) in a total volume of 50 µl.

PCR reactions were carried out with a TGradient Thermocycler 96 (Whatman Biometra) using a 35-cycle program: denaturing at 95° C. for 1 min; 35 cycles of 95° C. for 30 sec, 68° C. for 60 sec.

The reaction products were separated by agarose gel electrophoresis on a 1% TAE agarose gel and stained with ethidium bromide. Bands of the correct size were cut from the gels and the DNA was isolated from the agarose using the Qiagen Minelute Reaction Cleanup kit (Qiagen).

Gel isolated PCR fragments were cloned into the pCR4Blunt-TOPO vector (Invitrogen) using the Zero Blunt® TOPO® PCRCloning Kit for Sequencing (Invitrogen), following the manufacturer's protocol. 5 µl of the ligation mixture was transformed into OneShot DH5αT1R competent E. coli (Invitrogen) and plated on LB/Ampicillin plates.

From six, insert containing, clones, the $V_L$ sequences were determined and from five, insert containing, clones, the $V_H$ sequences were determined.

Example 19

Construction of pConG1fcMet

A Vector for the Production of the Heavy Chain of cMet-IgG1

The $V_H$ coding region of the human anti-cMet antibody was cut from a plasmid containing this region using HindIII and ApaI. The VH fragment was gel purified and cloned into pConG1f0.4. For this pConG1f0.4 vector were digested with HindIII and ApaI and purified. The $V_H$ fragment and the pConG1f0.4HindIII-ApaI digested vector were ligated and transformed into competent DH5α-T1R cells.

A clone was selected containing the correct insert size was isolated and was named pConG1fcMet.

Example 20

Construction of pConKcMet

A Vector for the Production of the Light Chain of cMet Antibodies

The $V_L$ coding region of the human anti-cMet antibody was amplified from a plasmid containing this region using the primers shortUPMH3 and RACEVLBsiWI, introducing suitable restriction sites for cloning into pConK0.4.

The PCR product and the pConKappa0.4 vector were digested with HindIII and Pfl23II and purified. The $V_L$ fragment and the pConKappa0.4HindIII-Pfl23II digested vector were ligated and transformed into competent DH5α T1$^R$ E. coli.

A clone was selected containing the correct insert size and the sequence was confirmed. This plasmid was named pConKcMet.

Example 21

Construction of pTomG4cMet

A Vector for the Production of the Heavy Chain of cMet-IgG4

To construct a vector for expression of cMet-IgG4, the VH region of cMet was cloned in pTomG4.

For this, pTomG42F8 and pConG1fcMet were digested with HindIII and ApaI and the relevant fragments were isolated.

The cMet $V_H$ fragment and the pTomG42F8HindIII-ApaI digested vector were ligated and transformed into competent DH5α-T1$^R$ cells.

A clone was selected containing the correct insert size. This plasmid was named pTomG4cMet.

Example 22

Construction of pTomG4cMetHG

A Vector for the Production of the Heavy Chain of cMet-HG

To make a construct for expression of cMet-HG, the VH region of cMet was cloned in pTomG42F8HG, replacing the VH 2F8 region.

For this pTomG42F8HG and pConG1fcMet were digested with HindIII and ApaI and the relevant fragments were isolated.

The cMet $V_H$ fragment and the pTomG42F8HGHindIII-ApaI digested vector fragment were ligated and transformed into competent DH5α-T1$^R$ cells.

A clone was selected containing the correct insert size. This plasmid was named pTomG4cMetHG.

Example 23

Construction of pEE6.4cMetFab

A Vector for the Production of the Heavy Chain of cMet-Fab

To make a construct for expression of cMet-Fab, the VH region of cMet was cloned in pEE6.42F8Fab, replacing the VH 2F8 region.

For this pEE6.42F8Fab and pConG1fcMet were digested with HindIII and ApaI and the relevant fragments were isolated.

The cMet $V_H$ fragment and the pEE6.42F8Fab HindIII-ApaI digested vector fragment were ligated and transformed into competent DH5α-T1$^R$ cells.

A clone was selected containing the correct insert. This plasmid was named pEE6.4cMetFab.

Example 24

Construction of pConG1f2F8

A Vector for the Production of the Heavy Chain of 2F8-IgG1

The $V_H$ coding region of 2F8 (WO 2002/100348) was amplified by PCR from pIESRα2F8 (Medarex) using the primers 2f8HCexfor and 2f8HCexrev and subcloned in PCR-scriptCam (Stratagene). The VH fragment was subsequently cloned in pCONg1f0.4.

For this pConG1f0.4 and the pCRScriptCAMVH2F8 vectors were digested with HindIII and ApaI and the relevant fragments were purified.

The $V_H$ fragment and the pConG1f0.4HindIII-ApaI digested vector were ligated and transformed into competent DH5α-T1$^R$ cells. A clone was selected containing the correct insert size, the sequence was confirmed and the vector was named pConG1f2F8.

Example 25

Construction of pConK2F8

A Vector for the Production of the Light Chain of 2F8 Antibodies pIESRα2F8 was digested with HindIII and BsiWI and the $V_L$ coding region of 2F8 (anti-EGFr) was isolated from gel. The pConKappa0.4 vector was digested with HindIII and BsiWI and purified. The $V_L$ fragment and the pConKappa0.4HindIII-BsiWI digested vector were ligated and transformed into competent DH5α T1$^R$ E. coli.

A clone was selected containing the correct insert size and the sequence was confirmed. This plasmid was named pConK2F8.

Example 26

Construction of pTomG42F8

A Vector for the Production of the Heavy Chain of 2F8-IgG4

To construct a vector for expression of 2F8-IgG4, the VH region of 2F8 was cloned in pTomG4.

For this, pTomG4 and pConG1f2F8 were digested with HindIII and ApaI and the relevant fragments were isolated.

The 2F8 $V_H$ fragment and the pTomG4HindIII-ApaI digested vector were ligated and transformed into competent DH5α-T1$^R$ cells.

A clone was selected containing the correct insert size. This plasmid was named pTomG42F8.

Example 27

Construction of pTomG42F8HG

A Vector for the Production of the Heavy Chain of 2F8-HG

To make a construct for expression of 2F8-HG, the VH region of 2F8 was cloned in pTomG47D8HG, replacing the VH 7D8 region.

For this pTomG47D8HG and pConG1f2F8 were digested with HindIII and ApaI and the relevant fragments were isolated.

The 2F8 $V_H$ fragment and the pTomG47D8HGHindIII-ApaI digested vector fragment were ligated and transformed into competent DH5α-T1$^R$ cells.

A clone was selected containing the correct insert size. This plasmid was named pTomG42F8HG.

Example 28

Construction of pEE6.42F8Fab

A Vector for the Production of the Heavy Chain of 2F8-Fab

The Fab coding region was amplified from vector pConG1f2F8 by PCR with primers pConG1seq1 and 2F8fabrev2, introducing a suitable cloning restriction site and a C-terminal his tag coding sequence. The PCR fragment was purified and cloned in PEE6.4.

For this pEE6.4 and the PCR fragment were digested with HindIII and EcoRI and the relevant fragments were isolated.

The 2F8 Fab fragment and the pEE6.4HindIII-EcoRI digested vector fragment were ligated and transformed into competent DH5α-T1$^R$ cells.

A clone was selected containing the correct insert and the sequence was confirmed by DNA sequencing. This plasmid was named pEE6.42F8Fab.

Example 29

Construction of pConG1f7D8

A Vector for Production of the Heavy Chain of 7D8-IgG1

The $V_H$ coding region of CD20 specific HuMab-7D8 (WO 04/035607) was amplified by PCR from a pGemT (Promega, Madison, USA) vector containing this region using the primers 7D8VHexfor (P8) and 2F8HCexrev (P13) (FIG. 14), introducing suitable restriction sites for cloning into pConG1f0.4 (Lonza Biologics, Slough, UK), a mammalian expression vector containing the genomic constant region (allotype f) of human IgG1, and an ideal Kozak sequence (GCCGCCACC, (Kozak M et al., Gene 234(2), 187-208 (1999)). The PCR fragment was cloned in pPCR-Script CAM (Stratagene, Amsterdam, The Netherlands) using a PCR-Script® Cam Cloning Kit (Stratagene), according to the manufacture's instructions. Several clones were sequenced and a clone containing the predicted sequence was chosen for further use.

The V$_H$ fragment was gel purified and cloned into pConG1f0.4. For this the V$_H$ fragment was isolated from the pPCR-Script CAM vector after digestion with HindIII and ApaI and gel purification.

The pConG1f0.4 vector was digested with HindIII and ApaI and the vector fragment was isolated from gel, followed by dephosphorylation with Shrimp Alkaline Phosphatase (New England Biolabs) The V$_H$ fragment and the pConG1f0.4HindIII-ApaI dephosphorylated fragment were ligated and transformed into competent DH5α-T1$^R$ cells (Invitrogen). Eight colonies were checked by colony PCR (using primers pConG1seq1 (P10) and HCseq5 (P11) (FIG. 14) and all colonies were found to contain the correct insert size.

A clone was chosen for further study and named pConG1f7D8.

Example 30

Construction of pConK7D8

A Vector for Production of the Light Chain of 7D8-IgG1, 7D8-IgG4 and 7D8-HG

The V$_L$ coding region of CD20 specific HuMab-7D8 (WO 04/035607) was amplified from a plasmid containing this region using the primers 7D8VLexfor (P7) and 7D8VLexrev (P6) (FIG. 14), introducing suitable restriction sites for cloning into pConKappa0.4 (Lonza Biologics), a mammalian expression vector containing the constant kappa light chain region (allotype km3) of human IgG, and an ideal Kozak sequence.

The PCR product and the pConKappa0.4 vector were digested with HindIII and BsiWI. The vector and V$_L$ fragment were purified and the vector was dephosphorylated with Shrimp Alkaline Phosphatase. The V$_L$ fragment and the pConKappa0.4HindIII-Bs/WI digested vector were ligated and transformed into competent DH5α T1$^R$ E. coli. Ten colonies were checked by colony PCR (using primers pConKseq1 (P9) and LCseq3 (P5) (FIG. 14) and 9 colonies were found to contain the correct insert size.

From 4 clones plasmid DNA was isolated and the V$_L$ region was sequenced. 3 clones contained the predicted sequence and one clone was chosen for further use and named pConK7D8.

Example 31

Construction of pTomG4

A Vector for the Expression of Variable Heavy Chain Regions of Human IgG with the Constant Region of Human IgG4

Genomic DNA was isolated from a blood sample of a volunteer and used as a template in a PCR with primers IgG4gene2f (P15) and IgG4gene2r (P14) (FIG. 14), amplifying the complete genomic constant region of the heavy chain of IgG4 and introducing suitable restriction sites for cloning into the mammalian expression vector pEE6.4 (Lonza Biologics). The PCR fragment was purified and cloned into pEE6.4. For this the PCR product was digested with HindIII and EcoRI, followed by heat inactivation of the restriction enzymes. The pEE6.4 vector was digested HindIII and EcoRI, followed by heat inactivation of the restriction enzymes and dephosphorylation of the vector fragment with shrimp alkaline phosphatase, followed by heat inactivation of the phosphatase. The IgG4 fragment and the pEE6.4HindIII/EcoRI dephosphorylated vector were ligated and transformed into competent MACH1-T1$^R$ cells (Invitrogen). Three clones were grown in LB and plasmid DNA was isolated from a small culture (1.5 ml). Restriction digestion revealed a pattern consistent with the cloning of the IgG4 fragment in the pEE6.4 vector. Plasmid DNA from two clones was transformed in DH5α-T1$^R$ E. coli and plasmid DNA was isolated and the constructs were checked by sequence analysis of the insert and one clone was found to be identical to a genomic IgG4 clone from the Genbank database, apart from some minor differences in introns. SEQ ID No: 13 shows the sequence of the IgG4 region in pTomG4. These differences are presumably either polymorphisms or sequence faults in the Genbank sequence. The plasmid was named pTomG4.

Example 32

Construction of pTomG47D8

A Vector for the Production of the Heavy Chain of 7D8-IgG4

Plasmid DNA from pConG1f7D8 was digested with HindIII and ApaI and the V$_H$ fragment was gel purified. The pTomG4 vector was digested with HindIII and ApaI and the vector fragment was isolated from gel. The V$_H$ fragment and the pTomG4HindIII-ApaI fragment were ligated and transformed into competent DH5α-T1$^R$ cells. Four colonies were checked by colony PCR (using primers pConKseq1 (P9) and HCseq11 (P12)) and two were found to contain the correct insert size and the presence of the pTomG4 backbone was confirmed by a digestion with MspI on the colony PCR fragment. One of the clones was chosen for further use. This plasmid was named pTomG47D8.

Example 33

Construction of pTomG47D8HG

A Vector for the Expression of the Heavy Chain of 7D8-Hg

Site directed mutagenesis was used to destroy the splice donor site of the hinge exon of IgG4 in the pTomG47D8 plasmid. A site-directed mutagenesis reaction was done according to the QuickChange XL site-directed mutagenesis method using primers IgG4S228Pf (P16) and IgG4S228Pr (P17). 24 colonies were screened by colony PCR and XmaI digestion (an extra XmaI site was introduced during mutagenesis) and all colonies appeared to contain the correct nucleotide changes. Two positive colonies were grown overnight, plasmid DNA was isolated and sequenced to confirm that the correct mutation was introduced. Both did contain the correct sequence and one was chosen for further propagation and named pTomG47D8HG. To exclude the introduction of additional mutations during the mutagenesis process, the whole IgG4 coding region of pTomG47D8HG was resequenced and no additional mutations were found. The final vector was named pTomG47D8HG.

Example 34

Cloning of the Variable Regions of the Mouse Anti-Betv1 Antibody

Total RNA was prepared from 0.3×10$^5$ mouse hybridoma cells (Clone 2H8 from reference (Akkerdaas J H et al., Allergy 50(3), 215-20 (1995)) with the RNeasy kit (Qiagen, Westburg, Leusden, Netherlands) according to the manufacturer's protocol.

5'-RACE-Complementary DNA (cDNA) of RNA was prepared from 112 ng total RNA, using the SMART RACE cDNA Amplification kit (BD Biosciences Clontech, Mountain View, Calif., USA), following the manufacturer's protocol.

The $V_L$ and $V_H$ regions of the Betv1 antibody were amplified by PCR. For this PfuTurbo® Hotstart DNA polymerase (Stratagene) was used according to the manufacturer's instructions. Each reaction mix contained 200 μM mixed dNTPs (Roche Diagnostics), 12 μmol of the reverse primer (RACEG1 mm1 (P19) for the $V_H$ region and RACEKmm1 (P18) for the $V_L$ region), 7.2 μmol UPM-Mix (UPM-Mix: 2 μM ShortUPMH3 (P20) and 0.4 μM LongUPMH3 (P21) oligonucleotide (FIG. 14)), 0.6 μl of the 5'RACE cDNA template as described above, and 1.5 unit of PfuTurbo® Hotstart DNA polymerase in PCR reaction buffer (supplied with polymerase) in a total volume of 30 μl.

PCR reactions were carried out with a TGradient Thermocycler 96 (Whatman Biometra) using a 35-cycle program: denaturing at 95° C. for 2 min; 35 cycles of 95° C. for 30 sec, a 55° C. for 30 sec, and 72° C. for 1.5 min; final extension at 72° C. for 10 min.

The reaction products were separated by agarose gel electrophoresis on a 1% TAE agarose gel and stained with ethidium bromide. Bands of the correct size were cut from the gels and the DNA was isolated from the agarose using the QiaexII gel extraction kit (Qiagen).

Gel isolated PCR fragments were A tailed by a 10 min 72° C. incubation with 200 μM dATP and 2.5 units Amplitaq (Perkin Elmer) and purified using minielute columns (Qiagen). A-tailed PCR fragments were cloned into the pGEMTeasy vector (Promega) using the pGEMT easy vector system II kit (Promega), following the manufacturer's protocol. 2 μl of the ligation mixture was transformed into OneShot DH5αT1R competent *E. coli* (Invitrogen) and plated on LB/Amp/IPTG/Xgal plates.

Four insert containing, white colonies each for the $V_H$ and $V_L$ sequences were picked and the inserts were sequenced. The deduced amino acid sequences of the $V_H$ and $V_L$ of Betv1 are shown as SEQ ID No: 8 and SEQ ID No:12, respectively.

Example 35

Construction of pConG1fBetV1

A Vector for the Production of the Heavy Chain of Betv1-IgG1

The $V_H$ coding region of mouse anti-BetV1 antibody was amplified by PCR from a plasmid containing this region (example 18) using the primers VHexbety1for (P4) and VHexbety1rev (P3), introducing suitable restriction sites for cloning into pConG1f0.4 and an ideal Kozak sequence.

The $V_H$ fragment was gel purified and cloned into pConG1f0.4. For this the PCR product and the pConKappa0.4 vector were digested with HindIII and ApaI and purified.

The $V_H$ fragment and the pConG1f0.4HindIII-ApaI digested vector were ligated and transformed into competent DH5α-T1$^R$ cells.

A clone was selected containing the correct insert size and the correct sequence was confirmed. This plasmid was named pConG1fBetv1.

Example 36

Construction of pConKBetv1

A Vector for the Production of the Light Chain of Betv1

The $V_L$ coding region mouse anti-BetV1 antibody was amplified from a plasmid containing this region (example 18) using the primers VLexbetv1for (P2) and VLexbetv1rev (P1), introducing suitable restriction sites for cloning into pConK0.4 and an ideal Kozak sequence.

The PCR product and the pConKappa0.4 vector were digested with HindIII and Bs/WI and purified. The $V_L$ fragment and the pConKappa0.4HindIII-Bs/WI digested vector were ligated and transformed into competent DH5α T1$^R$ *E. coli*.

A clone was selected containing the correct insert size and the sequence was confirmed. This plasmid was named pConKBetv1.

Example 37

Construction of pTomG4Betv1

A Vector for the Production of the Heavy Chain of Betv1-IgG4

To construct a vector for expression of Betv1-IgG4, the $V_H$ region of BetV1 was cloned in pTomG4.

For this, pTomG4 and pConG1fBetv1 were digested with HindIII and ApaI and the relevant fragments were isolated.

The Betv1 $V_H$ fragment and the pTomG4HindIII-ApaI digested vector were ligated and transformed into competent DH5α-T1$^R$ cells.

A clone was selected containing the correct insert size and the sequence was confirmed. This plasmid was named pTomG4Betv1.

Example 38

Construction of pTomG4Betv1 HG

A Vector for the Production of the Heavy Chain of Betv1-HG

To make a construct for expression of Betv1-HG, the $V_H$ region of Betv1 was cloned in pTomG47D8HG, replacing the $V_H$ 7D8 region.

For this pTomG47D8HG and pConG1fBetv1 were digested with HindIII and ApaI and the relevant fragments were isolated.

The Betv1 $V_H$ fragment and the pTomG47D8HG HindIII-ApaI digested vector fragment were ligated and transformed into competent DH5α-T1$^R$ cells.

A clone was selected containing the correct insert size and the sequence was confirmed. This plasmid was named pTomG4Betv1HG.

Example 39

Production of 7D8-IgG1, 7D8-IgG4, 7D8-HG, Betv1-IgG1, Betv1-IgG4, Betv1-HG, 2F8-IgG1, 2F8-IgG4, 2F8-HG, 2F8-Fab, A77-IgG1, A77-IgG4, A77-HG, A77-Fab, cMet-IgG1, cMet-IgG4, cMet-HG, and cMet-Fab by Transient Expression in Hek-293F Cells Antibodies were produced of all constructs by cotransfecting the relevant heavy and light chain vectors in HEK-293F cells using 293fectin according to the manufacturer's instructions. For 7D8-IgG1, pConG1f7D8 and pConK7D8 were coexpressed. For 7D8-IgG4, pTomG47D8 and pConK7D8 were coexpressed. For 7D8-HG, pTomG47D8HG and pConK7D8 were coexpressed. For Betv1-IgG1, pConG1Betv1 and pConKBetv1 were coexpressed. For Betv1-IgG4, pTomG4Betv1 and pConKBetv1 were coexpressed. For Betv1-HG, pTomG4Betv1HG and pConKBetv1 were coexpressed.

For 2F8-IgG1, pConG1f2F8 and pConK2F8 were coexpressed. For 2F8-IgG4, pTomG42F8 and pConK2F8 were coexpressed. For 2F8-HG, pTomG42F8HG and pConK2F8 were coexpressed. For 2F8-Fab, pEE6.42F8-Fab and pConK2F8 were coexpressed.

For cMet-IgG1, pConG1fcMet and pConKcMet were coexpressed. For cMet-IgG4, pTomG4cMet and pConKcMet were coexpressed. For cMet-HG, pTomG4cMetHG and pConKcMet were coexpressed. For cMet-Fab, pEE6.4cMet-Fab and pConKcMet were coexpressed.

For A77-IgG1, pConG1fA77 and pConKA77 were coexpressed. For A77-IgG4, pTomG4A77 and pConKA77 were coexpressed. For A77-HG, pTomG4A77HG and pConKA77 were coexpressed. For A77-Fab, pEE6.4A77-Fab and pConKA77 were coexpressed.

Example 40

Purification of IgG1, IgG4 and IgG4-Hingeless Antibodies

All IgG1, IgG4 and hingeless antibodies were purified. First the supernatants were filtered over 0.20 μM dead-end filter. Then, the supernatant was loaded on a 5 ml Protein A column (rProtein A FF, Amersham Bioscience) and eluted with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis samples were sterile filtered over 0.20 μM dead-end filter.

Antibodies were deglycosylated by overnight incubation at 37° C. with 1 unit PNgase F (Roche)/μg antibody, followed by purification on protein A.

Samples were analyzed for concentration of IgG by nephelometry and absorbance at 280 nm.

Example 41

Purification of Recombinant Fab Antibodies by Metal Affinity Chromatography

Talon beads (Clontech) were used for purification of the A77-Fab, 2F8-Fab and cMet-Fab antibodies.

Before use, the beads were equilibrated with 1× equilibration/wash buffer pH 7.0 (50 mM sodium phosphate and 300 mM NaCl) followed by incubation with the culture supernatant containing the Fab antibody. The beads were washed with 1× equilibration/wash buffer to remove aspecific bound proteins and the His-tagged protein was eluted with 1× elution buffer (50 mM sodium phosphate, 300 mM NaCl and 150 mM Imidazole) at pH 5.0. Incubation was done batch wise, whereas washing and elution were done in packed columns using centrifugation (2 minutes at 700 g). The eluted protein was desalted on a PD-10 column by exchanging to PBS. The yield of purified protein was determined by measuring the absorbance at 280 nm using the theoretic absorbance coefficient as calculated from the amino acid sequence. Purified proteins were analyzed by SDS-PAGE, the protein migrated as one band at the expected size.

Example 42

Non-Reduced SDS-PAGE Analysis of 7D8-IgG4 and 7D8-HG Antibodies

After purification, the CD20 specific antibodies 7D8-IgG1 (IgG1 anti-CD20) 7D8-IgG4 (IgG4 anti-CD20) and 7D8-HG (hingeless IgG4 anti-CD20) were analyzed on non-reducing SDS-PAGE.

The Bis-Tris electrophoresis method used is a modification of the Laemmli method (Laemmli U K, Nature 227, 6801 (1970)), where the samples were run at neutral pH. The SDS-PAGE gels were stained with Coomassie and digitally imaged using the GeneGenius (Synoptics, Cambridge, UK).

As can be seen in FIG. 1, 7D8-IgG1 showed 1 major bind representing the full length tetrameric (2 heavy and two light chains) 7D8 IgG1 molecule. 7D8-IgG4 shows to have besides the major band representing the tetrameric IgG4 molecule a substantial amount of half-molecules (i.e. one heavy band one light chain) as has been described in literature (Schuurman J et. al., Mol Immunol 38, 1 (2001); Angal S et al., Mol Immunol 30, 105 (1993); Colcher D et al., Cancer Res 49, 1738 (1989); King D J et al., Biochem J 281 (Pt 2), 317 (1992); Petersen J G et al., J Biol Chem 249, 5633 (1974)). The hingeless IgG4 molecule 7D8-HG is shown to be only half-molecules.

Example 43

Mass Spectrometry of 7D8-HG

For Mass Spectrometry by Nanospray technique the samples were concentrated and buffer was exchanged to 20 mM sodium phosphate, pH 7.2 using Millipore Microcon YM-30 concentrators. Subsequently, approximately 100 μg IgG was digested for 16 hours at 37° C. with 1 U N-glycosidase F (Roche, cat. no. 1365177) to release the N-linked glycans.

Samples were desalted off-line using a C4 micro-trap cartridge and eluted in 30% propanol/5% acetic acid. Molecular weight analysis was performed using nanospray Electrospray-MS using a Q-TOF (Waters, Almere, the Netherlands). The instrument was calibrated using glu-fibrinopeptide. Masslynx 4.0 software was used to deconvolute the multiply-charged data obtained.

A further aliquot of the sample was reduced using dithiothreitol. The products of reduction were desalted off-line using a C4 microtrap and analyzed as described above. MS analysis of 7D8-HG under reducing conditions showed a light chain mass of 23440 dalton which is consistent with the predicted light chain mass of 23440 dalton. No mass of the heavy chain was detected, probably because of precipitation of the heavy chain.

MS analysis under non-reduced conditions showed a predominant mass of 71520 dalton, which correlates well with the predicted mass (71522 dalton) of a half-molecule (combining one heavy and one light chain) missing the hinge. A tiny amount of a product with a mass of 143041 dalton was observed, probably representing a tetrameric molecule with a hingeless heavy chain.

Example 44

Mass Spectrometry Peptide Mapping of 7D8-HG

An aliquot (25 μg) of 7D8-HG was digested with CNBr for 5 hours at room temperature. The CNBr digested sample was freeze-dried and then redissolved in 50 mM ammonium bicarbonate buffer adjusted to pH 8.4 with 10% aq. ammonia and digested with TPCK-treated trypsin for 5 hours at 37° C. The products of digestion were lyophilized and reduction was performed on the digested lyophilized sample using a 20 times molar excess of dithiothreitol (DTT) in Tris-acetate buffer at pH 8.5. The products of the reaction were analyzed by on-line LC/ES-MS using a C18 column. Elution was carried out using aqueous formic acid and an acetonitrile gradient. Detection of masses occurred with a LCT Premier Electrospray mass spectrometer, calibrated over the range of m/z 250 to 3000.

A tryptic peptide with a mass of 2026.2 Da corresponding to the theoretic mass of the hingeless specific peptide 220 VAPEFLGGPSVFLFPPKPK 238 was detected (FIG. 2). The identity of this peptide was confirmed by nanospray MS and MS/MS (FIGS. 3 and 4).

This result shows that the 7D8-HG antibody does not contain a hinge region.

Example 45

Molecular Mass Distribution from Sedimentation Velocity by Analytical Ultracentrifuge (AUC) Experiments of 7D8-HG A 1 mg/ml sample of 7D8-HG in PBS was send to Nanolytics (Dalgow, Germany) for AUC analysis. A dominant population of 7D8-HG sediments with a velocity of 6.7 S (95%) was identified. A distinct aggregate was found at 11.5 S (2%). The rest of the material was found in higher aggregates.

The sedimentation coefficient of the major fraction indicates that 7D8-HG in PBS predominantly occurs as a dimer with a frictional ratio of 1.4.

Apparently 7D8-HG forms a dimer by low affinity non-covalent interactions, presumably in the CH3 region (Saphire, Stanfield et al. 2002 J Mol Biol 319(1): 9-18). This dimerization process can be inhibited by using HG molecules in the presence of an excess of irrelevant antibodies (see example 54)

Example 46

Functional Analysis of 7D8-IgG1, 7D8-IgG4 and 7D8-HG Antibodies

Binding to the CD20 antigen of these CD20 specific antibodies was examined by flow cytometry. NSO/CD20 transfected cells (50,000 cells/50 μl) were washed in FACS buffer (FB: PBS, 0.05% BSA, 0.02% NaN$_3$) and incubated in V-bottom 96-well plates with the test antibodies (50 μl at 4° C. for 30 min). After washing, goat F(ab)$_2$ anti-human IgG-kappa labeled with PE (Southern Biotechnology, cat No: 2062-09, www.southernbiotech.com) was added to the cells. Cells were washed in FB and cells were collected in FACS tubes in a total volume of 150 μl. Samples were measured and analyzed by use of FACScalibur™ (Becton Dickinson, San Diego, Calif., USA).

As can be seen in FIG. 5, all three antibodies were antigen specific and showed good binding to CD20.

In order to determine binding of C1q (the first component of the classical complement cascade) to 7D1-IgG1, 7D8-IgG4 and 7D8-HG an ELISA was performed. In short, microtiter ELISA plates (Greiner, Germany) were coated overnight at RT with the test antibodies serially diluted from 10 μg/ml to 0.06 μg/ml in PBS. Plates were emptied and wells were blocked with 200 μl ELISA-diluent per well (0.1 M NaPO$_4$, 0.1 M NaCl, 0.1% gelatin and 0.05% Tween-20), at RT for 30 minutes. Subsequently, plates were emptied and wells were incubated with 2 μg/ml human C1q (Quidel, lot #900848) in C1q buffer (PBS supplemented with 0.1% w/v gelatine and 0.05% v/v Tween-20, 100 μl/well, 37° C., 1 hour). Plates were washed three times with PBST and wells were incubated with rabbit anti-human C1q (DAKO, A0136), diluted in C1q buffer (100 μl/well, RT, 1 h). After washing the plates (3×) with PBST, wells were incubated with HRP-conjugated swine anti-rabbit IgG-Fc (DAKO, P0300, lot #069) diluted in ELISA diluent (1:2500, 100 μl/well, RT, 1 hour). Thereafter, plates were washed thrice and assays were developed with freshly prepared 1 mg/ml ABTS solution (ABTS: 2,2'-azino-bis[3-ethylbenzthiazoline-6-sulfonic acid]); 2 tablets of 5 mg in 10 ml ABTS buffer, Boehringer Mannheim, Ingelheim, Germany) at RT in the dark for 30 minutes. Absorbance was measured at 405 nm in an ELISA plate reader (Biotek Instruments Inc., Winooski, USA).

As can be seen in FIG. 6, C1q did not bind to both 7D8-IgG4 and 7D8-HG. As a control C1q binding to 7D8-IgG1 was evaluated which showed concentration dependent binding of C1q.

To further investigate the complement properties of the CD20-specific antibodies, the complement-dependent cellular toxicity was examined. After harvesting, Daudi cells (ATCC, www.ATCC.org) were washed trice in PBS and resuspended at 2×10$^6$ cells/ml in RPMI 1640, supplemented with 1% (w/v) bovine serum albumin (BSA; Roche, Basel, Switzerland). Then, cells were put in a 96-well round-bottom plate at 1.0×10$^5$ cells/well in a volume of 50 μl. The same volume of antibody (highest concentration 10 μg/ml, diluted in RPMI 1640 and 1% BSA) was added to the wells and incubated for 15 minutes at room temperature (RT). Then 25 μl normal human serum (NHS) was added and the cells were incubated at 37° C. for 45 minutes. Heat-inactivated serum (serum ΔT) is NHS which has been incubated for 10 minutes on 56° C. After incubation for 45 minutes, cells were resuspended transferred to FACS tubes (Greiner). Then, 10 μl propidium iodide (PI; Sigma-Aldrich Chemie B.V.) was added (10 μg/ml solution) to this suspension. Lysis was detected by flow cytometry (FACScalibur™, Becton Dickinson, San Diego, Calif., USA) by measurement of the number of dead cells (PI-positive cells).

Figure 7A:
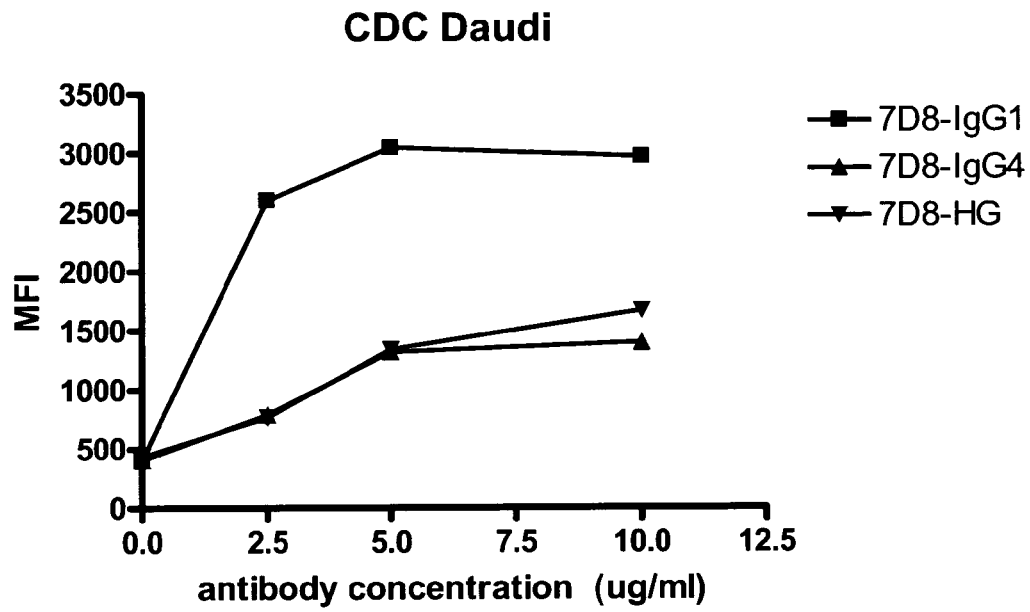

As can be seen in FIG. 7A, 7D8-IgG1 showed good lysis of daudi cells whereas both 7D8-IgG4 and 7D8-HG showed a decreased lysis of Daudi cells.

Figure 7B:
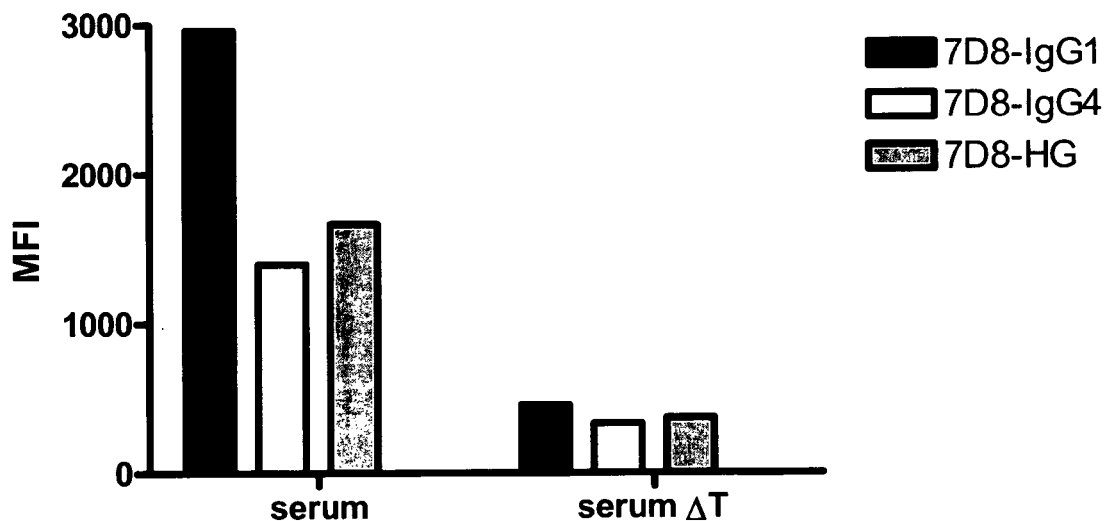

To evaluate the role of serum, heat-inactivated serum (serum ΔT) was added to cells incubated with 10 μg antibody. FIG. 7B showed that the induction of lysis was dependent on complement-active serum, addition of heat-inactivated serum resulted in no lysis.

Example 47

Non-Reduced SDS-Page Analysis of Betv1-HG Antibody

After purification, the Betv1-HG (hingeless IgG4 anti-Bet v1) was analyzed on non-reducing SDS-PAGE. The used Bis-Tris electrophoresis method is a modification of the Laemmli method the samples were run at neutral pH. The SDS-PAGE gels were stained with Coomassie and digitally imaged using the GeneGenius (Synoptics, Cambridge, UK).

As can be seen in FIG. 8, Betv1-HG showed 1 major bind representing a half-molecule (i.e. one heavy and one light chain).

Example 48

Gelfiltration of Betv1-HG Antibody

Betv1-HG was subjected to gelfiltration to investigate whether this mutant would elute as half-molecule or intact dimer. Samples (100 µl) were applied to a Superdex 200 HR 10/30 column (Amersham Biosciences, Uppsala, Sweden), which was connected to a HPLC system (ÄKTA explorer) from Amersham Biosciences, Uppsala, Sweden. The column was first equilibrated in PBS. Fractions of 250 µl were collected, in which Bet v 1 specific IgG was measured using the antigen binding assay. The samples were also followed by measuring the absorption at 214 nm.

To test the antigen binding of the Bet v 1 specific antibodies, a sample of diluted antibody was incubated overnight at room temperature with 0.75 mg Protein-G sepharose (Amersham Biosciences, Uppsala, Sweden) in 750 µl PBS/AT (PBS supplemented with 0.3% BSA, 0.1% Tween-20, 0.05% NaN3) together with 50 µl diluted $^{125}$I-labelled Bet v 1 or $^{125}$I-labelled Fel d 1. Bet v 1 was iodinated by the chloramine-T method with carrier free $^{125}$I (Amersham Biosciences, Uppsala, Sweden) as described in Aalberse et al. (Serological aspects of IgG4 antibodies. 1983. 130:722-726). After washing the Sepharose suspension with PBS-T (PBS supplemented with 0.1% Tween-20), the bound radioactivity was measured. The results were expressed as the amount of radioactivity relative to the amount added.

The Bet v 1 binding activity of the hingeless Betv1-HG eluted in one peak, which was more retained than the elution peak of purified Betv1-IgG4 (IgG4 anti Bet v 1) containing an intact hinge (FIG. 9). Calibration of this column using globular proteins showed that the Betv1-HG eluted in fractions corresponding to proteins with a molecular size of ~70 kD (data not shown). These data support our observations that hingeless IgG4 exists as half-molecules and, in contrast to reported hingeless IgG1 and IgG4 molecules (Silverton E W et al., Proc Natl Acad Sci USA 74, 5140 (1977); Rajan S S et al., Mol Immunol 20, 787 (1983); Horgan C et al., J Immunol 150, 5400 (1993)), does not associate via non-covalent interactions into tetrameric molecules.

Example 49

Functional Characterization of Betv1-IgG4 and Betv1-HG Antibodies

Previously was shown that, in contrast to serum-derived antigen specific IgG4, in vitro produced monoclonal IgG4 antibodies are able to crosslink antigen like IgG1 antibodies and are therefore bivalent antibodies (Schuurman J et al., Immunology 97, 693 (1999); Aalberse R C et al., Immunology 105, 9 (2002)). The ability to crosslink antigen of Betv1-IgG1, Betv1-IgG4 and Betv1-HG was determined by a Radio Immuno Assay using Sepharose bound Bet v 1 and $^{125}$I labelled antigen. Herefore, Birch pollen Sepharose was prepared. Briefly, Birch pollen extract (Allergon, Ängelholm, Sweden) was coupled to CNBr-activated Sepharose 4B (Amersham Biosciences, Uppsala, Sweden) according to the instructions of the manufacturer. Subsequently, the Sepharose was resuspended in PBS supplemented with 0.3% BSA, 0.1% Tween-20, 0.05% NaN$_3$.

To examine the ability of the antibody to crosslink Sepharose bound antigen to $^{125}$I labelled antigen, 50 µl of diluted antibody was incubated overnight at room temperature with 750 µl Sepharose in PBS/AT. Next, the Sepharose suspension was washed with PBS-T, after which the suspension was incubated overnight at room temperature with 50 µl diluted $^{125}$I labelled Bet v1 in a total volume of 750 µl PBS/AT. Finally, the Sepharose was washed with PBS-T and bound radioactivity was measured. The results were expressed as the amount of radioactivity bound relative to the amount of radiolabel added.

As can be seen in FIG. 10, all three antibodies were antigen specific and showed good binding to radiolabelled Betv1.

In FIG. 11 is shown that Betv1-IgG1 and Betv1-IgG4 are able to crosslink Sepharose-bound Bet v 1 to radiolabelled Bet v 1. The IgG1 and IgG4 antibody behave as bivalent antibodies. The Betv1-HG antibody was not able to crosslink the Betv1 antigen and therefore demonstrated monovalent binding.

Example 50

Pharmacokinetic Evaluation of an IgG4 Hingeless Mutant Antibody, Compared to Normal IgG1, IgG4 and IgG1 Fragments Twenty-five SCID mice (C.B-17/IcrCrl-scid-BR, Charles-River) with body weights between 24 and 27 g were used for the experiment. The mice were housed in a barrier unit of the Central Laboratory Animal Facility (Utrecht, The Netherlands) and kept in filter-top cages with water and food provided ad libitum. All experiments were approved by the Utrecht University animal ethics committee.

Monoclonal antibodies were administered intravenously via the tail vein. 50 µl blood samples were collected from the saphenal vein at 1 hour, 4 hours, 24 hours, 3 days, 7 days, 14 days, 21 days and 28 days after administration. Blood was collected into heparin containing vials and centrifuged for 5 minutes at 10,000 g. Plasma was stored at −20° C. for determination of mAb concentrations.

In this experiment the clearance of the hingeless IgG4 variant (7D8-HG, lot 570-003-EP) was compared with that of normal human IgG4 (7D8-IgG4, lot 570-002-EP), a IgG1 variant (7D8-IgG1, lot 793-001-EP), F(ab')$_2$ (7D8-G1-F(ab') 2, lot 815-004-XX) and Fab fragments (7D8-G1-Fab, 815-003-X) of the latter mAb. Each antibody was administered to 5 mice, at a dose of 0.1 mg in 200 µl per mouse.

Human IgG concentrations were determined using a sandwich ELISA. Mouse mAb anti-human IgG-kappa clone MH19-1 (#M1272, CLB Sanquin, The Netherlands), coated to 96-well Microlon ELISA plates (Greiner, Germany) at a concentration of 100 ng/well was used as capturing antibody. After blocking plates with PBS supplemented with 2% chicken serum, samples were added, serially diluted in ELISA buffer (PBS supplemented with 0.05% Tween 20 and 2% chicken serum), and incubated on a plate shaker for 1 h at room temperature (RT). Plates were subsequently incubated with peroxidase-labeled F(ab')$_2$ fragments of goat anti-human IgG immunoglobulin (#109-035-097, Jackson, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

SCID mice were chosen because they have low plasma IgG concentrations and therefore relatively slow clearance of IgG. This provides a PK model that is very sensitive for detecting accelerated clearance due to diminished binding of the Fcγ-part to the neonatal Fc receptor (FcRn).

Pharmacokinetic analysis was done by determining the area under the curve (AUC) from the concentration-time curves, with tail correction. The plasma clearance rate was calculated as Dose/AUC (ml/day). Statistical testing was performed using GraphPad PRISM vs. 4 (Graphpad Software).

FIG. 12 shows a semilogarithmic plot of the concentrations in time. The initial plasma concentrations were in the same order for all intact mAbs 85-105 ug/ml, including the hingeless variant. These initial concentrations correspond to a central distribution volume of about 1 ml, which is consistent with distribution into the plasma compartment of the mice. For the F(ab')2 and Fab fragments lower initial concentrations were observed, 75 and 4 ug/ml, respectively. For the Fab fragments this is likely due to rapid extravascular distribution within the first hour after administration.

FIG. 13 shows the clearance rates calculated for the individual mice. The clearance rate of the hingeless variant was 3 to 4 times higher than that of normal IgG1 and IgG4. However, it was more than 10 times slower than that of F(ab')2 fragments and more than 200 times slower than the clearance of Fab fragments.

Example 51

Pharmacokinetic Evaluation of an IgG4 Hingeless Mutant Antibody Compared to Normal IgG4 and IgG1 F(ab)2 Fragments in Immune-Competent Mice Twelve 8-week old Balb/c mice (Balb/CAnNCrl, Charles-River) were used for the experiment. The mice were housed in a barrier unit of the Central Laboratory Animal Facility (Utrecht, The Netherlands) and kept under sterile conditions in filter-top cages with water and food provided ad libitum. All experiments were approved by the Utrecht University animal ethics committee.

Monoclonal antibodies were administered intravenously via the tail vein. 50 µl blood samples were collected from the saphenal vein at 1 hour, 4 hours, 24 hours, 3 days, 7 days, and 10 days after administration. Blood was collected into heparin containing vials and centrifuged for 5 minutes at 10,000 g. Plasma was stored at $-20°$ C. for determination of mAb concentrations.

In this experiment the plasma clearance rate of the hingeless IgG4 variant (7D8-HG, lot 570-003-EP) was compared with that of normal human IgG4 (7D8-IgG4, lot 570-002-EP), a F(ab')$_2$ fragments from 7D8 IgG1 (7D8-G1-F(ab')$_2$, lot 815-004-XX). Each antibody was administered to 4 mice, at a dose of 0.1 mg in 200 µl per mouse, corresponding to a dose of 4 mg per kg of body weight.

Human IgG plasma concentrations were determined using a sandwich ELISA. Mouse mAb anti-human IgG-kappa clone MH19-1 (#M1272, CLB Sanquin, The Netherlands), coated to 96-well Microlon ELISA plates (Greiner, Germany) at a concentration of 100 ng/well was used as capturing antibody. After blocking plates with PBS supplemented with 2% chicken serum, samples were added, serially diluted in ELISA buffer (PBS supplemented with 0.05% Tween 20 and 2% chicken serum), and incubated on a plate shaker for 1 h at room temperature (RT). After washing, the plates were subsequently incubated with peroxidase-labeled F(ab')$_2$ fragments of goat anti-human IgG immunoglobulin (#109-035-097, Jackson, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

Balb/c mice were chosen because they have normal IgG production and therefore faster clearance of IgG than SCID mice. This provides a mouse model in which the administered antibodies have to compete with endogenous mouse IgG for binding to the neonatal Fc receptor (FcRn).

FIG. 15 shows a semilogarithmic plot of the concentrations in time. The initial plasma concentrations were all in the order of 100 µg/ml, which is consistent with an initial distribution into the plasma compartment of the mice. The clearance of the hingeless IgG4 variant was only slightly faster than that of normal IgG4. Importantly, the clearance of the hingeless variant was much slower than that of F(ab')$_2$ fragments, which have a comparable molecular size.

This experiment indicates that the Fc-part has a favorable effect on the plasma residence time in mice having a normal immune system and provides an indication of a functional interaction with the neonatal Fc receptor (FcRn) also in the presence of endogenous IgG.

Example 52

Pharmacokinetic Evaluation of an IgG4 Hingeless Mutant Antibody in Human IgG-Supplemented SCID Mice Sixteen SCID mice (C.B-17/IcrCrl-scid-BR, Charles-River) with body weights between 18 and 22 g were used for the experiment. The mice were housed in a barrier unit of the Central Laboratory Animal Facility (Utrecht, The Netherlands) and kept under sterile conditions in filter-top cages with water and food provided ad libitum. All experiments were approved by the Utrecht University animal ethics committee.

Immunodeficient SCID mice were chosen for studying the pharmacokinetics of the hingeless IgG4 variant, because these mice do not develop antibody responses to human proteins which may affect clearance studies with durations of more than one week. These IgG-deficient mice were supplemented with a high dose of intravenous immunoglobulin (human multidonor polyclonal IgG) to study the clearance of hingeless IgG4 mutant in the presence of human IgG at physiologically relevant concentrations. This provides a mouse model which better represents the conditions in humans, because 1) association of hingeless IgG4 into a bivalent form is prevented by the presence of IVIG, and 2) hingeless IgG4 has to compete with other IgG for binding to the neonatal Fc receptor (FcRn) (Bazin et al. (1994) J. Immunol. Methods 172:209). Binding to FcRn protects IgG from intracellular degradation after endocytosis and is responsible for its long plasma half-life.

In this model the plasma clearance was studied of variants from the human CD20 specific human mAb clone 7D8. The clearance rate of the hingeless IgG4 variant (7D8-HG, lot 992-001-EP) was compared with that of normal human IgG4 (7D8-IgG4, lot 992-002-EP), of F(ab')$_2$ fragments from 7D8 IgG1 (7D8-F(ab')$_2$, lot 892-020-XX). In addition, a preparation of the hingeless variant tested that was enzymatically deglycosylated (TH3001-7D8-HG deglyc, lot 991-004-EP). Each antibody was administered to 4 mice via the tail vein, at a dose of 0.1 mg in 200 µl, corresponding to a dose of about 5 mg per kg of body weight. The monoclonal antibodies were administered in a 1:1 mixture with Intravenous Immunoglobulin (60 mg/ml, Sanquin, The Netherlands, JFK108ST, charge#04H04H443A). The total injected volume was 400 µl/mouse, giving an IVIG dose of 12.5 mg per mouse.

Fifty µl blood samples were collected from the saphenal vein at 15 minutes, 5 hours, 24 hours, 2 days, 3 days, 7 days, and 10 days after administration. Blood was collected into heparin containing vials and centrifuged for 10 minutes at 14,000 g. Plasma was stored at $-20°$ C. for determination of mAb concentrations. Plasma concentrations of the 7D8 variants were determined using a sandwich ELISA. A mouse mAb anti-7D8-idiotype antibody (clone 2F2 SAB 1.1 (LD2), lot 0347-028-EP) was used as capturing antibody. After blocking plates with PBS supplemented with 0.05% Tween and 2% chicken serum, samples were added, serially diluted in ELISA buffer (PBS supplemented with 0.05% Tween 20 and 2% chicken serum), and incubated on a plate shaker for 2 h at room temperature (RT). The infused antibodies were used as reference. After washing, the plates were subsequently incubated with peroxidase-labeled goat anti-human F(ab')$_2$ specific (109-035-097, Jackson Immunoresearch, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm. Total human IgG plasma concentrations were determined using a similar ELISA. Mouse mAb anti-human IgG-kappa clone MH16 (#M1268, CLB Sanquin, The Netherlands) was used as capturing antibody. Peroxidase-labeled goat anti-human IgG immunoglobulin (#109-035-098, Jackson, West Grace, Pa.) was used for detection.

Pharmacokinetic analysis was done by determining the area under the curve (AUC) from the concentration-time curves, with tail correction. The plasma clearance rate was calculated as Dose/AUC (ml/day). Statistical testing was performed using Graph Pad PRISM vs. 4 (Graphpad Software).

FIG. 20 shows in the upper panel semi-logarithmic plots of the concentrations of the mAb 7D8 variants in time and in the lower panel the total human IgG concentrations. The initial total human IgG concentrations were on average 2.3 mg/ml and declined to 0.47 mg/ml after 10 days. The initial plasma concentrations of 7D8 IgG4 and IgG4 HG variants were in the range of 94 to 180 µg/ml, which is consistent with an initial distribution into the plasma compartment of the mice. For the F(ab')2 fragments the initial concentrations were somewhat lower, on average 62 µg/ml. The upper panel makes clear that the clearance of the hingeless variant, including the deglycosylated preparation, is somewhat faster than that of intact IgG4, but much slower than that of F(ab')2 fragments. The table below shows the clearance rates calculated from the concentration-time curves. The clearance rate of the hingeless variant was 2 to 3 times higher than that of normal IgG4. However, it was almost 10 times slower than that of F(ab')$_2$ fragments. Importantly, deglycosylation had no significant effect on the rate of clearance of the hingeless IgG4 variant.

| PLASMA CLEARANCE RATE (D/AUC) in ml/day per kg | IgG1 F(ab')2 | IgG4 | IgG4 HG | IgG4 HG deglyc |
|---|---|---|---|---|
| Mean | 380 | 14 | 39 | 29 |
| Lower 95% CI of mean | 346 | 12 | 25 | 19 |
| Upper 95% CI of mean | 415 | 17 | 53 | 38 |
| Number of values | 4 | 4 | 4 | 4 |

Thus, also in the presence of human IgG in physiologically relevant concentrations the clearance of the hingeless variant is much slower than that of F(ab')2 fragments, which have a comparable molecular size. This experiment demonstrates that, also in the presence of competing human IgG at physiologically relevant concentrations, the hingeless IgG4 variant is capable of functional interaction with the neonatal Fc receptor (FcRn). Furthermore, this experiment indicates that the glycosylation of the hingeless IgG4 variant does not affect plasma clearance and that non-glycosylated hingeless IgG4 has a similar half-life in vivo as the fully glycosylated from.

Example 53

Pharmacokinetic Evaluation of an IgG4 Hingeless Mutant Antibody Compared to Normal IgG4 and IgG1 F(ab)$_2$ Fragments in FcRn –/– Mice This experiment was performed to investigate whether the IgG4 hingeless mutant is capable of interacting with the neonatal Fc receptor (FcRn), which is responsible for the long plasma half-life of IgG by protecting IgG from intracellular degradation after endocytosis. B2M knockout mice were used in this experiment because they do not express FcRn.

Twelve female C57Bl/6 B2M knockout mice (Taconic model B2MN12-M, referred to as FcRn –/– mice), and twelve female C57Bl/6 wild type control mice (Taconic, model nr. B6, referred to as WT mice) were used for the experiment. The mice were housed in a barrier unit of the Central Laboratory Animal Facility (Utrecht, The Netherlands) and kept in filter-top cages with water and food provided ad libitum. All experiments were approved by the Utrecht University animal ethics committee.

The plasma clearance was studied of variants from the human CD20 specific human mAb clone 7D8. The clearance rate of the hingeless IgG4 variant (7D8-HG, lot 992-001-EP) was compared with that of normal human IgG4 (7D8-IgG4, lot 992-002-EP), F(ab')$_2$ fragments from 7D8-IgG1 (7D8-G1-F(ab')$_2$, lot 892-020-XX).

Monoclonal antibodies were administered intravenously via the tail vein. Each antibody was administered to 4 mice at a dose of 0.1 mg in 200 µl per mouse, corresponding to a dose of 5 mg per kg of body weight. Fifty µl blood samples were collected from the saphenal vein at 10 minutes, 5 hours, 24 hours, 2 days, 3 days, 7 days, and 10 days after administration. Blood was collected into heparin containing vials and centrifuged for 10 minutes at 14,000 g. Plasma was stored at –20° C. for determination of mAb concentrations. Human IgG plasma concentrations were determined using a sandwich ELISA in which mouse mAb anti-human IgG-kappa clone MH19-1 (#M1272, CLB Sanquin, The Netherlands), coated to 96-well Microlon ELISA plates (Greiner, Germany) at 100 ng/well was used as capturing antibody. After blocking plates with ELISA buffer (PBS supplemented with 0.05% Tween and 2% chicken serum), samples were added, serially diluted in ELISA buffer. Serial dilutions of the corresponding infused antibody preparations were used as reference. After incubation and washing, the plates were incubated with peroxidase-labeled AffiniPure Goat Anti-Human IgG, F(ab')$_2$ Fragment Specific (#109-035-097, Jackson Immunoresearch, West Grace, Pa.) and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm. Pharmacokinetic analysis was done by determining the area under the curve (AUC) from the concentration-time curves, with tail correction. The plasma clearance rate was calculated as Dose/AUC (ml/day). Statistical analysis was performed using GraphPad PRISM vs. 4 (Graphpad Software).

FIG. 21 shows a semi-logarithmic plot of the concentrations in time. The initial plasma concentrations were all in the order of 100 µg/ml, which is consistent with an initial distribution in the plasma compartment of the mice. The table below shows the plasma clearance rates calculated from the concentration-time curves of individual mice.

| PLASMA CLEARANCE RATE ml/day per kg | F(ab')2 WT | F(ab')2 FcRn-/- | IgG4 WT | IgG4 FcRn-/- | IgG4 HG WT | IgG4 HG FcRn-/- |
|---|---|---|---|---|---|---|
| Mean | 183 | 159 | 12 | 45 | 15 | 83 |
| Std. Deviation | 19 | 19 | 10 | 3 | 4 | 29 |
| Number of values | 4 | 4 | 4 | 4 | 4 | 4 |
| Significance difference: Pvalue (t-test) | 0.1265 ns | | 0.0009 *** | | 0.0033 ** | |

For F(ab')$_2$ fragments no significant differences were observed between wild type (WT) and knockout (FcRn -/-) mice. In contrast, for IgG4 and the hingeless IgG4 variant the clearance rates were 3 to 5 times slower in the WT mice compared to that in FcRn -/- mice. This experiment shows that the presence of FcRn has a favorable effect on the plasma residence time of hingeless IgG4. Therefore, it provides evidence that hingeless IgG4 is capable having a functional interaction with FcRn in vivo, which explains its favorable plasma half-life.

Example 54

Functional Analysis of 2F8-HG Anti-EGFr mAb

MAb 2F8 is a human IgG1 monoclonal antibody (mAb) against human Epidermal Growth Factor receptor (EGFr) which is capable to inhibit EGFr signalling by blocking binding of ligands. From this mAb an IgG4 variant, 2F8-IgG4, was made and also a hingeless variant, 2F8-HG.

In the present example, we compared the potency of 2F8-HG with that of 2F8-IgG1 and 2F8-Fab fragments to inhibit ligand-induced EGFr phosphorylation in cells in vitro. This was done both with and without addition of Intravenous Immunoglobulin (IVIG), a polyclonal human IgG preparation, containing all IgG subclasses.

Inhibition of EGFr phosphorylation was measured in a two-step assay using the epidermoid cell line, A431 (ATCC, American Type Culture Collection, Manassas, USA). The cells were cultured overnight in 96-wells plates in serum-free medium containing 0.5% human albumin (human albumin 20%, Sanquin, the Netherlands). Next, mAb were added in serial dilution, with or without IVIG (Immunoglobuline I.V., Sanquin) at a fixed final concentration of either 100 or 1000 µg/ml. After 60 minutes incubation at 37° C., 50 ng/ml recombinant human EGF (Biosource) was added to induce activation of non-blocked EGFr. Following an additional 30 minutes incubation, cells were solubilized with lysis buffer (Cell Signaling Technology, Beverly, Mass.), and the lysates were transferred to ELISA plates coated with 1 µg/ml of mouse anti-EGF-R antibodies (mAb EGFR1, BD Pharmingen, San Diego, Calif.). After 2 hours incubation at RT, the plates were washed and binding of phosphorylated EGF-R was detected using a europium-labelled mouse mAb, specific for phosphorylated tyrosines (mAb Eu-N1 P-Tyr-100, PerkinElmer). Finally, DELFIA enhancement solution was added, and time-resolved fluorescence was measured by exciting at 315 nm and measuring emission at 615 nm on an EnVision plate reader (PerkinElmer). Sigmoidal dose-response curves were calculated using non-linear regression (GraphPad Prism 4).

As can be seen in the upper panel of FIG. 14, 2F8-HG was equally effective as 2F8-IgG1 in inhibiting phosphorylation when culture medium was used without addition IVIG. Both mAb were more potent than 2F8-Fab fragments, which bind monovalently to EGFr. The middle and lower panels of FIG. 14 show that addition of IVIG had negligible effect on 2F8-IgG4 and 2F8-Fab. However, it markedly right-shifted the dose-response curve of 2F8-HG, indicating a change in binding characteristics, which is consistent with the idea that under certain conditions 2F8-HG may behave as a bivalent antibody, but dissociates into a monovalent form in the presence of polyclonal human IgG.

Example 55

Proof of Principle

IgG4 Hingeless Against CD89 (CD89-HG) Inhibits IgE-Mediated Asthma in a Mouse Model Pasquier et al. (Pasquier, B et al., Immunity 22, 31 (2005)) showed that FcαRI (CD89 (Monteiro R C et al., Annu Rev Immunol 21, 177 (2003)) has both an anti- and proinflammatory role. Aggregation of FcαRI leads to cell activation by recruitment of Syk and aborting SHP-1 binding. A monomeric interaction with FcαRI inhibits the activating response: SHP-1 is being recruited and impairment of Syk, LAT and ERK phosphorylation occurs.

Fab fragments of an anti-CD89 antibody (clone A77) could inhibit IgG-mediated phagocytosis using human monocytes. Furthermore, IgE-mediated responses in vitro using FcαRI transfected RBL-2H3 cells and in vivo in an IgE-mediated asthma model were inhibited by Fab fragments of this anti-CD89 antibody. In this animal model, FcαRI-transgenic mice (Launay P et al., J Exp Med 191, 1999 (2000)) were sensitized with TNP-OVA. Mice challenged intranasally with IgE-TNP-OVA immune complexes in the presence of A77 Fab-fragments showed reduced bronchial reactivity to methacholine whereas and irrelevant Fab-fragment could reduce the bronchial hyperreactivity.

Proof on principle in vitro of an antigen specific, non-crosslinking, monovalent, non-activating antibody is obtained in the following experiment. Adherent PBMC are incubated with 10 µg/ml A77-HG (IgG4 hingeless) preincubated 24 h with or without irrelevant IgG4 (Genmab BV) or incubated with irrelevant HG antibody for 30 min at 37° C., washed, and incubated at 37° C. for 30 min with Texas-red-conjugated E. coli (50 bacteria/cell) (Molecular Probes, Eugene, Oreg.) opsonized or not with polyclonal rabbit anti-E. coli IgG antibodies according to the manufacturer's instructions. Slides are mounted and examined with a confocal laser microscope. The PBMC receiving opsonized E. coli and A77-HG (pre-incubated with irrelevant IgG4) show reduced phagocytosis of E. coli when compared to PMBC receiving opsonized E. coli and control-HG antibody.

FcαRI-transgenic mice are sensitized with TNP-OVA as described (Pasquier B et al., Immunity 22, 31 (2005)); or alternatively with OVA as described by Deurloo et al. (Deurloo D T et al., Clin Exp Allergy 33, 1297 (2003)). Human FcαRI transgenic mice and littermate controls are immunized twice on day 0 and day 7 intraperitonally with TNP-OVA or OVA (Sigma) in aluminium hydroxide. Mice are challenged intranasally for a few consecutive days with either TNP-OVA complexed with 20 µg anti-DNP-IgE (Zuberi, R I et al., J Immunol 164, 2667 (2000)) or OVA aerosol (Deurloo D T et al., Clin Exp Allergy 33, 1297 (2003)) in the presence of A77-HG (IgG$_4$ hingeless) or an irrelevant hingeless antibody (control-HG).

The mice receive 50 µg A77-HG or control-HG intraperitoneally twice, once during the challenge period and once with the last intranasal challenge. Twelve hours after the final intranasal challenge, the mice are placed in a whole-body plethysmograph chamber (BUXCO Electronics, Sharon Conn., USA), and 300 mM methacholine delivered. Airway resistance is measured after exposure to methacholine. Immunohistological evaluation is performed on lung sections after euthanizing the mice.

The mice receiving A77-HG show a reduced hyper reactivity when compared to the mice receiving the control-HG antibody.

This indicates that a hingeless IgG$_4$ molecule is non-crosslinking, monovalent and non-activating and therefore useful for therapeutic purposes where such inert antibody may be favorable such as in the inhibition of inflammatory reactions through FcαRI.

Example 56

Proof of Concept Study with Hingeless IgG4 cMet (cMet-HG)

The receptor tyrosine kinase c-Met is prominently expressed on a wide variety of epithelial cells. During embryogenesis, cMet and Hepatocyte Growth factor/Scatter factor (HGF/SF) are involved in tissue-specific differentiation, leading to a proper organization of epithelial cells, muscle endothelium, and the nervous and hematopoietic systems. Abnormal cMet signalling has been implicated in tumorogenesis, particularly in the development of invasive and metastatic tumors. As a consequence of enhanced cMet activity, tumor cells may increase their growth rate and become resistant to apoptosis, resulting in a growth and/or survival advantage. Furthermore, cMet activation may lead to cytoskeletal reorganization and integrin activation, as well as to activation of proteolytic systems involved in extracellular matrix degradation, resulting in an increased invasive and metastatic capacity. Inhibition of HGF/SF-cMet signaling, therefore, represents an important therapeutic avenue for the treatment of malignant tumors.

Kong-Beltran et al. in Cancer Cell (2004 volume 6, pages 75-84) raised an antibody (5D5) to the extracellular domain of cMet and inhibited HGF binding. The Fab fragment of anti-Met 5D5 was shown to inhibit HGF-driven cMet phosphorylation, cell motility, migration and tumor growth. They speculate that anti-cMet-5D5-Fab block receptor dimerization by steric hindering.

MAb C6 is a human IgG1 monoclonal antibody (mAb) against human cMet which is capable of binding with high affinity to H441 cells, activate cMet phosphorylation, induce scattering of DU-145 and block HGF binding to cMet in ELISA. From this mAb a Fab fragment (cMet-Fab), an IgG4 variant (cMet-IgG4), and also a hingeless variant was made (cMet-HG).

In a proof-of-concept study with hingeless IgG4 against cMet (cMet-HG) this monovalent antibody inhibited HGF binding, receptor dimerization/activation, cell scattering, and downstream signalling. This experiment was performed both with and without addition of Intravenous Immunoglobulin (IVIG), a polyclonal human IgG preparation, containing all IgG subclasses and with and without rHGF.

DU-145 Scatter Assay

DU-145 (humane prostate carcinoma cell line, ATCC HTB-81) cells were cultured in DMEM+ (containing 500 ml MEM Dulbecco (DMEM-Medium, glucose 4.5 g/ml with NaHCO3, without glutamine, Sigma, D-6546), 50 ml Cosmic Calf Serum (Hyclone SH30087.03), 5 ml of 200 mM/L L-glutamine (Bio Whittaker, BE17-605F), 5 ml sodium pyruvate (Bio Whittaker BE13-115E), 5 ml penicillin/streptamicin (Bio Whittaker, DE17-603E)) and were growing adherent clustered cells. Upon addition of rhHGF (Sigma, H-1404), migration of the cells was induced, which leads to singularized cells. This process was called scattering. Induction or inhibition of scattering was observed by microscopy.

Day 1: cMet, cMet-HG, cMet-Fab, cMet-IgG4 (30/3.0/0.3/0.03 µg/ml), were incubated over night with and without addition of IVIG, 6 mg/ml. DU145 cells were seeded (adherent cells out of T75-culture flask) cell culture supernatant was removed and cells were washed 1 time with 10 ml PBS 2 ml Trypsine/EDTA was added (37° C.) and cells were incubated at 37° C. for 1-2 min. The cells were removed from the surface of the culture flask by tapping and the Trypsine/EDTA reaction was stopped with stored culture supernatant. The cells were counted and a suspension was prepared of $1*10^4$ cells/ml in fresh culture medium and 50 µl/well was plated into 96-well plate (Sterile flat bottom Costar, 3596) (final density 1000 cells/well). Cells were cultured for 15-24 h at 37° C. and 5% CO$_2$ in an incubator.

Day 2: Medium was replaced by fresh medium, 40 µl/well. 40 ul of the preincubated antibody was added to the cells and cells were incubated at 37° C. in an incubator for 60 min, after which 40 µl/well medium or 60 ng/ml rh-HGF was added. (Final concentrations were: 10/1.0/0.1/0.01 µg/ml Ab, 2 mg/ml IVIG, 20 ng/ml HGF). Cells were incubated for at least 24 h.

Day 3 and 4: Scattering was observed double-blinded by microscope after 24 h or after 48 h. Morphological characteristics of scattering: cells detach from the surface, show spindle shaped forms (migrate), and most were single cells not in clusters.

Ranking of rh-HGF induced scatter inhibition by antibodies:

3 cells were maximal scattering
2 small inhibition of scattering
1 inhibition of scattering
0 no scattering In this experiment C6-HG pre-incubated with IVIG significantly blocked the HGF induced scattering.

Phosphorylation of the cMet Receptor

A549 cells were cultured in Ham's F12 medium and cMet was not phosphorylated under normal culture conditions. Upon activation by HGF, the cMet receptor becomes phosphorylated. By applying cMet blocking cMet-Fab or cMet-HG with pre-incubation of IVIG the HGF mediated phosphorylation of the receptor was inhibited.

Day 1: cMet-IgG1, cMet-HG (12.5 µg/ml), were incubated over night with and without addition of IVIG, 2.5 mg/ml. A549 cells ($1*10^6$/well) were cultured in a 6 well plate.

Day 2: The culture medium, (containing 500 ml Ham's F12 (Bio Whittaker BE12-615F 50 ml Cosmic Calf Serum (Hyclone SH30087.03), 5 ml of 200 mM/L L-glutamine (Bio Whittalker, BE17-605F), 5 ml penicillin/streptamicin (Bio Whittaker, DE17-603E)) was removed and 800 µl of the preincubated antibody was added to the cells and cells were incubated herewith at 37° C. in an incubator for 15 min, after which 200 µl/well medium or 80 ng/ml rh-HGF was added. (Final concentrations were 10 µg/ml Ab, 2 mg/ml IVIG, 16 ng/ml HGF). After incubation for another 15 min, the incubation medium was removed and the cells were washed twice with ice cold PBS, and 250 μl RIPA lysis buffer (containing 50 mM Tris, pH 7.5, 0.5% Na deoxycholate and 0.1% Nonidet P40, 150 mM NaCl, 0.1% SDS, 2 mM vanadate and Complete (Protease inhibitor, Roche 1836170) was added, and the plate was gently rotated for 10 min. at 4° C. The lysates were transferred into pre-cooled tubes (Eppendorf) and centrifuged at highest speed for 30 min. at 4° C. DNA was removed and the lysate was flash frozen in $N_2$ after a fraction was used to measure BCA protein content analysis (Pierce). Lysates were stored at −80° C. until analysis by Western-blot. 10 μg reduced samples were undergoing electrophoresis on 4-20% Tris-HCl Criterion Precast gel (Biorad 345-0033) and Western blotting on a nitrocellulose membrane (Biorad 162-0114) according standard procedures. The membrane was blocked with blocking solution (containing 5% BSA (Roche, 10735086) in TBST (Tris-HCL 20 mM pH 7.5, NaCl 150 mM, 0.1% Tween 20) for 1.5 hours at room temperature on a roller bank. The membrane was incubated over night at 4° C. with 1:1000 dilution of anti-phospho-Met(pYpYpY 1230 1234 1235)-rabbit IgG, (Abcam, ab5662). After washing 6 times with TBST, the secondary antibodies, goat-anti-rabbit-HRP, Cell Signalling, 7074 (1:2000) in blocking reagent were incubated for 60 min. at room temperature on a roller bank. The membrane was washed 6 times with TBST. Finally the bands were developed with Luminol Enhancer stop solution (Pierce 1856145) and analyzed on a Lumiimager.

cMet-HG pre-incubated with IVIG inhibits the HGF mediated phosphorylation of the receptor.

FIG. 22

DU-145 cells were cultured and incubated with a serial dilution of (A) cMet-Fab, cMet-Fab and IVIG, cMet-Fab and HGF, cMet-Fab and IVIG and HGF (B) cMet-HG, cMet-HG and IVIG, cMet-HG and HGF, cMet-HG and IVIG and HGF. Scattering was observed double-blinded (scored by 14 people) by microscope after 48 h and the averaged score±SEM is plotted.

cMet-Fab with or without IVIG (A) and cMet-HG pre-incubated with IVIG (B) significantly blocked the HGF induced scattering dose-dependently.

FIG. 23

DU-145 cells were cultured and incubated with 10 μg/ml of (A) cMet-Fab, cMet-Fab and IVIG, cMet-Fab and HGF, cMet-Fab and IVIG and HGF (B) cMet-HG, cMet-HG and IVIG, cMet-HG and HGF, cMet-HG and IVIG and HGF. Scattering was observed double-blinded (scored by 14 people) by microscope after 48 h.

cMet-Fab with or without IVIG and cMet-HG pre-incubated with IVIG significantly inhibited the HGF induced scattering. For statistical analysis a two-tailed Wilcoxon signed ranked test was done with a hypothetical median value of 3 (maximal scattering).

FIG. 24

Extracts prepared from A549 cells incubated with cMet-HG (lane 1), cMet-HG and IVIG (lane 2), cMet-HG and HGF (lane 3), cMet-HG, IVIG and HGF (lane 4), cMet-IgG1 (lane 5), cMet-IgG1 and IVIG (lane 6) were resolved by SDS-PAGE on a 4-20% Tris-HCl Criterion Precast gel and Western blotting on a nitrocellulose membrane. The membrane was incubated over night at 4° C. with anti-phospho-Met(pY-pYpY 1230 1234 1235)-rabbit IgG, (Abcam, ab5662). After washing with TBST, the secondary antibodies, goat-anti-rabbit-HRP, Cell Signalling, 7074 in blocking reagent were incubated for 60 min. at room temperature on a roller bank. The membrane was washed 6 times with TBST. Finally the bands were developed with Luminol Enhancer stop solution and analyzed on a Lumiimager. The Western blot shows a 169 Kd band indicating phospho-Met(pYpYpY 1230 1234 1235).

Example 57

In Vitro Evaluation of an IgG4 Hingeless Mutant Antibody Targeting the Epidermal Growth Factor Receptor (EGFr)

Binding Avidity and Induction of Antibody Dependent Cell-Mediated Cytotoxicity (ADCC)

In this experiment an IgG4 hingeless mutant antibody targeting the Epidermal Growth Factor Receptor (EGFr), mAb 2F8-HG was compared to an IgG4 version, an IgG1 version and Fab fragments, referred to as 2F8-IgG4, 2F8-IgG1 and 2F8-Fab, respectively. The in vitro evaluation comprised the avidity of binding to EGFr in an ELISA and the induction of ADCC.

ELISA.

Binding affinities were determined using an ELISA in which purified EGF-R (Sigma, St Louis, Mo.) was coated to 96-well Microlon ELISA plates (Greiner, Germany), 50 ng/well. Plates were blocked with PBS supplemented with 0.05% Tween 20 and 2% chicken serum. Subsequently, samples, serially diluted in a buffer containing 100 μg/ml polyclonal human IgG (Intravenous Immunoglobulin, IVIG, Sanquin Netherlands) were added and incubated for 1 h at room temperature (RT). Plates were subsequently incubated with peroxidase-conjugated rabbit-anti-human kappa light chain (DAKO, Glostrup, Denmark) as detecting antibody and developed with 2,2'-azino-bis(3-ethylbenzthiazoline-6-sulfonic acid) (ABTS; Roche, Mannheim, Germany). Absorbance was measured in a microplate reader (Biotek, Winooski, Vt.) at 405 nm.

FIG. 16 shows that the binding curves of the 2F8-HG and 2F8-Fab are super-imposable and clearly right-shifted with respect to the binding curves of IgG1 and IgG4. This difference in avidity for the EGFr coat is consistent with the idea that, in the presence of IVIG, 2F8-HG binds monovalently, just like Fab fragments.

Antibody Dependent Cell-Mediated Cytotoxicity (ADCC).

The capacity to induce effector cell-dependent lysis of tumor cells was evaluated in Chromium-51 ($^{51}$Cr) release assay. Target A431 cells (2–5×10$^6$ cells) were labeled with 100 μCi Na$_2$$^{51}$CrO$_4$ (Amersham Biosciences, Uppsala, Sweden) under shaking conditions at 37° C. for 1 h. Cells were washed thrice with PBS and were re-suspended in culture medium 1×10$^5$ cells/ml. Labeled cells were dispensed in 96 wells plates (5×10$^3$, in 50 μl/well) and pre-incubated (RT, 30 minutes) with 50 μl of 10-fold serial dilutions of mAb in culture medium, ranging from 20 μg/ml to 0.02 ng/ml (final concentrations). Culture medium was added instead of antibody to determine the spontaneous $^{51}$Cr release, tritonX100 (1% final concentration) was added to determine the maximal $^{51}$Cr release. Thereafter, PBMC were added to the wells (5×10$^5$/well) and cells were incubated at 37° C. overnight. The next day, supernatants were collected for measurement of the $^{51}$Cr release by determination of the counts per minute (cpm) in a gamma counter. Percentage of cellular cytotoxicity was calculated using the following formula:

% specific lysis=(experimental release (cpm)−spontaneous release (cpm))/(maximal release (cpm)−spontaneous release (cpm))×100 where maximal $^{51}$Cr release determined by adding triton X-100 to target cells, and spontaneous release was measured in the absence of sensitizing antibodies and effector cells.

FIG. 17 shows that 2F8-HG induces no ADCC, like 2F8-IgG4, whereas 2F8-IgG1 is very potent in this respect.

Example 58

AlgoNomics' Epibase® platform was applied to IgG4 constant hingeless monovalent antibody. In short, the platform analyzes the HLA binding specificities of all possible 10-mer peptides derived from a target sequence (Desmet et al. 1992, 1997, 2002, 2005). Profiling is done at the allotype level for 20 DRB1, 7 DRB3/4/5, 14 DQ and 7 DP, i.e. 48 HLA class II receptors in total.

Epibase® calculates a quantitative estimate of the free energy of binding ☐Gbind of a peptide for each of the 48 HLA class II receptors. These data are then further processed as follows: Peptides are classified as strong (S), medium (M), weak and non (N) binders.

No strong and only 1 medium binding epitope was encountered within the constant region of IgG4 hingeless monovalent antibody. This single neo-epitope created a medium DRB1*0407 binder. DRB1*0407 is a minor allotype, present in less than 2% of the Caucasian population. In addition, a single epitope of medium strength is insignificant in the total epitope count of even the least immunogenic antibody.

In conclusion the hingeless monovalent IgG4 antibody is predicted to be very unlikely to be immunogenic.

Example 59

Background of Studies and Materials Used in Examples 59 and 60 Presented for Unibody-CD4

In vitro and in vivo experiments were performed to address the ability of a human monoclonal antibody against CD4 (HuMax-CD4) to inhibit HIV-1 infection. The antibody is directed against domain 1 of CD4 and overlaps with the HIV-1 gp120 binding site on CD4.

The present example (59) shows that Fab fragments of anti-CD4 antibodies inhibits the infection of CD4-CCR5 cells or CD4-CXCR4 cells by different primary isolates and T-cell line adapted HIV viruses. The 1050 values of inhibition are in the range of the EC50 values of HuMax-CD4 binding to sCD4 and cell bound CD4 (data not shown), implicating inhibition of HIV-1 envelope binding to CD4 as a mechanism of inhibition. In general Fab fragments of HuMax-CD4 inhibit with a 10 times lesser efficiency than the whole antibody which is as expected from the difference in avidity between the Fab and the whole antibody.

Example 60 shows that in mice treated with HuMax-CD4 a lesser decline in CD4/CD8 ratio compared is observed than in IgG control treatment groups, indicating that HuMax-CD4 protects against depletion of CD4 positive cells by HIV-1. Furthermore, HuMax-CD4 treatment leads to a decrease in the amount of HIV-1 RNA copies in the blood in time, whereas the IgG control treatment does not induce this decrease. The in vitro data indicate that anti-CD4 antibodies can protect against HIV-1-induced CD4 depletion, and decrease the magnitude of HIV infection and viral load.

Norris et al have published on the treatment of HIV-1 infected individuals with a whole anti-CD4 (domain 2) antibody of the IgG4 subclass.

Efficacy results demonstrated significant antiviral activity at primary endpoint (Week 24).

Durable response suggested by Week-48 results in patients receiving TNX-355.

TNX-355 10 mg/kg+OBR demonstrated a 0.96 log 10 reduction in HIV-RNA from baseline at Week 48 versus 0.14 log 10 decrease for placebo+OBR (p<0.001).

TNX-355 15 mg/kg+OBR demonstrated a 0.71 log 10 reduction in HIV-RNA from baseline at Week 48 versus 0.14 log 10 for placebo+OBR (p=0.009).

Treatment with TNX-355+OBR was associated with statistically significant and clinically-meaningful increases in CD4+ cells at Week 48 in both the 10 mg/kg arm (+48 cells, p=0.031) and the 15 mg/kg (+51 cells, p=0.016) arms versus the placebo increase (+1 cell).

Literature

Zwick M. B., Wang M., Poignard P., Stiegler G., Katinger H., Burton D. R., and Parren P. W. H. I. 2001. Neutralization synergy of human immunodeficiency virus type 1 primary isolates by cocktails of broadly neutralizing antibodies. *J Vir* 75:12198.

Poignard P., Sabbe R., Picchio G. R., Wang M., Gulizia R. J., Katinger H., Parren P. W. H. I., Mosier D. E., and Burton D. R. 1999. Neutralizing antibodies have limited effects on the control of established HIV-1 infection in vivo. *Immunity* 10:431.

Norris D., Moralis J., Gathe J., Godafsky E., Garcias F., Hardwick R., and Lewis S. 2006. Phase 2 efficacy and safety of the novel viral-entry inhibitor, TNX-355, in combination with optimized background regimen (OBR). *XVI International AIDS Conference, Toronto, Canada*

In Vitro HIV-1 Neutralization by HuMax-CD4 Whole Antibody and Fab Fragments of the HuMax-CD4 Antibody The method is described in detail in Zwick et al 2001. In summary, the degree of virus neutralization by antibody was measured by luciferase activity. Viruses competent for a single round of replication were produced by cotransfections of the appropriate virus constructs in a modified pSVIIIenv vector (for instance primary isolates: JR-CSF, JR-FL, SF162, ADA, YU2, 89.6, US143 and T cell line adapted virus: IIIB) and pNL4-3.lec.R-E-. Viruses were pre-incubated with various amounts of antibody (before addition determined to yield about 100,000 counts) to U87.CD4.CCR5 cells (primary isolates) or CD4-CXCR4 cells (for IIIB), and culturing for 3 days. The wells were washed, incubated with luciferase cell culture lysis reagent, and lysates were transferred to opaque assay plate to measure luciferase activity on a luminometer using luciferase assay reagent. For neutralization HuMax-CD4 and Fab fragments of HuMax-CD4 were tested.

According to the method described, the virus constructs YU2, IIIB, ADA, 89.6, US143, JR-FL, JR-CSF, and SF 162 were used in the in vitro neutralization assay using the luciferase assay expression system. HIV-1 IIIB is a T-cell line adapted virus, all the other viruses are primary isolates of HIV-1. The HuMax-CD4 antibody and Fab fragments of HuMax-CD4 were added in a 1:2 dilution response starting at the concentrations indicated in FIG. 25. In FIG. 27, the curves fitted by a 4 parameter logistic analysis are given for the HuMax-CD4 and the Fab fragments of HuMax-CD4 and in FIG. 25 the IC50 calculated from these fits are indicated. The data show that the HuMax-CD4 antibody inhibited the infection of all the viruses tested, and in general did this with a 10 times better efficiency than the Fab fragments (exceptions are YU2 and JR-CSF). The EC50 for binding of HuMax-CD4 to sCD4 has been determined to be about 0.3-1 nM. The IC50 values of inhibition are in the range of these EC50 values, indicating that receptor occupation by HuMax-CD4 relates to degree of infection inhibition.

Our experiments provide proof-of-principle for an effective inhibition of HIV-1 infection of both CXCR4 and CCR5HIV-1 co-receptor expressing cells by monovalent binding of an anti-CD4 antibody (i.e. Fab fragment). This provides evidence that a similar inhibition could be accomplished by a HG anti-CD4 antibody.

Example 60

Protection of CD4+ T Cell Depletion in In Vivo hu-PBMC-SCID Mouse Model of HIV Infection The experimental procedure is described in detail in Poignard et al 1999. In summary, CB-17 SCID mice were reconstituted with about $25\times10^6$ normal human PBMC (peripheral blood mononuclear cells). About two weeks later the animals were infected with HIV-1 (HIV-1$_{JR-CSF}$). Three days later the animals are treated with 1 mg/ml HuMax-CD4, or a human IgG isotype control antibody, or no treatment delivered intraperitoneally. Blood samples were taken at 1 hr, 6 hrs, day 1, 2, 3, 6, 9, 13, and 15 after injection, and two weeks later the animals were euthanized and FACS analysis performed to determined the % of human cells (using H2Kd-PE and human CD3-APC) and the CD4/CD8 ratio (using CD4-PE and CD8-APC double staining). Furthermore, plasma viral load was measured by measuring HIV-1 RNA levels by the quantitative Roche RT PCR assay. In addition, with a direct sCD4 binding ELISA (coat of sCD4 on the plate, and detection by anti-Fc polyclonal antibody) the concentrations of HuMax-CD4 in plasma were determined.

In FIG. 28 the plasma levels of the animals are given. It is concluded that HuMax-CD4 injection leads to high HuMax-CD4 plasma concentrations that were still above 100 µg/ml at day 15. The non treated mice gave no measurable values above background.

In FIG. 26 the cell numbers harvested from the mice at the end of the experiment are given. The data indicate that HIV-1 infection led to an extensive decrease in CD4 positive T cells as indicated by the drop in CD4/CD8 ratio. This shows that CD4 positive T cells are rapidly depleted from the blood by HIV-1 in contrast to the constant levels in non-infected mice. The mice treated ip with HuMax-CD4 had a much smaller decline in CD4/CD8 ratio, which shows that HuMax-CD4 provides protection of against depletion of CD4 positive cells by HIV-1. In FIG. 29 the HIV-1 RNA copies per ml blood are given in time, and these data indicate that the HuMax-CD4 treatment led to a decrease in the amount of HIV-1 RNA copies in the blood in time, whereas the isotype control antibody did not lead to a decrease.

Our experiment provides proof of principle for the protection against CD4 cell depletion in HIV-1 infection in vivo. The protection against depletion is observed even though the whole anti-CD4 antibody has CD4 depleting properties it self. This indicates that stronger protection against HIV-1-induced T cell depletion can be obtained by treatment with a monovalent non-depleting anti-CD4 antibody such as an anti-CD4 HG antibody. Proof of principle for HIV-1 neutralization by anti-CD4 HG and protection against CD4 depletion can be obtained in a similar experimental set-up. This provides evidence that HuMax-CD4 HG showing a long in vivo half life, could inhibit HIV-1 infection and HIV-1 viral load and protect from depletion of CD4 positive cells.

Summary of the Results

The data presented in the examples shows that expression of a hingeless IgG4 antibody by destroying the splice donor site of the hinge exon results in hingeless IgG4 half-molecules (one heavy and one light chain combined). The presence of IgG4 hingeless half-molecules is confirmed by SDS-PAGE under non-reducing conditions, mass spectrometry, size exclusion chromatography and radio immuno assay the absence of cross-linking abilities. The hingeless antibodies retain the same antigen binding specificity as natural format IgG1 and IgG4 antibody molecules. This is shown for two hingeless antibodies with different specificity, 7D8-HG (specific for the B-cell antigen CD20) and Betv1-HG (specific for the Birch pollen antigen Bet v 1). C1q binding of 7D8-HG is absent and only minor complement-dependent cellular toxicity (ADCC) is observed (comparable to the natural format 7D8-IgG4 antibody). Monovalency of the hingeless half-molecule is shown in the crosslinking experiment using Betv1-HG. Whereas both IgG1 and IgG$_4$ show crosslinking of Sepharose bound Bet v 1 to radiolabelled Bet v 1, the hingeless molecule Betv1-HG is unable to crosslink.

Half-life of 7D8-HG is evaluated in vivo in a mouse pharmacokinetic (PK) experiment and compared with 7D8-IgG4. Although 7D8-HG has a 2 to 3 times faster clearance than normal IgG4 in this model, the 6 day half-life is counted favorable to the half-life of less than one day reported for IgG F(ab')2 fragments. We conclude that the favorable PK-profile will make IgG4-hingeless antibodies valuable for therapeutic applications when a non-crosslinking, monovalent and non-complement-activating antibody is needed.

Example 61

Constructions and Biochemical Analysis of CH3 Variants of 2F8-HG

To prevent dimerization irrespective of the presence of irrelevant antibodies, additional mutations were introduced into the CH3 region. To make the constructs for the expression of the CH3 mutants, the mutations were introduced into pTomG42F8HG using site-directed mutagenesis. The constructs were expressed transiently.

In order to investigate whether CH3 variant HG molecules exist as monomers or dimers, a mass spectrometry method was employed as described above.

FIG. 30 shows a summary of the monomer/dimer ratios obtained for each HG mutant using non-covalent nano-electrospray mass spectrometry. CH3 mutants showed a substantial increase in monomer/dimer ratio compared to 2F8-HG (WT). The percentage molecules present as monomers increased from 15% in 2F8-HG (WT) to >80% in most CH3 mutants, except for mutation R277A. HG mutation R277K, which introduces an IgG1 sequence into the IgG4 backbone, was used as negative control. As expected, this mutant behaved as dimer.

The monomer or dimer configuration of CH3 mutants was verified using NativePAGE™ Novex® Bis-Tris gel electrophoresis (Invitrogen, Carlsbad, Calif.) according to the instructions of the manufacturer as shown in FIG. 31. This native gel electrophoresis technique uses Coomassie G-250 as a charge-shift molecule instead of SDS and is able to maintain native protein conformation and protein complex quaternary structures (Schägger H and von Jagow G 1991 Blue native gel electrophoresis for isolation of membrane complexes in enzymatically active form. Anal. Biochem. 199: 223-244).

Under these experimental conditions, 2F8-HG (WT) and R277K and R277A showed a protein band corresponding to the size of a full tetrameric (two heavy and two light chains) molecule. The CH3 mutants T234A, L236A, L236V, F273A, F273L, and Y275A were shown to be half molecules (only one heavy and one light chain).

Example 62

Functional Analysis of CH3 Mutants of 2F8-HG

Binding of 2F8-HG (WT) and variants was determined in the absence and presence of 200 μg/ml polyclonal human IgG (Intravenous Immunoglobulin, IVIG, Sanquin Netherlands) (as described in Example 57).

FIGS. 32 and 33 show that the binding curve of 2F8-HG in the presence of IVIG clearly right-shifts with respect to the binding curve of 2F8-HG without IVIG. This difference in avidity for the EGFr coat is consistent with the idea that, in the presence of IVIG, 2F8-HG binds monovalently (see Example 57). The binding curves of several of the tested mutations, 2F8-HG-T234A, 2F8-HG-L236V, 2F8-HG-L236A and 2F8-HG-Y275A, become insensitive to the addition of IVIG and were super-imposable on the monovalent binding curve of 2F8-HG in the presence of IVIG. These differences in avidity for the EGFr coat are consistent with the idea that the 2F8-HG-T234A, 2F8-HG-L236V, 2F8-HG-L236A and 2F8-HG-Y275A mutations prevent dimerization of the HG molecules.

Example 63

Functional Analysis of CH3 Mutants of 2F8-HG

CH3 mutants of 2F8-HG were shown to bind EGFr with lower apparent affinities than 2F8-HG in a binding ELISA coated with EGFr protein (see above). The potency of 2F8-HG CH3 mutants to inhibit ligand-induced EGFr phosphorylation in cells in vitro was compared to that of 2F8-HG (WT) and 2F8-Fab fragments in the Phosphorylation Inhibition Assay (PIA) as described in example 54.

CH3 HG mutants were less potent to inhibit EGFr phosphorylation than 2F8-HG (WT) and the control mutants R277K and R277A, in line with the increase in monomer/dimer ratio of these mutants (FIG. 34).

Example 64

Concentration Dependent Configuration of CH3 Mutants of HG

The monomer/dimer configuration of CH3 mutants F273A, L236V, and Y275A was further investigated at different concentrations, ranging from 0.01-10 μM using non-covalent nano-electrospray mass spectrometry as described above. The monomer/dimer configuration of these CH3 mutants was compared to the configuration of 2F8-HG (WT) and R277K.

The percentage molecules present as monomers at each concentration were plotted and EC50 values were calculated for each mutant (FIG. 35).

All HG mutants were 100% monomeric at low concentrations (except for R277K which behaved as dimer). With increased concentration of HG mutants, a decrease in monomericity was observed. However, the figure shows that the CH3 mutants exhibited such decrease in monomericity at much higher concentration than 2F8-HG (WT). Hence, the CH3 mutants contained a higher percentage of monomer molecules at higher molar concentrations.

Example 65

Production of Human Monovalent Antibodies Against EGFr in a Non-Human Transgenic Mouse A transgenic C57BL/6J mice strain is used to generate human monovalent antibodies against EGFr. The mouse strain is homozygous for a transgene comprising, in operable linkage, a plurality of human V genes, a plurality of human D genes, a plurality of human J genes, and a plurality of human $C_H$ genes and associated isotype switch sequences, comprising a human μ $C_H$ gene and a γ $C_H$ gene as set forth in SEQ ID NO:15. Furthermore, the endogenous mouse immunoglobulin heavy chain gene locus, the endogenous mouse immunoglobulin κ light chain gene locus and the endogenous mouse immunoglobulin λ light chain gene locus have been inactivated.

The below immunization schedule is used. Mice are immunized twice with A 431 cells, cultures in High Glucose DMEM, followed by soluble antigen in Ribi Adjuvant. The EGFR specific serum titer is determined by ELISA after the third immunization. Three different immunizations are performed for the final boosts before the fusion. These include two or three sequential intravenous (iv) boosts via the tail vein with 10 μg of antigen in 50 μl PBS or two sequential intraperitoneal (i.p.) boosts with 25 μg soluble EGFr in Ribi adjuvant.

| | | Immunization Schedule | | | | | | |
|---|---|---|---|---|---|---|---|---|
| Mouse | A431 cells Day 1 | A431 cells Day 20 | ELISA Titer Day 30 | EGFR in Ribi ip Day 33 | ELISA Titer Day 43 | Fusion Day 46 | EGFR in RIBI ip Day 50 | Fusion Day 53 |
| #1 | 2 × 10⁶ | 1 × 10⁷ | 0 | 25 μg | Titer determination | | 25 μg | Ribi 2 × 25 μg*** |
| #2 | 2 × 10⁶ | 1 × 10⁷ | 0 | 25 μg | Titer determination | | 25 μg | 2 iv × 10 μg** |
| #3 | 2 × 10⁶ | 1 × 10⁷ | 450 | 25 μg | Titer determination | 3 iv × 10 μg* | | |

*EGFR in PBS (10 μg) iv (tail) on days −4, −3, and −2
**EGFR in PBS (10 μg) iv (tail) on day −4, and −3
***EGFR in Ribi (25 μg) ip on day −4 and −3

Mice showing a robust response level to EGFr after repeated immunizations are prepared for fusion according to standard procedures.

Example 66

Hybridoma Preparation

The P3 X63 ag8.653 myeloma cell line (ATCC CRL 1580, lot F-15183) is used for the fusions. The original ATCC vial is thawed and expanded in culture. A seed stock of frozen vials is prepared from this expansion. A fresh vial of cells is thawed one to two weeks before the fusions.

High Glucose DMEM (Mediatech, Cellgro #10013) containing 10% FBS, Pennicillin-Streptomycin (Sigma, P-7539), and $5.5 \times 10^{-5}$ M 2-mercaptoethanol (GibcoBRL, 21985-023) is used to culture myeloma cells. Additional media supplements are added to the hybridoma growth media, which includes: 3% Origin-Hybridoma Cloning Factor (Igen, 21001), OPI supplement (Sigma, O-5003), $1.1 \times 10^{-3}$ M Oxalo acetic acid, $4.5 \times 10^{-4}$ M sodium Pyruvate, and 24 international units/L bovine Insulin, HAT (Sigma, H 0262) $1.0 \times 10^{-4}$ M Hypoxanthine, $4.0 \times 10^{-7}$ M Aminopterin, $1.6 \times 10^{-5}$ M Thymidine, or HT (Sigma, H0137) $1.0 \times 10^{-4}$ M Hypoxanthine, $1.6 \times 10^{-5}$ M Thymidine. Characterized Fetal bovine serum (SH30071 lot #s AJE10321 and AGH6843) may be obtained from Hyclone, Logan, Utah. Serum Free medium contains DMEM, antibiotics and 2-mercaptoethanol only.

The splenocytes from the immunized mice are fused to the myeloma cell line according to standard procedures.

The initial ELISA screen for human IgG4 κ antibodies is performed 7-10 days post fusion. Human IgG4, κ positive wells are screened on soluble EGFR coated ELISA plates. Antigen positive hybridomas are transferred to 24 well plates and eventually to tissue culture flasks. EGFR specific hybridomas are subcloned by limiting dilution to assure monoclonality. Antigen positive hybridomas are preserved at several stages in the development process by freezing cells in DMEM 10% FBS plus 10% DMSO (Sigma, D2650) or in Origen Freeze Medium (Igen, #210002). Cells are stored at −80° C. or in $LN_2$. Initial EGFR specific hybridomas are subsequently screened for desired characteristics and selected for further characterization.

The invention claimed is:

1. An isolated monovalent IgG4 antibody that binds to a selected antigen, which monovalent antibody comprises
   a heavy chain, which heavy chain comprises
   (i) a human VH region, and
   (ii) a human CH region comprising a hinge region and a CH3 region, wherein the CH region has been modified such that the region corresponding to the hinge region does not comprise any amino acid residues which are capable of forming disulfide bonds with an identical CH region, and wherein the CH3 region has the sequence as set forth in SEQ ID NO: 16, but wherein the CH3 region has been modified so that one of the following amino acid substitutions has been made: Phe (F) in position 273 has been replaced by Ala (A); Phe (F) in position 273 has been replaced by Leu (L); Phe (F) in position 273 has been replaced by Asp (D); Phe (F) in position 273 has been replaced by Thr (T), and
   a light chain, which light chain comprises
   (i) a human VL region, and
   (ii) a human CL region.

2. The monovalent antibody according to claim 1, wherein Phe (F) in position 273 has been replaced by Ala (A).

3. The monovalent antibody according to claim 1, wherein Phe (F) in position 273 has been replaced by Leu (L).

4. The monovalent antibody according to claim 1, wherein the monovalent antibody further comprises a CH2 region as set forth in SEQ ID NO: 16, but wherein Thr (T) in position 118 has been replaced by Gln (Q) and/or Met (M) in position 296 has been replaced by Leu (L).

5. The monovalent antibody according to claim 1, wherein the monovalent antibody further comprises a CH2 region as set forth in SEQ ID NO: 16, but wherein one, two or all three of the following substitutions have been made: Met (M) in position 120 has been replaced by Tyr (Y); Ser (S) in position 122 has been replaced by Thr (T); and Thr (T) in position 124 has been replaced by Glu (E).

6. The monovalent antibody according to claim 1, wherein the monovalent antibody further comprises a CH2 region as set forth in SEQ ID NO: 16, but wherein Asn (N) in position 302 has been replaced by Ala (A) and Thr (T) in position 175 has been replaced by Ala (A) and Glu (E) in position 248 has been replaced by Ala (A).

* * * * *